US012594431B2

(12) United States Patent
Beyer et al.

(10) Patent No.: US 12,594,431 B2
(45) Date of Patent: Apr. 7, 2026

(54) AED ACTIONS REMOTELY TRIGGERED BY AED MANAGEMENT PLATFORM

(71) Applicant: Avive Solutions, Inc., Brisbane, CA (US)

(72) Inventors: Rory M. Beyer, San Mateo, CA (US); Sameer Jafri, San Diego, CA (US); Micah R. Bongberg, Kirkland, WA (US)

(73) Assignee: Avive Solutions, Inc., Brisbane, CA (US)

( * ) Notice: Subject to any disclaimer, the term of this patent is extended or adjusted under 35 U.S.C. 154(b) by 163 days.

(21) Appl. No.: 18/653,274

(22) Filed: May 2, 2024

(65) Prior Publication Data

US 2024/0371512 A1 Nov. 7, 2024

Related U.S. Application Data

(60) Provisional application No. 63/499,662, filed on May 2, 2023.

(51) Int. Cl.
*A61N 1/39* (2006.01)
*A61N 1/02* (2006.01)
(Continued)

(52) U.S. Cl.
CPC ........... *A61N 1/3993* (2013.01); *A61N 1/025* (2013.01); *A61N 1/046* (2013.01); *A61N 1/3625* (2013.01);
(Continued)

(58) Field of Classification Search
None
See application file for complete search history.

(56) References Cited

U.S. PATENT DOCUMENTS 6,292,687 B1 9/2001 Lowell et al.
6,356,785 B1 3/2002 Snyder et al.
(Continued)

FOREIGN PATENT DOCUMENTS

CN 105013085 11/2015
CN 108671401 10/2018
(Continued)

OTHER PUBLICATIONS

Halperin et al., Security and Privacy for Implantable Medical Devices, Security and Privacy for Implantable Devices; IEEE Pervasive Computing ( vol. 7, Issue: 1, Jan.-Mar. 2008).*
(Continued)

*Primary Examiner* — David J Stoltenberg
(74) *Attorney, Agent, or Firm* — Beyer Law Group LLP

(57) ABSTRACT

Medical device management platforms, as for example, automated external defibrillator (AED) management platforms are described. The disclosure also describes systems, management platform graphical user interfaces, management server infrastructures, connected automated external defibrillators (AEDs), and protocols for communications between such system/devices that make it easier for owners, administrator, and others to manage their devices. The present disclosure also describes mechanisms that facilitate getting incident information to interested parties, including medical personnel, EMS personnel and others when an AED is used.

25 Claims, 22 Drawing Sheets

(51) Int. Cl.

| | |
|---|---|
| *A61N 1/04* | (2006.01) |
| *A61N 1/362* | (2006.01) |
| *G06F 3/0484* | (2022.01) |
| *G16H 40/63* | (2018.01) |
| *H04L 9/40* | (2022.01) |
| *H04L 67/12* | (2022.01) |

(52) U.S. Cl.
CPC ......... *A61N 1/3904* (2017.08); *A61N 1/3981* (2013.01); *G06F 3/0484* (2013.01); *G16H 40/63* (2018.01); *H04L 63/20* (2013.01); *H04L 67/12* (2013.01)

(56) References Cited

U.S. PATENT DOCUMENTS

| | | | |
|---|---|---|---|
| 6,493,581 B2 | 12/2002 | Russell | |
| 6,658,290 B1 | 12/2003 | Lin et al. | |
| 6,747,556 B2 | 6/2004 | Medema et al. | |
| 6,834,207 B2 | 12/2004 | Miyauchi et al. | |
| 6,937,150 B2 | 8/2005 | Medema et al. | |
| 6,993,386 B2 | 1/2006 | Lin et al. | |
| 7,289,029 B2 | 10/2007 | Medema et al. | |
| 8,086,320 B2 | 12/2011 | Saketkhou | |
| 8,180,457 B2 | 5/2012 | Matos | |
| 8,209,008 B2 | 6/2012 | Hansen et al. | |
| 8,565,871 B2 | 10/2013 | Tuysserkani | |
| 8,706,225 B2 | 4/2014 | Matos | |
| 8,818,522 B2 | 8/2014 | Mass et al. | |
| 8,880,168 B2 | 11/2014 | Pearce et al. | |
| 8,981,927 B2 | 3/2015 | McSheffrey | |
| 9,026,147 B2 | 5/2015 | Galvin et al. | |
| 9,035,787 B2 | 5/2015 | Bongberg et al. | |
| 9,101,527 B2 | 8/2015 | Madanat | |
| 9,232,040 B2 | 1/2016 | Barash et al. | |
| 9,289,621 B2 | 3/2016 | Aoyama et al. | |
| 9,295,849 B2 | 3/2016 | Elghazzawi et al. | |
| 9,307,383 B1 | 4/2016 | Patrick | |
| 9,324,120 B2 | 4/2016 | Braun | |
| 9,480,852 B2 | 11/2016 | Bonnamy | |
| 9,498,152 B2 | 11/2016 | Bowers | |
| 9,592,401 B2 | 3/2017 | Freeman et al. | |
| 9,619,767 B2 | 4/2017 | Braun | |
| 9,628,946 B2 | 4/2017 | Elghazzawi | |
| 9,847,030 B2 | 12/2017 | Kadobayashi et al. | |
| 9,848,058 B2 | 12/2017 | Johnson et al. | |
| 9,872,998 B2 | 1/2018 | Aoyama et al. | |
| 9,889,311 B2 | 2/2018 | Horseman et al. | |
| 9,897,459 B2 | 2/2018 | Johnson | |
| 9,987,193 B2 | 6/2018 | Freeman | |
| 10,029,109 B2 | 7/2018 | Beyer et al. | |
| 10,035,023 B2 | 7/2018 | Das | |
| 10,058,469 B2 | 8/2018 | Freeman | |
| 10,058,709 B2 | 8/2018 | Tilton, Jr. | |
| 10,090,716 B2 | 10/2018 | Stever et al. | |
| 10,092,767 B1 | 10/2018 | Newton et al. | |
| 10,099,061 B2 | 10/2018 | Buchanan | |
| 10,159,848 B2 | 12/2018 | Amann et al. | |
| 10,178,534 B2 | 1/2019 | Barash et al. | |
| 10,258,806 B2 | 4/2019 | Elghazzawi et al. | |
| 10,298,072 B2 | 5/2019 | Stever et al. | |
| 10,381,118 B2 | 8/2019 | Kellum | |
| 10,449,380 B2 | 10/2019 | Andrews | |
| 10,504,622 B2 | 12/2019 | Gallopyn et al. | |
| 10,543,379 B2 | 1/2020 | Hingston et al. | |
| 10,565,845 B1 | 2/2020 | Beyer et al. | |
| 10,580,280 B1 | 3/2020 | Picco et al. | |
| 10,621,846 B1 | 4/2020 | Beyer et al. | |
| 10,638,929 B2 | 5/2020 | Kaib et al. | |
| 10,657,796 B2 | 5/2020 | Bowers | |
| 10,665,078 B1 | 5/2020 | Picco et al. | |
| 10,737,105 B2 | 8/2020 | Andrews et al. | |
| 10,744,063 B2 | 8/2020 | Freeman | |
| 10,773,091 B2 | 9/2020 | Andrews et al. | |
| 10,792,506 B2 | 10/2020 | Elghazzawi | |
| 10,796,396 B2 | 10/2020 | Braun et al. | |
| 10,806,939 B1 | 10/2020 | Malott et al. | |
| 10,857,371 B2 | 12/2020 | Gustavson et al. | |
| 10,861,310 B2 | 12/2020 | Picco et al. | |
| 10,924,553 B2 | 2/2021 | Durrant et al. | |
| 10,933,249 B2 | 3/2021 | Elghazzawi et al. | |
| 10,946,209 B2 | 3/2021 | Andrews et al. | |
| 10,957,178 B2 | 3/2021 | Beyer et al. | |
| 11,077,312 B2 | 8/2021 | Sturman et al. | |
| 11,138,855 B2 | 10/2021 | Jafri et al. | |
| 11,595,478 B2 | 2/2023 | Durrant et al. | |
| 11,645,899 B2 | 5/2023 | Jafri et al. | |
| 11,869,338 B1 | 1/2024 | Beyer et al. | |
| 11,924,282 B2 | 3/2024 | Durrant et al. | |
| 11,980,767 B2 | 5/2024 | Elghazzawi et al. | |
| 2003/0028219 A1 | 2/2003 | Powers et al. | |
| 2003/0149759 A1 | 8/2003 | Hetherington et al. | |
| 2004/0015191 A1 | 1/2004 | Otman et al. | |
| 2004/0049233 A1 | 3/2004 | Edwards | |
| 2004/0064342 A1 | 4/2004 | Browne et al. | |
| 2006/0030891 A1 | 2/2006 | Saltzstein et al. | |
| 2006/0041278 A1 | 2/2006 | Cohen et al. | |
| 2006/0149321 A1 | 7/2006 | Merry et al. | |
| 2006/0149322 A1 | 7/2006 | Merry et al. | |
| 2006/0149323 A1 | 7/2006 | Merry et al. | |
| 2007/0032830 A1 | 2/2007 | Bowers | |
| 2007/0136099 A1 | 6/2007 | Neligh et al. | |
| 2007/0162075 A1 | 7/2007 | O'hara | |
| 2007/0270909 A1 | 11/2007 | Saketkhou | |
| 2007/0299473 A1 | 12/2007 | Matos | |
| 2008/0250166 A1 | 10/2008 | Edwards | |
| 2009/0070148 A1 | 3/2009 | Skocic | |
| 2009/0149894 A1 | 6/2009 | Merry et al. | |
| 2009/0284378 A1 | 11/2009 | Ferren et al. | |
| 2010/0017471 A1 | 1/2010 | Brown et al. | |
| 2010/0174560 A1 | 7/2010 | Quan et al. | |
| 2010/0286490 A1 | 11/2010 | Koverzin | |
| 2011/0060378 A1* | 3/2011 | Tuysserkani ......... | A61B 5/0022 370/352 |
| 2011/0071880 A1 | 3/2011 | Spector | |
| 2011/0117878 A1 | 5/2011 | Barash et al. | |
| 2011/0152702 A1 | 6/2011 | Goto | |
| 2012/0232355 A1 | 9/2012 | Freeman | |
| 2013/0012151 A1 | 1/2013 | Hankins | |
| 2013/0065628 A1 | 3/2013 | Pfeffer | |
| 2013/0296719 A1 | 11/2013 | Packer et al. | |
| 2013/0304850 A1* | 11/2013 | Mahaffey ................ | H04L 41/22 709/217 |
| 2014/0002241 A1 | 1/2014 | Elghazzawi | |
| 2014/0004814 A1 | 1/2014 | Elghazzawi | |
| 2014/0031884 A1 | 1/2014 | Elghazzawi | |
| 2014/0222096 A1 | 8/2014 | Hu et al. | |
| 2014/0222466 A1 | 8/2014 | Kellum | |
| 2014/0266718 A1* | 9/2014 | Bongberg ............ | A61N 1/3904 340/540 |
| 2015/0206408 A1 | 7/2015 | LaLonde et al. | |
| 2015/0343229 A1 | 12/2015 | Peterson et al. | |
| 2016/0066653 A1 | 3/2016 | Piva et al. | |
| 2016/0133160 A1 | 5/2016 | Packer et al. | |
| 2016/0140834 A1 | 5/2016 | Tran | |
| 2016/0148495 A1 | 5/2016 | Buchanan | |
| 2016/0162644 A1* | 6/2016 | Bindelglass ........... | G16H 10/20 705/3 |
| 2016/0210581 A1 | 7/2016 | Braun | |
| 2016/0213942 A1 | 7/2016 | Elghazzawi et al. | |
| 2016/0294951 A1 | 10/2016 | Durant et al. | |
| 2016/0328950 A1 | 11/2016 | Pelletier et al. | |
| 2017/0021185 A1 | 1/2017 | Das | |
| 2017/0028211 A1 | 2/2017 | Tilton, Jr. | |
| 2017/0172424 A1 | 6/2017 | Eggers et al. | |
| 2017/0251347 A1 | 8/2017 | Mehta et al. | |
| 2017/0273116 A1 | 9/2017 | Elghazzawi | |
| 2017/0281016 A1 | 10/2017 | Elghazzawi | |
| 2017/0281461 A1 | 10/2017 | Kokubo et al. | |
| 2017/0289350 A1 | 10/2017 | Philbin | |
| 2017/0312530 A1* | 11/2017 | Schilling ............ | A61N 1/37223 |
| 2017/0367927 A1 | 12/2017 | Cervantes | |
| 2018/0169426 A1 | 6/2018 | Montague et al. | |
| 2018/0369598 A1 | 12/2018 | Newton et al. | |

(56) References Cited

U.S. PATENT DOCUMENTS

| | | | |
|---|---|---|---|
| 2019/0038133 A1 | 2/2019 | Tran | |
| 2019/0044362 A1 | 2/2019 | Beyer et al. | |
| 2019/0099608 A1 | 4/2019 | Elghazzawi et al. | |
| 2019/0111272 A1* | 4/2019 | Hochhalter | A61N 1/3925 |
| 2019/0117983 A1 | 4/2019 | Andrews et al. | |
| 2019/0117984 A1 | 4/2019 | Andrews et al. | |
| 2019/0117987 A1 | 4/2019 | Beyer et al. | |
| 2019/0117988 A1 | 4/2019 | Beyer et al. | |
| 2019/0124466 A1 | 4/2019 | Masterson et al. | |
| 2019/0159009 A1 | 5/2019 | Barash et al. | |
| 2019/0168010 A1 | 6/2019 | Elghazzawi | |
| 2019/0174289 A1 | 6/2019 | Martin et al. | |
| 2019/0279327 A1 | 9/2019 | Braun et al. | |
| 2019/0306664 A1 | 10/2019 | Mehta et al. | |
| 2019/0318827 A1 | 10/2019 | Chiu et al. | |
| 2020/0054885 A1 | 2/2020 | Aprile | |
| 2020/0090483 A1 | 3/2020 | Picco et al. | |
| 2020/0092700 A1 | 3/2020 | Picco et al. | |
| 2020/0206517 A1 | 7/2020 | Martin et al. | |
| 2020/0221263 A1 | 7/2020 | Sturman et al. | |
| 2020/0242907 A1 | 7/2020 | Beyer et al. | |
| 2020/0267509 A1* | 8/2020 | Stapleford | H04W 4/029 |
| 2020/0286352 A1 | 9/2020 | Beyer et al. | |
| 2020/0286353 A1 | 9/2020 | Jafri et al. | |
| 2020/0321108 A1* | 10/2020 | Reid | G16H 40/67 |
| 2020/0373005 A1 | 11/2020 | Halsne et al. | |
| 2020/0406046 A1 | 12/2020 | Beattie, Jr. | |
| 2021/0136531 A1 | 5/2021 | Dorian et al. | |
| 2021/0142639 A1 | 5/2021 | Beyer et al. | |
| 2021/0153817 A1 | 5/2021 | Beyer et al. | |
| 2021/0154487 A1 | 5/2021 | Bongberg et al. | |
| 2021/0205629 A1 | 7/2021 | Elghazzawi et al. | |
| 2021/0228893 A1* | 7/2021 | Akram | A61N 1/3925 |
| 2021/0314757 A1 | 10/2021 | Pellegrini et al. | |
| 2022/0339454 A1* | 10/2022 | Sturman | A61N 1/3904 |
| 2022/0359064 A1* | 11/2022 | Pierson | G16H 40/40 |
| 2024/0087733 A1* | 3/2024 | Grey | G16H 40/40 |
| 2024/0096203 A1 | 3/2024 | Beyer et al. | |
| 2024/0366953 A1 | 11/2024 | Beyer et al. | |
| 2024/0371511 A1 | 11/2024 | Beyer et al. | |
| 2025/0099774 A1* | 3/2025 | Ito | A61N 1/3904 |

FOREIGN PATENT DOCUMENTS

| | | | | |
|---|---|---|---|---|
| CN | 110898331 | | 3/2020 | |
| CN | 202010742228 A | * | 7/2020 | G08B 21/24 |
| CN | 111539866 | | 8/2020 | |
| CN | 202111581584 A | * | 12/2021 | G06F 21/45 |
| DE | 202004002106 | | 6/2004 | |
| EP | 1157717 | | 1/2005 | |
| EP | 2218478 | | 8/2010 | |
| EP | 2879759 | | 10/2019 | |
| JP | 2001/325689 | | 11/2001 | |
| KR | 20160012239 | | 2/2016 | |
| KR | 101780214 | | 10/2017 | |
| KR | 102152282 | | 9/2020 | |
| KR | 2022-0067544 A | * | 6/2022 | A61N 1/39 |
| WO | 2010/66014 | | 6/2010 | |
| WO | 2018/069383 | | 4/2018 | |
| WO | WO 2022/071622 | | 4/2022 | |

OTHER PUBLICATIONS

Zhang et al. Spatiotemporal Optimization for the Placement of Automated External Defibrillators Using Mobile Phone Data; ISPRS Int J Geoinf. Mar. 2023 ; 12(3): oi: 10.3390/ijgi 12030091;.*

International Search Report and Written Opinion dated Sep. 11, 2024 from International Application No. PCT/US2024/027408.

Bongberg et al., U.S. Appl. No. 17/217,738, filed Mar. 30, 2021.

Kanaan et al., "An Advanced Therapeutic Drone Attached with Automated External Defibrillator (AED) for Rural Areas", 2023 7th International Conference on Trends in Electronics and Informatics (ICOEI), Tirunelveli, India, 2023, pp. 298-302, doi: 10.1109/ICOEI56765.2023.10125795.

Samani et al., "Robotic Automated External Defibrillator Ambulance for Emergency Medical Service in Smart Cities", in IEEE Access, vol. 4, pp. 268-283, 2016, doi: 10.1109/ACCESS.2016.2514263.

* cited by examiner

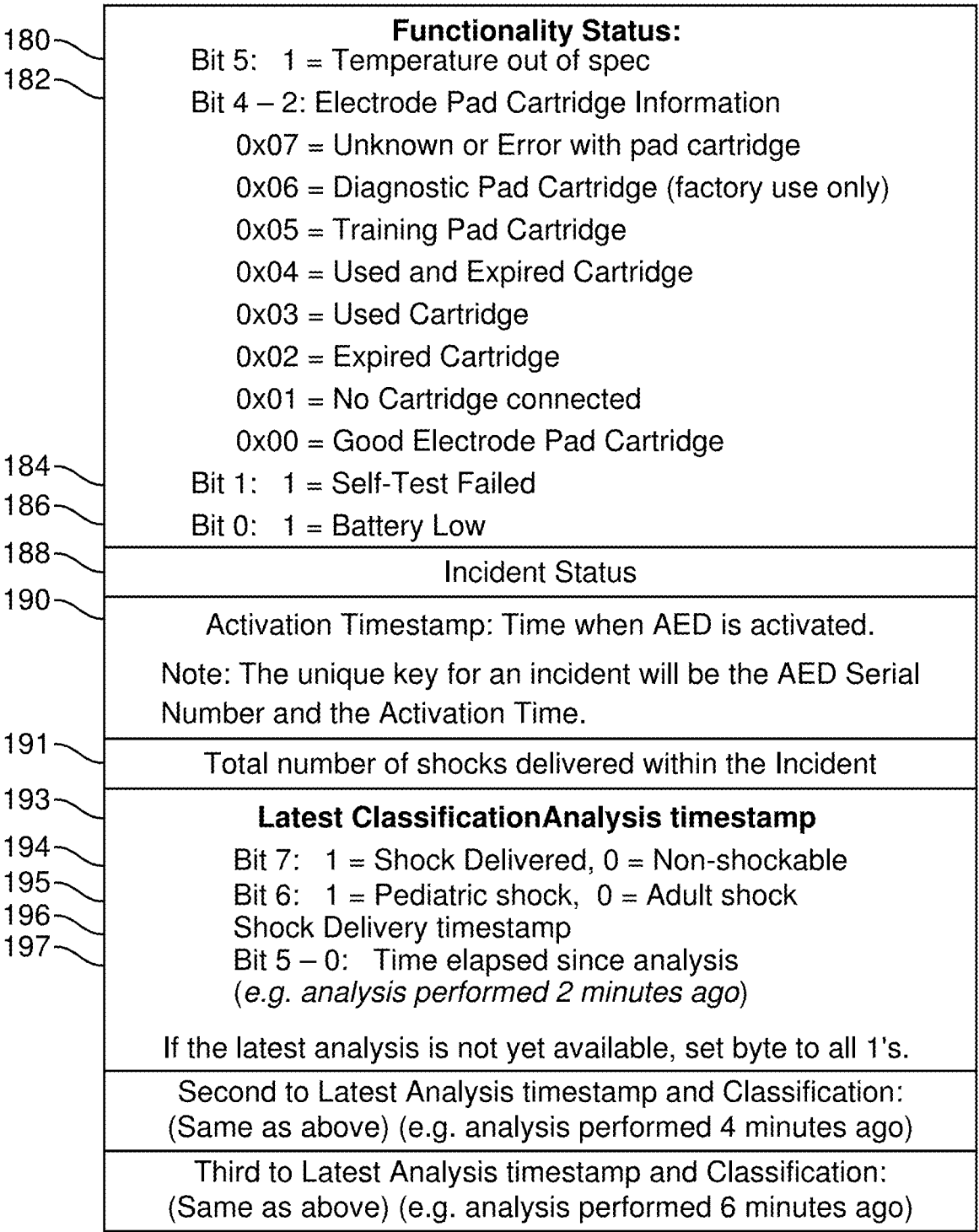

Functionality Status:

Bit 5:  1 = Temperature out of spec

Bit 4 – 2: Electrode Pad Cartridge Information

0x07 = Unknown or Error with pad cartridge

0x06 = Diagnostic Pad Cartridge (factory use only)

0x05 = Training Pad Cartridge

0x04 = Used and Expired Cartridge

0x03 = Used Cartridge

0x02 = Expired Cartridge

0x01 = No Cartridge connected

0x00 = Good Electrode Pad Cartridge

Bit 1:  1 = Self-Test Failed

Bit 0:  1 = Battery Low

Incident Status

Activation Timestamp: Time when AED is activated.

Note: The unique key for an incident will be the AED Serial Number and the Activation Time.

Total number of shocks delivered within the Incident

Latest ClassificationAnalysis timestamp

Bit 7:  1 = Shock Delivered, 0 = Non-shockable
Bit 6:  1 = Pediatric shock,  0 = Adult shock
Shock Delivery timestamp
Bit 5 – 0:  Time elapsed since analysis
(*e.g. analysis performed 2 minutes ago*)

If the latest analysis is not yet available, set byte to all 1's.

Second to Latest Analysis timestamp and Classification:
(Same as above) (e.g. analysis performed 4 minutes ago)

Third to Latest Analysis timestamp and Classification:
(Same as above) (e.g. analysis performed 6 minutes ago)

FIG. 2 (Cont.)

Fleet Map

Fleet Map

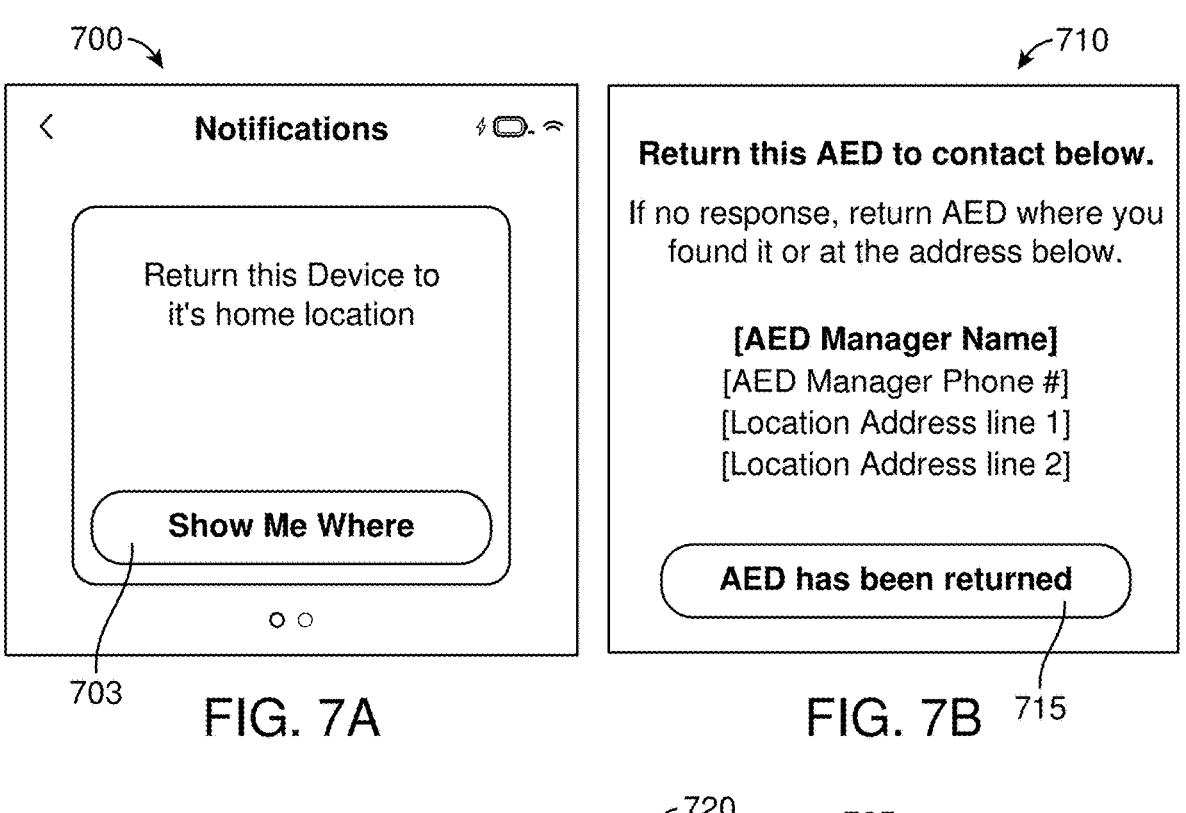
700
Notifications
Return this Device to it's home location
Show Me Where
703
FIG. 7A
710
Return this AED to contact below.
If no response, return AED where you found it or at the address below.
[AED Manager Name]
[AED Manager Phone #]
[Location Address line 1]
[Location Address line 2]
AED has been returned
FIG. 7B 715
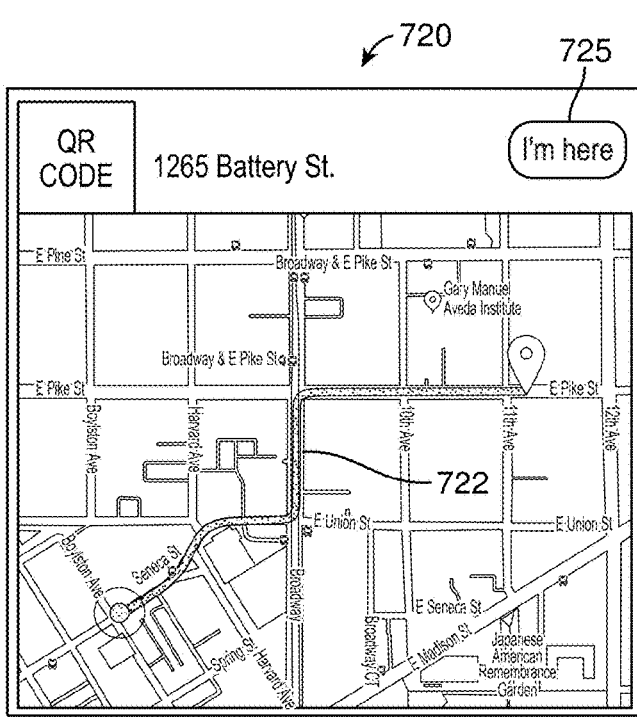
720    725
QR CODE   1265 Battery St.     I'm here
722
FIG. 7C

SELECT SCREENSAVER
UPLOAD WIDGET —803

CHOOSE DESIRED
SCREENSAVER FILE(S) —806

IDENTIFY TARGET
AEDs —809

UPLOAD SCREENSAVER
FILE(S) TO MANAGEMENT
SERVER —812

VALIDATE FILES —814

STORE VALIDATED
FILES IN MANAGEMENT
DATABASE —816

MANAGEMENT SERVER
TRANSMITS SCREENSAVER
FILES TO TARGET AEDs —818

RECEIVING AED ADDS
FILE(S) TO SCREENSAVER
CAROUSEL —820

DISPLAY SCREENSAVER —822

Avive Connect AED<sup>TM</sup> Incident Report
*Not for Diagnostic Purposes*

1010 → Date: 2020-01-03 ←1011

1012 → 911 CALL TIME : 05:08:21 ←1013

1014 → AED Dispatched: 05:09:02 ←1015

1016 → AED ACCEPT INCIDENT : 05:09:51 ← 1017

1020 → AED EN ROUTE: N/A ←1021

1018 → AED Powered On: 05:12:54 ←1019

1022 → Pads Placed: 05:12:55 ←1023

1024 → AED Powered Off: 05:19:37 ←1025

1026 → Incident ID: 3YEE ←1027

1028 → AED Used (Serial #): 02160002 ←1029

1030 → # of Shocks: 2 ←1031

1002 {

1000

Usage Events:
*Elapsed time, from AED Powered On*
0:00:01 - Pads Placed
0:00:43 - Shock Delivered, 50 J (pediatric)
0:02:53 - Shock Delivered, 50 J (pediatric)
0:04:52 Shock not advised

1004 {

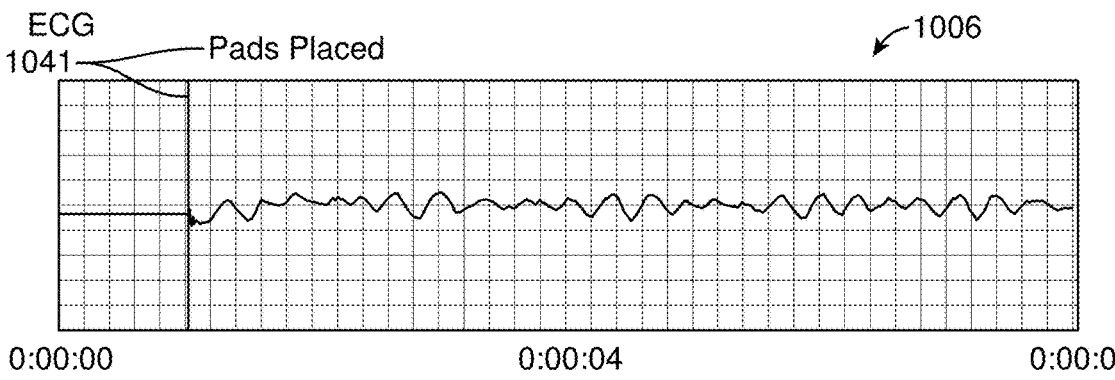

ECG
1041 — Pads Placed

1006

0:00:00          0:00:04          0:00:08

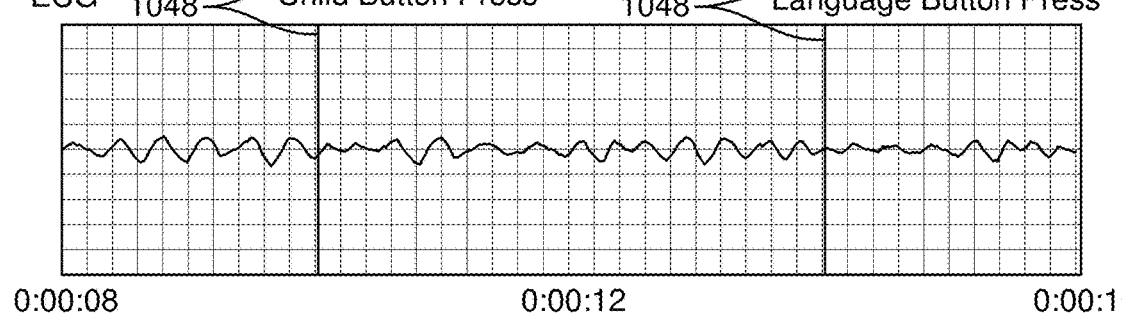

ECG   1048 — Child Button Press          1048 — Language Button Press

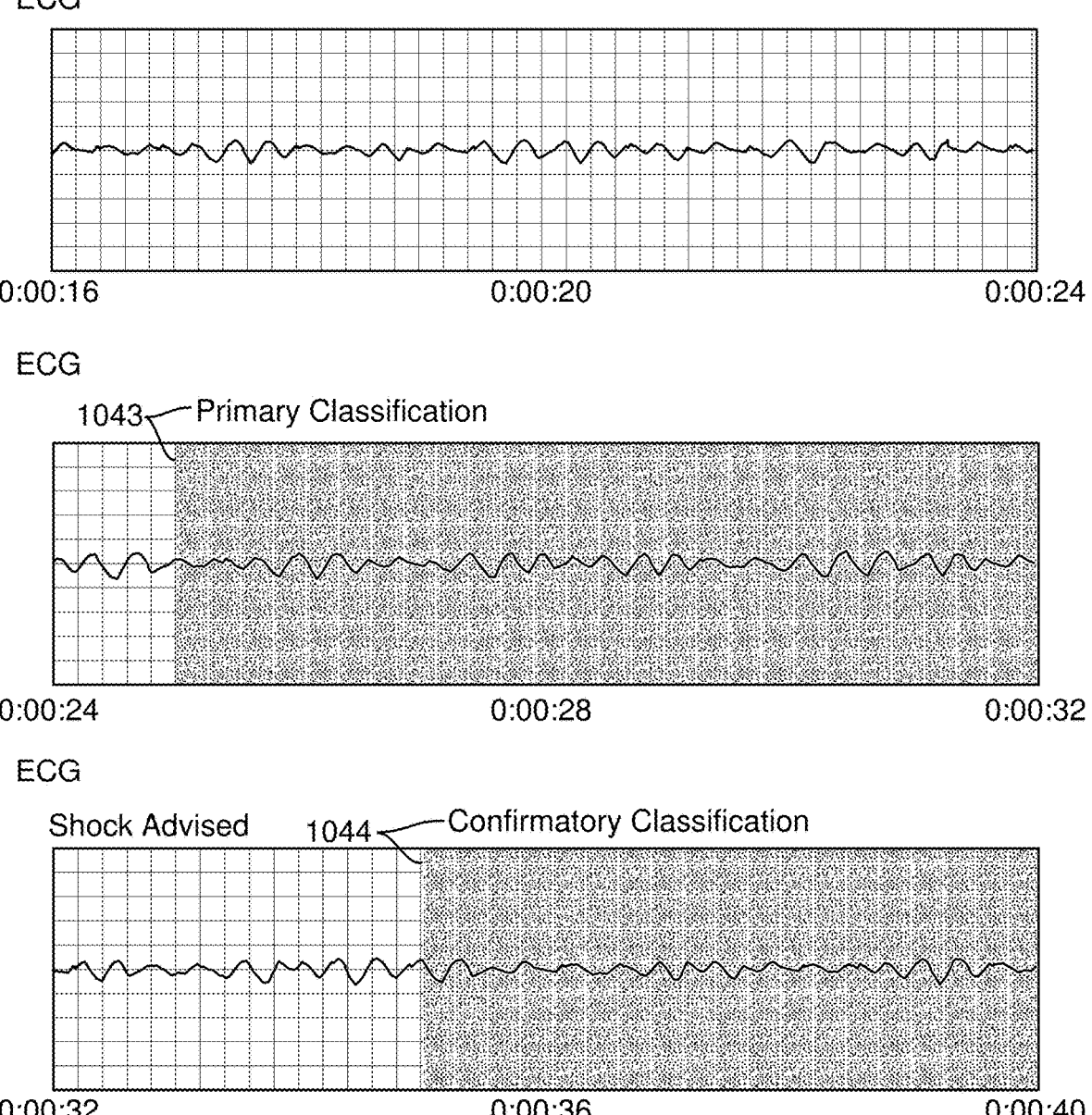
FIG. 10 (Cont. 1)

ECG
Confirmatory Classification  Shock Delivered
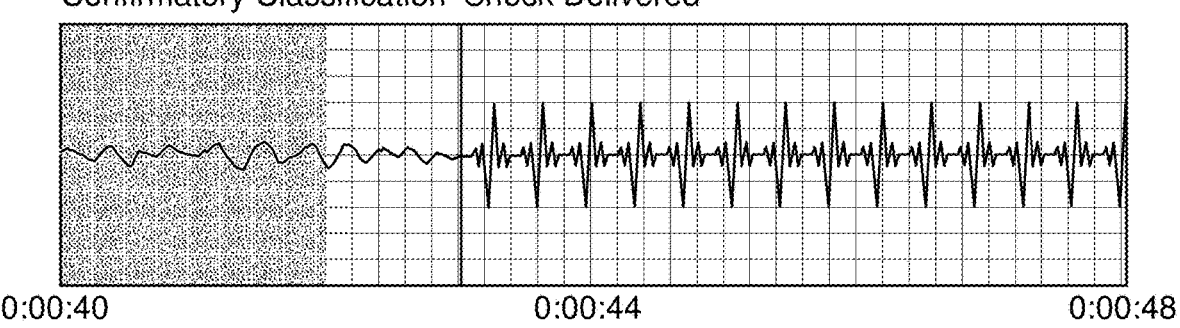
0:00:40                                        0:00:44                                        0:00:48
FIG. 10 (Cont. 2)

AED ACTIONS REMOTELY TRIGGERED BY AED MANAGEMENT PLATFORM

CROSS-REFERENCE TO RELATED APPLICATIONS

This application claims priority of U.S. Provisional Application No. 63/499,662, (P027P) filed on May 2, 2023, which is incorporated by reference herein in its entirety.

FIELD

The present disclosure relates generally to management platforms for medical devices and many of the inventions described herein are particularly applicable to the management of automated external defibrillators (AEDs).

BACKGROUND

Sudden cardiac arrest is one of the leading causes of death. In the United States alone, roughly 350,000 people die each year from sudden cardiac arrest. It is the leading cause of death for individuals over 40 and the #1 killer of student athletes. The most effective treatment for sudden cardiac arrest is the use of CPR coupled with defibrillation. Automated external defibrillators (AEDs) are portable devices designed to automatically check for life-threatening heart rhythms associated with sudden cardiac arrest and to send an electrical shock to the heart to try to restore a normal rhythm when shockable heart rhythms are detected. The two most common conditions treated by AEDs are Pulseless Ventricular tachycardia (aka VT or V-Tach) and Ventricular fibrillation (VF or V-Fib). AEDs are typically designed so that they can be used by a lay person in situations where professional medical help is not available.

Given their potential to save lives, automated external defibrillators have been deployed in a relatively wide variety of public and private locations so that they are available in the event that a person in the vicinity goes into cardiac arrest. By way of example, AEDs may be found in corporate and government offices, shopping centers, airports, airplanes, restaurants, casinos, hotels, sports stadiums, schools, fitness centers and a variety of other locations where people may congregate.

Although the availability of AEDs has increased over the years, there are a number of challenges that make it difficult for owners and administrators to manage their AEDs. This is particularly challenging when an entity is responsible for managing a number of AEDs. Although AED management platforms exit, there are continuing efforts to provide improved AEDs, management tools and incident reporting constructs that made the management of AEDs more effective and/or make it easier to get AED incident data into the hands of personnel that can improve patient outcomes.

SUMMARY

A variety of AED management platforms, AEDs, and methods of managing AEDs are described. In one aspect, a user interface is rendered on an administrator device that enables an administrator to directly or indirectly identify a target AED and a desired operational mode or parameter desired to be applied to the target AED. A first message is sent from the administrator device to an AED management server that directly or indirectly identifies the target AED and the desired operational mode or parameter. In response thereto, the management server transmits a set operational mode or parameter command to the target AED that includes an indication of the desired operational mode or parameter. In response to reception of the set operational mode or parameter command, the target AED sets an operational mode or parameter of the target AED to the desired operational mode or parameter.

In some embodiments, the target AED includes a base defibrillator unit and an interface unit attached to the base defibrillator unit. The interface unit may include a touch sensitive display screen and a communication unit configured to communicate with the management server. In some embodiments, the base defibrillator unit includes (i) a capacitor unit capable of temporarily storing and discharging sufficient energy to deliver a defibrillation shock to a patient, (ii) shock delivery circuitry for discharging the a capacitor unit to deliver the defibrillation shock, (iii) a charging circuit that controls the transfer of energy to the capacitor unit to facilitate charging the capacitor unit to a level suitable to facilitate the delivery of the defibrillation shock to the patient, and (iv) a defibrillator controller configured to determine whether a patient has a shockable heart rhythm based on electrical activity of a heart of the patient.

In some embodiments, the desired operational mode is a desired power mode and the set operational mode command is a set power mode command. In response to reception of the set power mode command, the target AED sets a power mode to the desired power mode. In some embodiments, the set power mode command is received by an interface unit and one of (i) changes an interface power mode of the interface unit without changing a base unit power mode of the base defibrillator unit, (ii) changes the base unit power mode without changing the interface power mode, and (iii) changes both the base unit power mode and the interface power mode.

In some embodiments, the desired operational mode is a desired broadcast mode, and the set operational mode command is a set broadcast mode command. In response to reception of the set broadcast mode command, the target AED sets a broadcast mode of the target AED to the desired broadcast mode. In some embodiments, the desired broadcast mode is one of enable beacons and disable beacons. When the broadcast mode is set to enable beacons, the target AED periodically broadcasts beacons. When the broadcast mode is set to disable beacons, the target AED does not broadcast beacons. In some embodiments, the beacons broadcast by the AED are or include location beacons. In some embodiments, the desired broadcast mode is one of enable advertisements and disable advertisements. When the broadcast mode is set to enable advertisements, the target AED periodically broadcasts advertisements. When the broadcast mode is set to disable advertisements, the target AED does not broadcast advertisements. In some embodiments, the advertisements are Bluetooth Low Energy (BLE) advertisements.

In some embodiments, the desired operational parameter is a security code, and the set operational parameter command is a set security code command. In response to reception of the set security code command, the target AED requires the security code to be provided by a user before the user can make changes to selected AED settings by interacting directly with the AED. In some embodiments, the set security code command is received by an interface unit and is not communicated to the base defibrillator unit. The user must enter the security code on the touch sensitive display screen before any changes are made to the selected AED settings. In some embodiments, no changes may be made to settings of either the base defibrillator unit or the interface unit by interacting directly with the AED without entry of the security code on the touch sensitive display. In some embodiments, the security code is a PIN code or a password.

In some embodiments, the desired operational parameter is a password for accessing a communications network. The user interface rendered on the administrator device enables the administrator to directly or indirectly identify the communications network and the password. The first message and the set operational parameter command both identify the communications network and the password. In response to reception of the set communications network password command, the target AED automatically utilizes the password to access the communications network. In some embodiments, the set communications network password command is received by an interface unit and is not communicated to the base defibrillator unit. The interface unit utilizes the password to access the communications network.

In still other embodiments, the desired operational mode or parameter is a training sequence to be used when the target AED is in a training mode, and the set operational mode or parameter command is a set training sequence command. In response to reception of the set training sequence command, the target AED sets a training sequence of the target AED to the desired training sequence for use when the target AED is placed in a training mode.

In some embodiments, the user interface facilitates the administrator identifying a set of target AEDs by associating the desired operational mode or parameter with one or more group labels that are each associated with a set of one or more AEDs. When the administrator associates the desired operational mode or parameter with a first selected group label, the first message identifies the target AED(s) at least in part by including a first group label identifier that identifies the first selected group label. In response to receiving such a message, the AED management server transmits the set operational mode or parameter commands to each of the target AEDs associated with the first selected group label that are not already in the desired operational mode or using the desired operational parameter.

In some embodiments, when the administrator associates the target AED with a selected group label that was previously associated with the desired operational mode or parameter, the first message indirectly identifies the desired operational mode or parameter at least in part by including a group label identifier that identifies the selected group label. In response thereto, the AED management server automatically transmits the set operational mode or parameter command to the target AED at least partially in response to reception of the first message.

Preferably, the system is set up so that an administrator associated with an owner of the target AED (as opposed to only personnel associated with a manufacturer or distributor) can remotely manage and set operational modes and operational parameters of the target AED.

In another aspect methods of rendering media content on an AED that includes a base defibrillator unit and an interface unit are described. In some embodiments, an interface unit wirelessly receives a media file from a remotely located source, the media file including visual content. While the AED is in a standby mode, the interface unit automatically renders visual content of the media file on the display screen such that passersby can view the visual content of the media file. Preferably, the media file is not passed to or accessible by the base defibrillator unit. In some embodiments, the media file is an administrator supplied file provided by an administrator associated with an owner of the AED via a user interface displayed on an administrator device that enables the administrator to directly or indirectly identify the target AED and the administrator supplied file desired to be provided to the AED.

In another aspect a method of providing a user supplied file to a target AED is described. A user interface is displayed on an administrator device that enables an administrator to directly or indirectly identify the target AED and the user supplied file desired to be provided to the target AED. The administrator device user interface sends a message to the management platform that identifies the target AED and includes at least one of the user supplied file and information that the management server can utilize to identify and obtain the user supplied file desired to be provided to the target AED. At least in part responsive to the reception of the first message, the AED management server automatically transmits the user supplied file to the target AED to facilitate installation of the user supplied file on the target AED to thereby facilitate use of the user supplied file by the target AED.

In some embodiments, the user supplied file is utilized only by an interface unit and is not communicated to the base defibrillator unit. In some embodiments, labels may be used to associate the user supplied file with a group of AEDs and new AEDs may be added to the group as desired to have the associated files automatically communicated to the new AED(s).

In some embodiments, the user supplied file contain network credentials such as a network certificate suitable for use in facilitating wirelessly connecting the target AED to a first communications network. The network certificate is installed on the target AED and may be used by the AED to connect to the first communications. For example, the network certificate may be a Wi-Fi network certificate suitable for use by the AED to connect to a Wi-Fi network. In some embodiments, the network certificate is installed on an interface unit and is not communicated to the base defibrillator unit, whereby only the interface unit portion of the target AED has access to, and utilizes the network certificate.

In some embodiments, the user supplied file is a screen saver to be rendered on a display screen of the target AED at selected times while the target AED is in a standby mode such that passersby can view the visual content of the user supplied media file.

In some embodiments, visual content of the media file is or includes one or more selected from the group consisting of a video, a GIF, a sequence of images, a static image, a GIF. In some embodiments the AED has a carousel of visual content to be displayed on the display screen and visual content included with an update screensaver message is added to the carousel.

In some embodiments, the user interface includes a GUI widget that facilitates administrator selection of designated hours during which the screen saver is to be rendered on the display screen, whereby the administrator selected hours are communicated to the target AED via the management server and the target AED renders the screen saver on the display screen during the designated hours when the target AED is in the standby mode and plugged into power.

AEDs configured to render such screen savers are also described. In some embodiments, the AED includes a base defibrillator unit and an interface unit, and the media file is used only by the interface unit. In such embodiments, the media file is not passed to or accessible by the base defibrillator unit and operation of the base defibrillator unit is not altered in any way by the media file.

In some embodiments the AED includes a carousel to which media containing visual content can be added or deleted. Media in the carousel is rendered as the screen saver.

In another aspect, AEDs are described that are configured to wirelessly receive network credentials from a remotely located source without requiring any user input at the AED. The network credentials are installed on the AED without requiring any user input at the AED and is used by the AED to connect to a wireless network. In embodiments in which the AED includes a base defibrillator unit and an interface unit, the interface unit receives and utilizes the network credentials, the base defibrillator unit has no access to the network certificate, and operation of the base defibrillator unit is not altered in any way by wireless certificate. In some embodiments, the network credentials are or include a network certificate.

In another aspect, methods of obtaining updated status information from an AED are described. An administrator inputs a request for update status information from a target AED in an AED management platform user interface rendered on an administrator computing device. In response to the administrator inputted request, the user interface sends an update request message to an AED management server located remotely relative to the AED management platform user interface. In response to reception of the update request message, the AED management server sends a status check message to the target AED that prompts the target AED to convey current AED status information to the AED management server. At least partially in response to receiving the current status information, the AED management server sends the requested updated status information to the AED management platform user interface that includes at least some of the current status information received from the target AED. The AED management platform user interface then renders the requested updated status information on a display screen associated with the administrator computing device. Preferably, the updated status information is obtained from the target AED and rendered within the AED management platform in real-time in response to the administrator inputted request. In some embodiments, the updated status information is or includes a current location of the target AED. In some embodiments, the target AED opens a communication channel with the AED management server in response to reception of the status check message.

In another aspect, an AED management platform user interface embodied in a computer readable media is configured to display a prompt status check widget in association with a first AED. When the prompt status check widget is activated, the AED management platform user interface sends an update AED status information request to an AED management server that prompts the AED management server to send a status check-in request to the first AED that prompts the first AED to send a first message to the AED management server that provides at least one of a current location of the AED and selected current status information regarding the AED.

In some embodiments, the prompt status check widget is accessible or rendered within an AED status page associated with the first AED. The AED management platform user interface is further configured to receive updated information from the AED management server at least partially in response to the update AED status information request, and to render selected updated information in the AED status page without requiring further input from a user.

In some embodiments, the AED status page includes a map, and the first message and the updated information both include the current location of the AED and upon receipt of the updated status information, the AED status page is updated to show the received current location of the AED on the map. In some embodiments, the AED management platform user interface renders a refresh time that indicates a time that the current location was provided by the AED.

In another aspect, an AED) management user interface embodied in a computer readable media is configured to display a lost mode widget in association with a first AED. When the lost mode widget is activated, the AED management user interface sends a first message to an AED management server that prompts the AED management server to send an activate Missing Protocol command to the first AED that prompts the first AED to send a second message to the AED management server that provides a current location of the AED. In some embodiments, the activate Missing Protocol command causes the AED to repeatedly transmit messages to the messages to the AED management server that each provide a then current location of the AED.

In some embodiments, the activate Missing Protocol command causes the AED to render a render a visual message on a display associated with the AED that provide return instructions that provide instructions indicating how to return the AED to a designated location or to a designated entity, owner, administrator, or person. In some embodiments, the activate Missing Protocol command causes the AED to render an audio alert intended to bring attention to the AED.

In an incident report related aspect methods of providing AED incident reports are described. A server (such as an AED management server or a responder network server) receives selected dispatch information from a Public Safety Answering Point (PSAP) regarding an emergency incident that involves a potential cardiac arrest. The server also receives selected event information from an AED used in connection with the emergency incident. The server automatically creates an electronic AED incident report that includes the selected dispatch information and the selected event information and electronically transmits the electronic AED incident report from the first server to an interested party where it can be rendered on a device associated with the interested party that is located remotely relative to the PSAP. The receiving party can also be remote relative to the AED and the emergency incident.

In another incident report related aspect, methods of providing an AED incident report that reports incident information related to an emergency use of an automated external defibrillator (AED) to an interested party in real-time during emergency use of the AED are described. A server receives selected event information from the AED during the emergency use of the AED and automatically creates an electronic AED incident report that includes the selected event information. The AED incident report is electronically transmitted from the first server to an interested party during the emergency use of the AED, wherein the interested party is not a telecommunicator at a public safety answering point (PSAP).

In either of the incident report related method aspects, in some embodiments, the AED incident report is rendered on a user device associated with the interested party in real time while the AED is still in use. In some embodiments, the rendered AED incident report is updated while the AED is still in use to incorporate additional event data reported by the AED after the AED incident report was first created.

In some embodiments, the interested party is one selected from the group consisting of: a medical practitioner unaffiliated with the PSAP; an emergency medical technician or paramedic dispatched by the PSAP to respond to the emergency incident; and an administrator associated with an owner of the AED.

In some embodiments, (i) at least some of the dispatch information is received during the emergency incident, (ii) at least some of the event information received from the AED is received in during the use of the AED in connection with the emergency incident, and/or (iii) the electronic AED incident report is transmitted to the interested party while the emergency incident is still ongoing.

In some embodiments, the dispatch information includes one or more of: a time that a call reporting the emergency incident was received by the PSAP; and a time that a request for volunteer assistance was made or received.

In some embodiments, the selected event information provided in the incident report includes at least one of: a powered on indicator that indicates a time that the AED was turned on; a pads placed indicator that indicates a time that electrode pads were determined by the AED to have been placed on a patient suffering a potential cardiac arrest; a shocks delivered indicator that indicates a number of defibrillations shocks that have been delivered by the AED during the emergency incident; a shock timing indicator that indicates a time that a first defibrillation shock was delivered by the AED; and a shock descriptor that provides a description of the first defibrillation shock.

In some embodiments, the incident report further includes an electrocardiogram detected by the AED during emergency use of the AED in connection with the emergency incident. In some embodiments, the AED incident report is automatically updated after the emergency use of the AED has terminated to include the patient ECG.

In another aspect electronic AED incident reports embodied in a computer readable medium are described. The incident report includes selected event information reported by the AED used to treat the patient, an electrocardiogram of the patient detected and reported by the AED and selected dispatch information provided by a Public Safety Answering Point (PSAP) that participated in managing a professional emergency response to the potential cardiac arrest incident. In some embodiments, the selected event information includes a powered-on indicator that indicates a time that the AED was turned on, a pads placed indicator that indicates a time that electrode pads were determined by the AED to have been placed on the patient. The selected dispatch information includes a time that a call reporting the emergency incident was received by the PSAP.

In some embodiments, the event information further includes a shocks delivered indicator that indicates a number of defibrillations shocks delivered by the AED during the use of the AED. For each defibrillation shock delivered by the AED during the use of the AED, the incident report further includes (i) a shock timing indicator that indicates a time that the defibrillation shock was delivered by the AED, (ii) a shock descriptor that provides a description of the defibrillation shock. In some embodiments, the incident report further includes at least one classification annotation on the ECG, each classification annotation indicting a timing of a segment of the ECG utilized by the AED to make a determination of whether the patient had a shockable heart rhythm. In some embodiments, the incident report further includes at least one shock annotation on the ECG, each shock annotation indicating a timing of a delivery of a defibrillation shock to the patient.

BRIEF DESCRIPTION OF THE DRAWINGS

The invention and the advantages thereof, may best be understood by reference to the following description taken in conjunction with the accompanying drawings in which:

8

Figure 1:
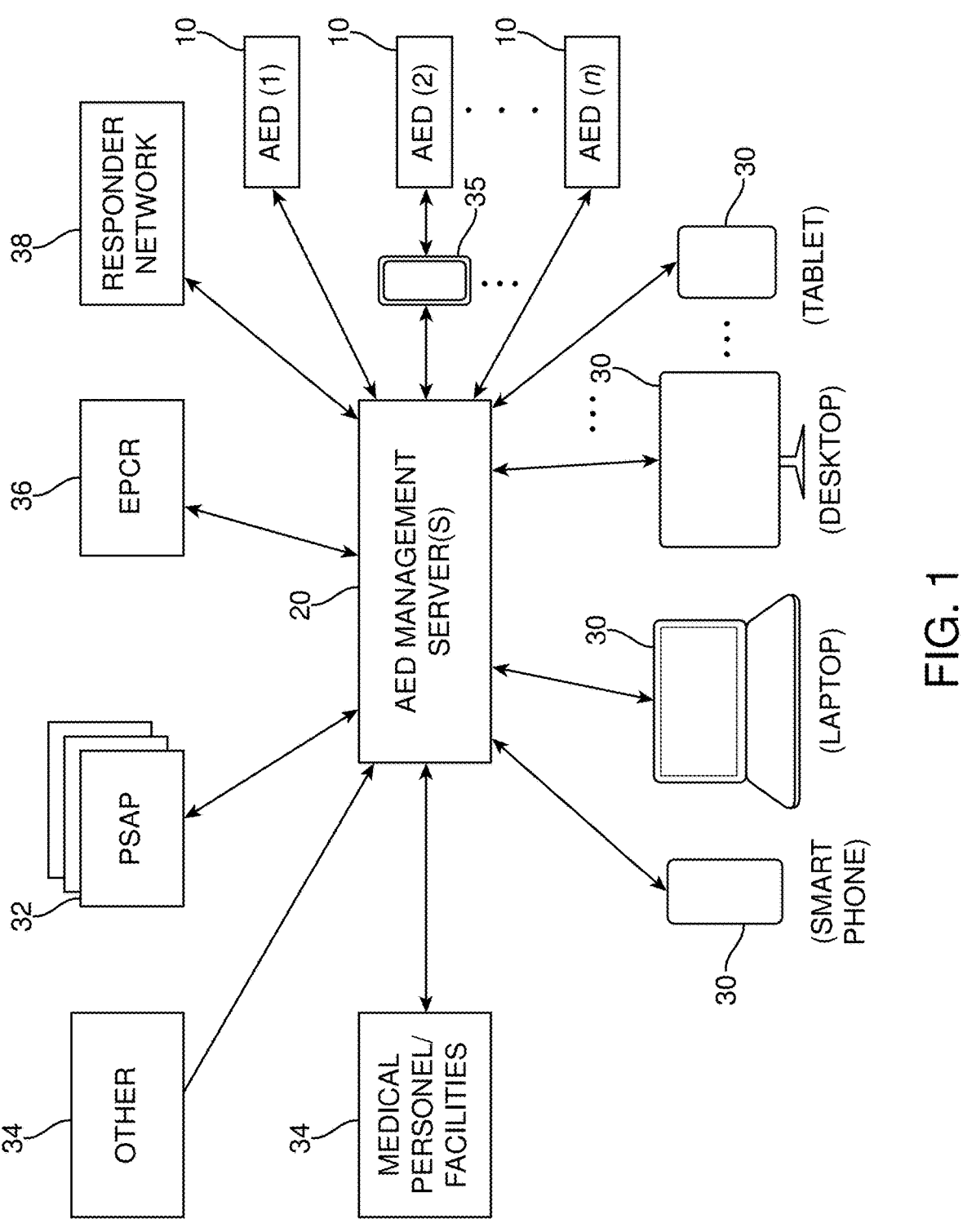

FIG. 1 is a schematic diagram illustrating components of a representative AED management platform environment.

Figure 2:
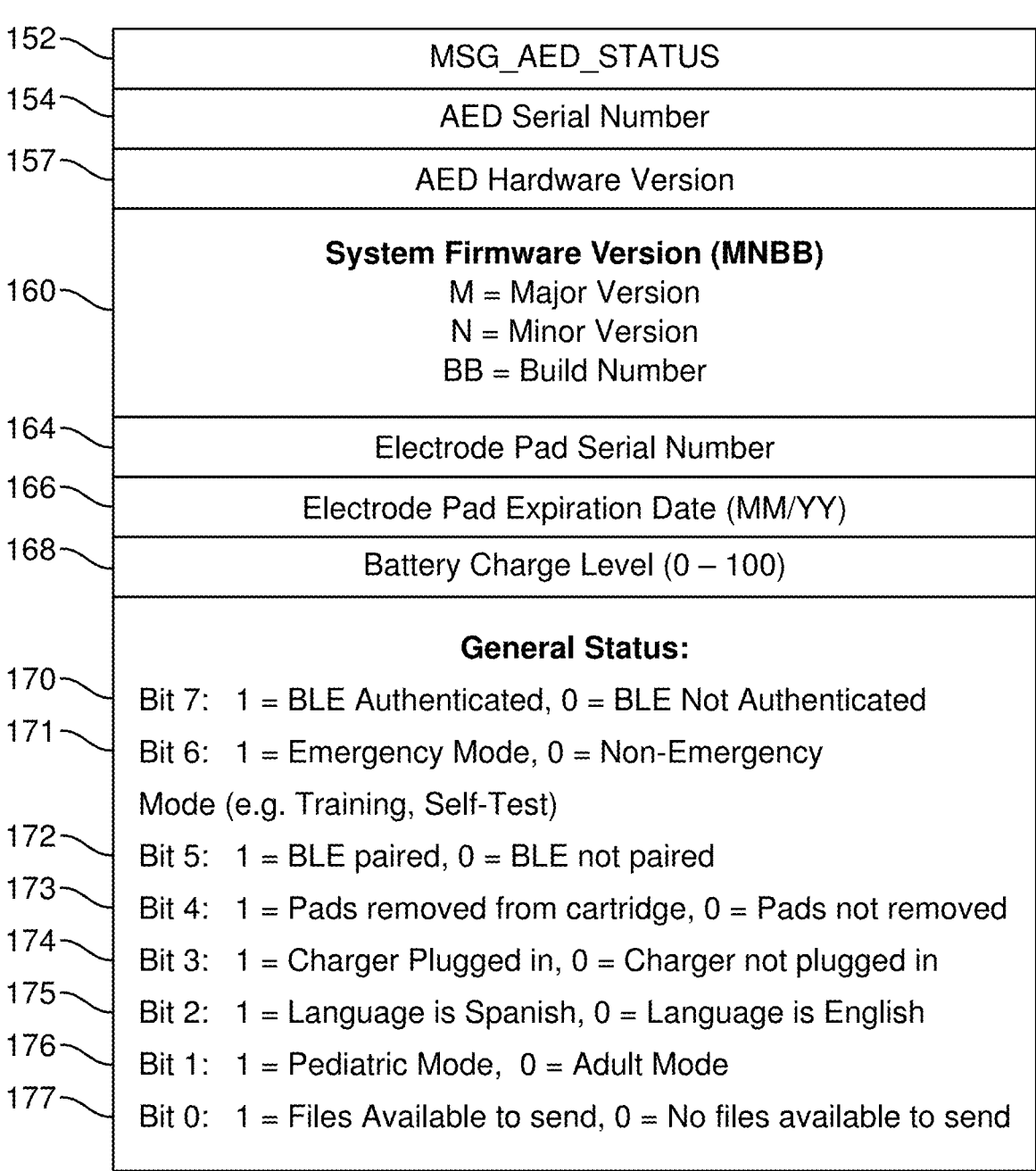

FIG. 2 is a schematic diagram illustrating components of a representative AED status message.

Figure 3:
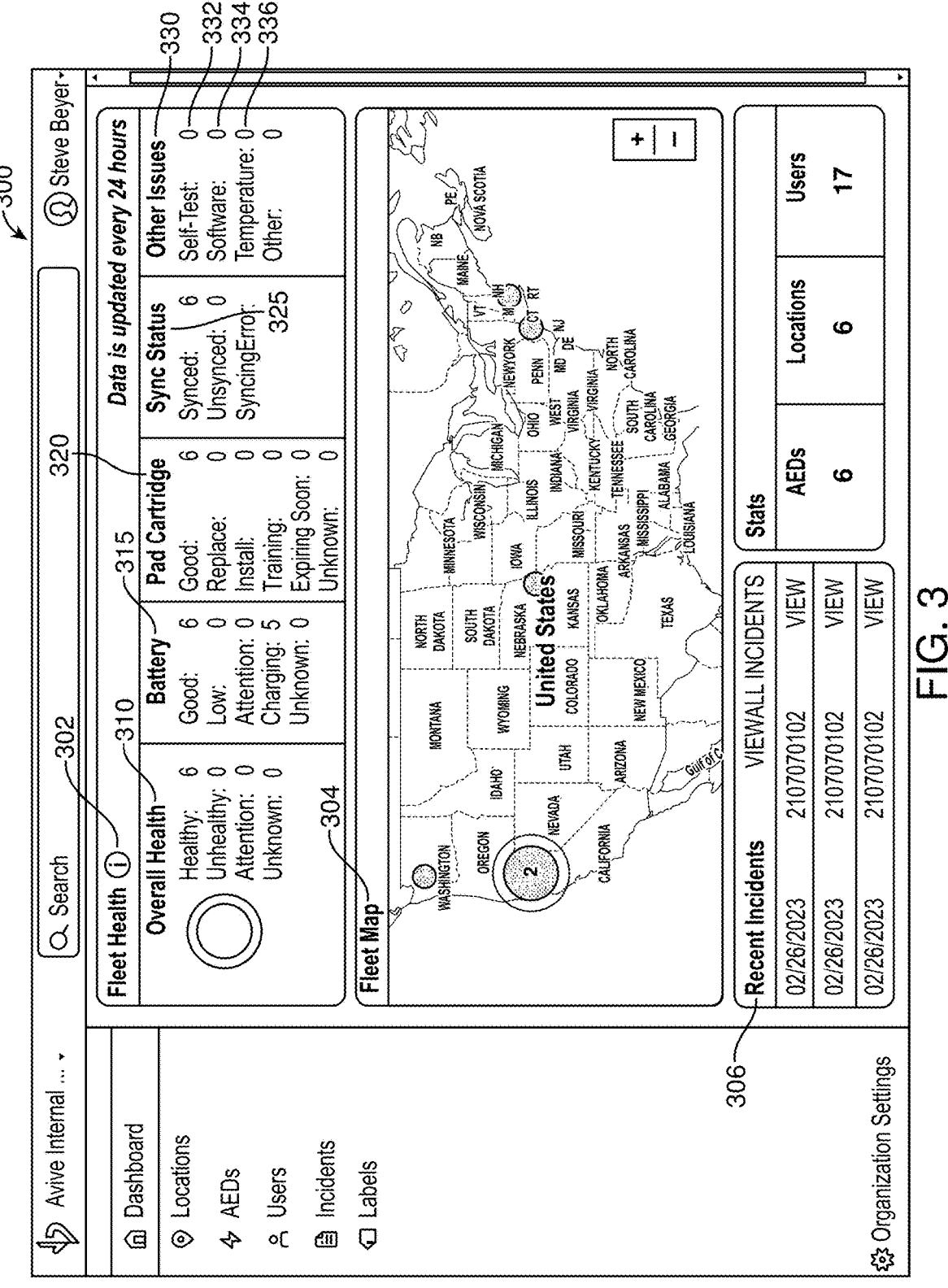

FIG. 3 is a screen shot of a dashboard page of a computer-based management platform user interface in accordance with a first embodiment.

Figure 4:
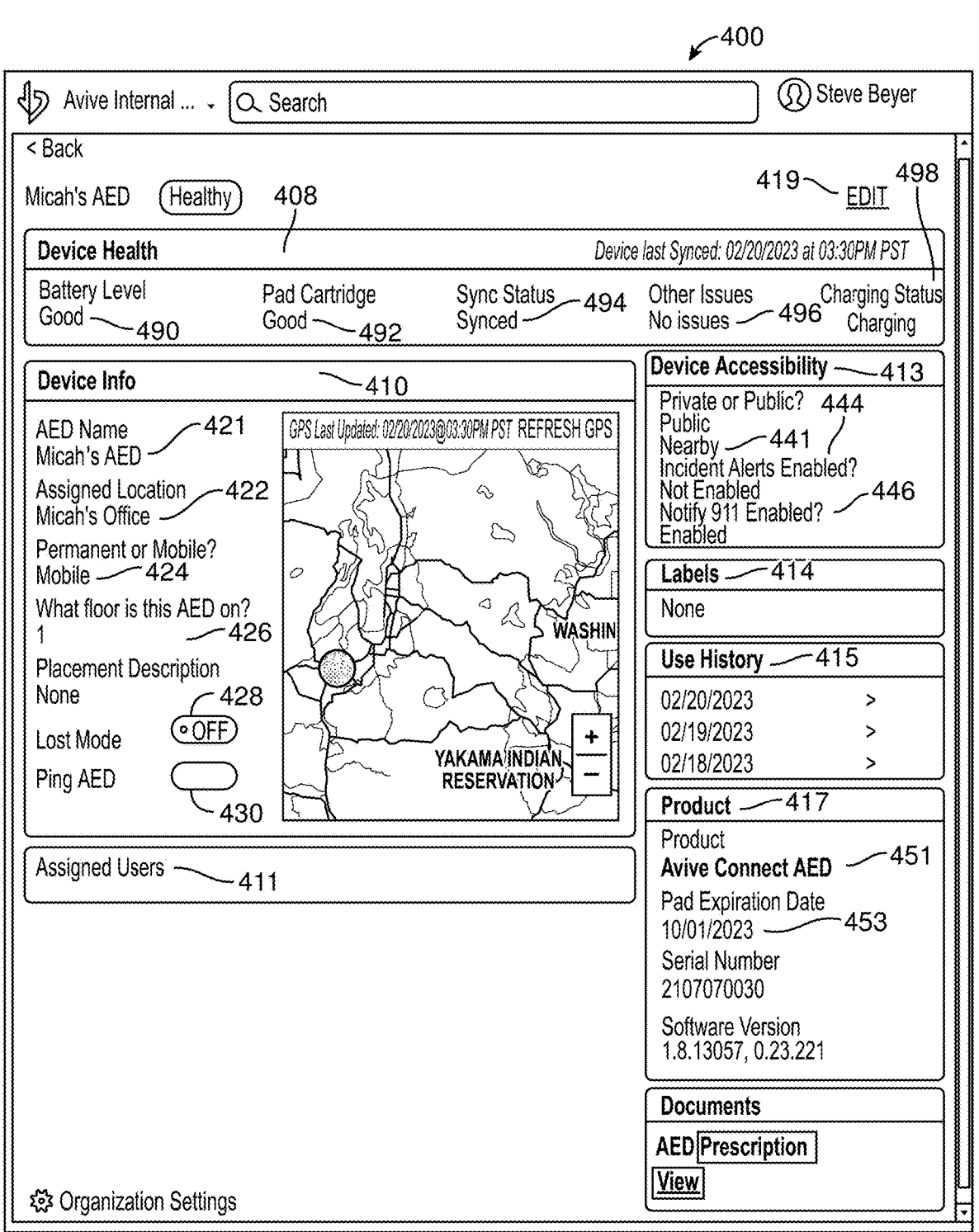

FIG. 4 is a screen shot of a representative AED status page of the management platform user interface.

Figure 5A:
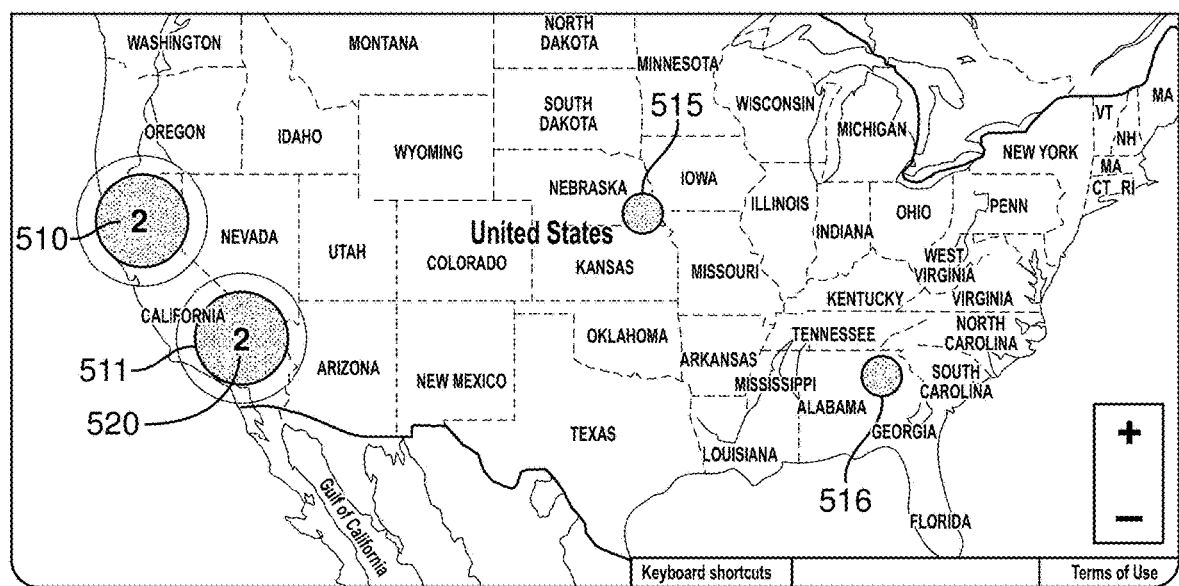

FIG. 5A is a view of a representative fleet map having at least one summary feature.

Figure 5B:
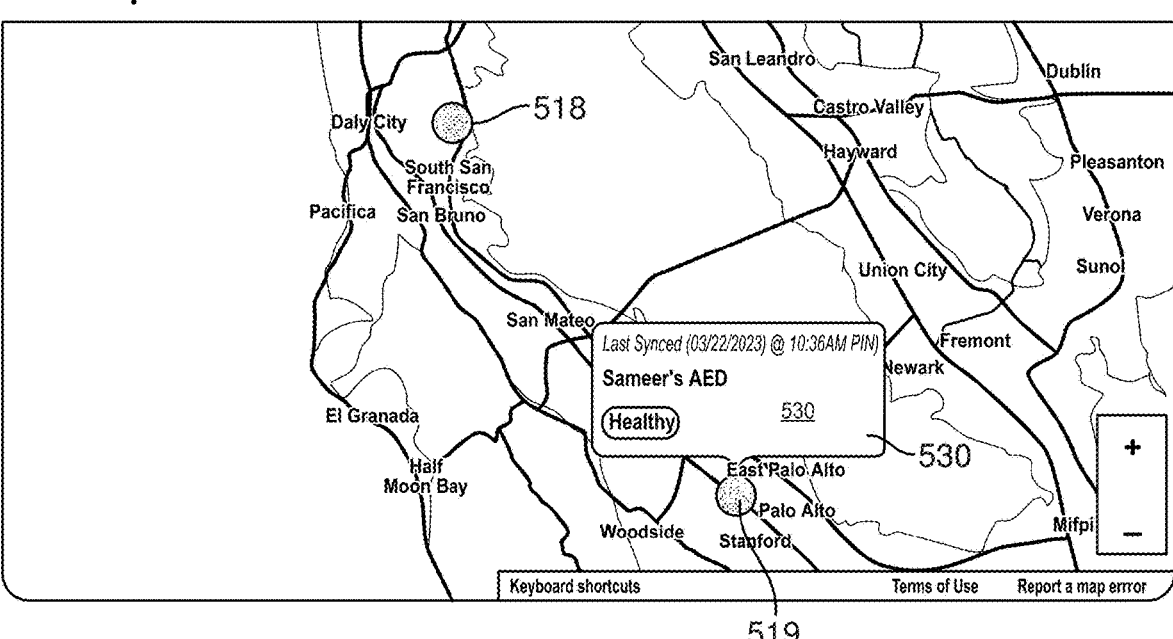

FIG. 5B is a zoomed in view of a portion of the fleet map shown in FIG. 5A.

Figure 6:
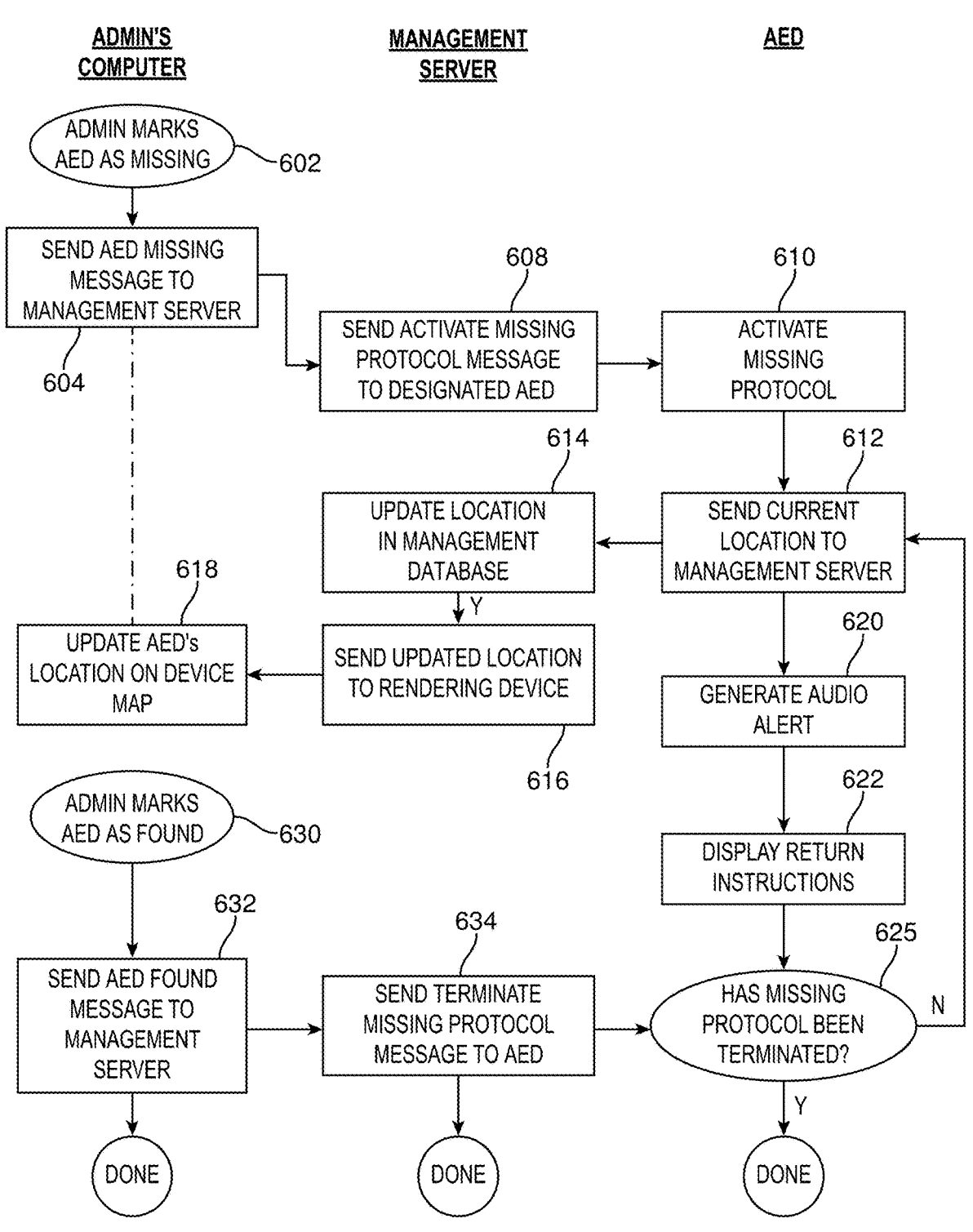

FIG. 6 is a flow chart illustrating a lost/stolen protocol in accordance with an embodiment.

FIGS. 7A-7C are screen shots illustrating a return instructions interface.

Figure 8:
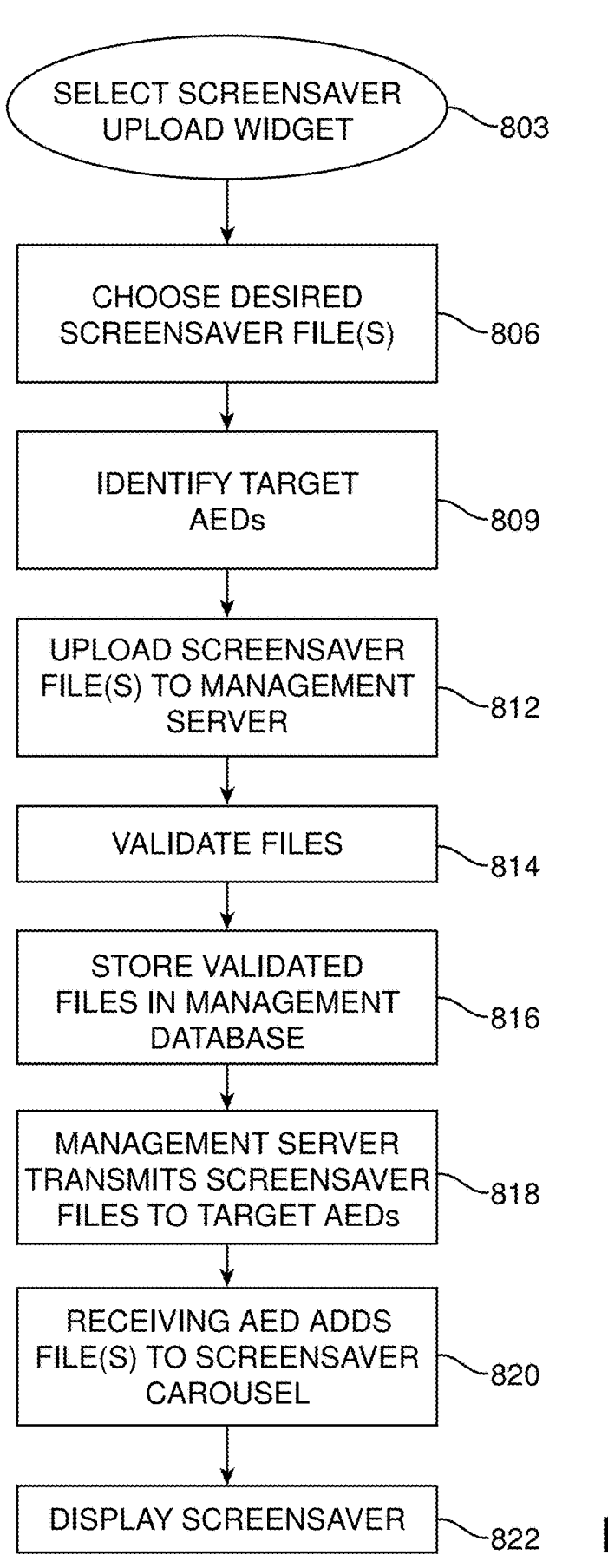

FIG. 8 is a flow chart illustrating a method of uploading screensaver content to selected AEDs.

Figure 9:
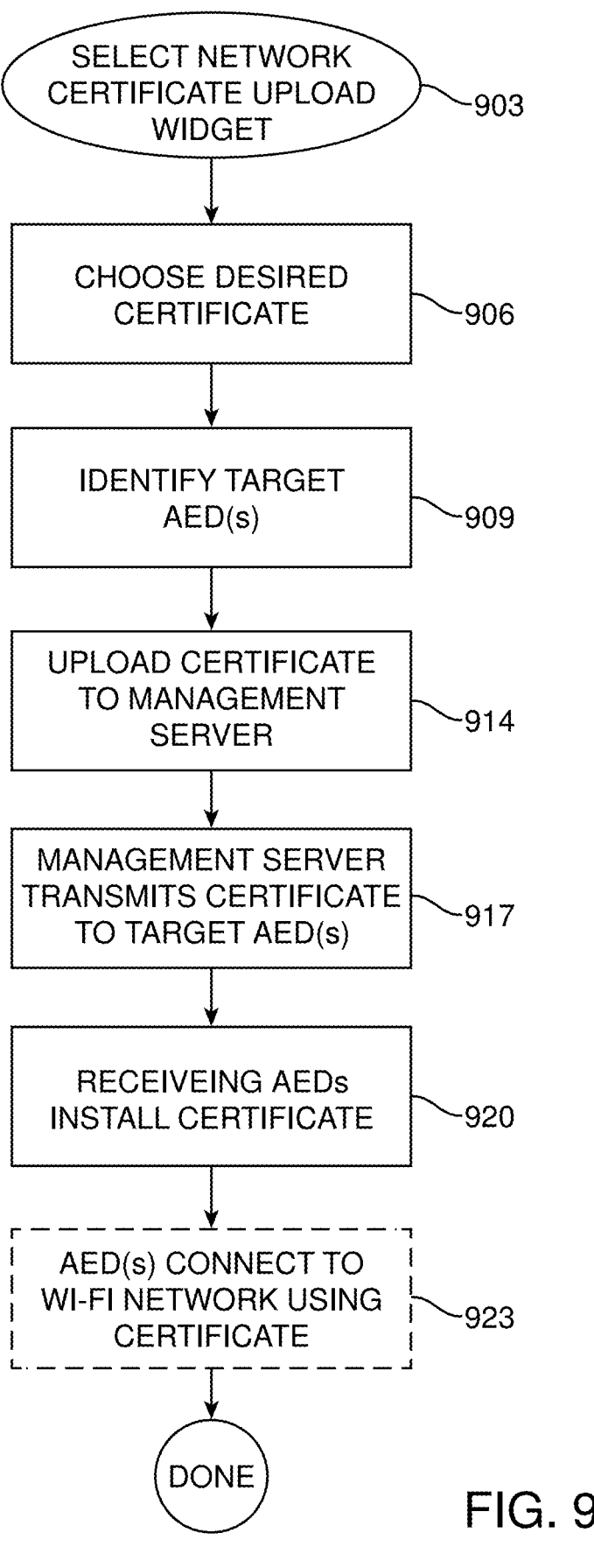

FIG. 9 is a flow chart illustrating a method of uploading a network certificate to selected AEDs.

FIG. 10 shows selected sections of a representative Incident Report.

Figure 11:
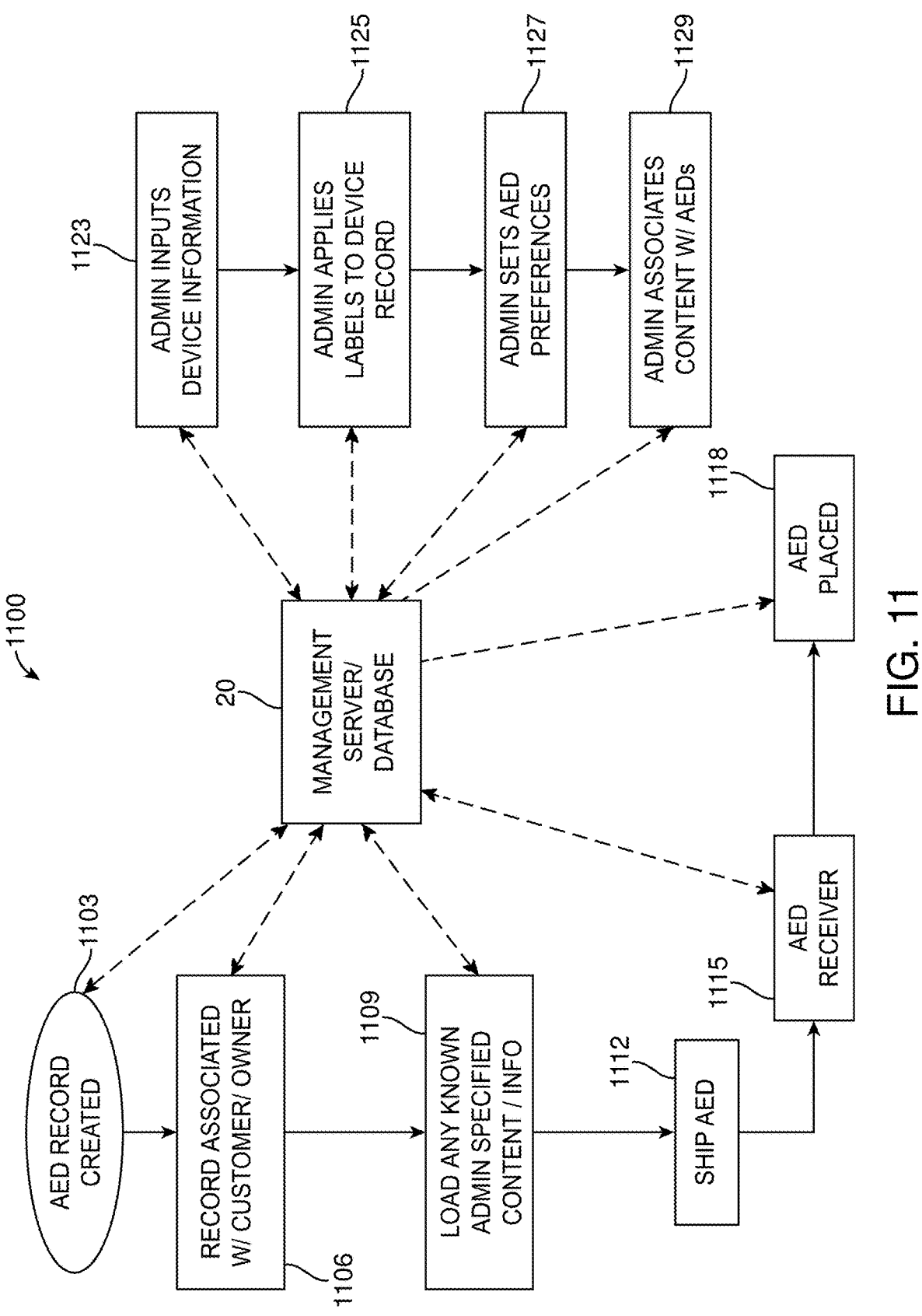

FIG. 11 is a flow chart illustrating a representative AED configuration and setup process.

Figure 12:
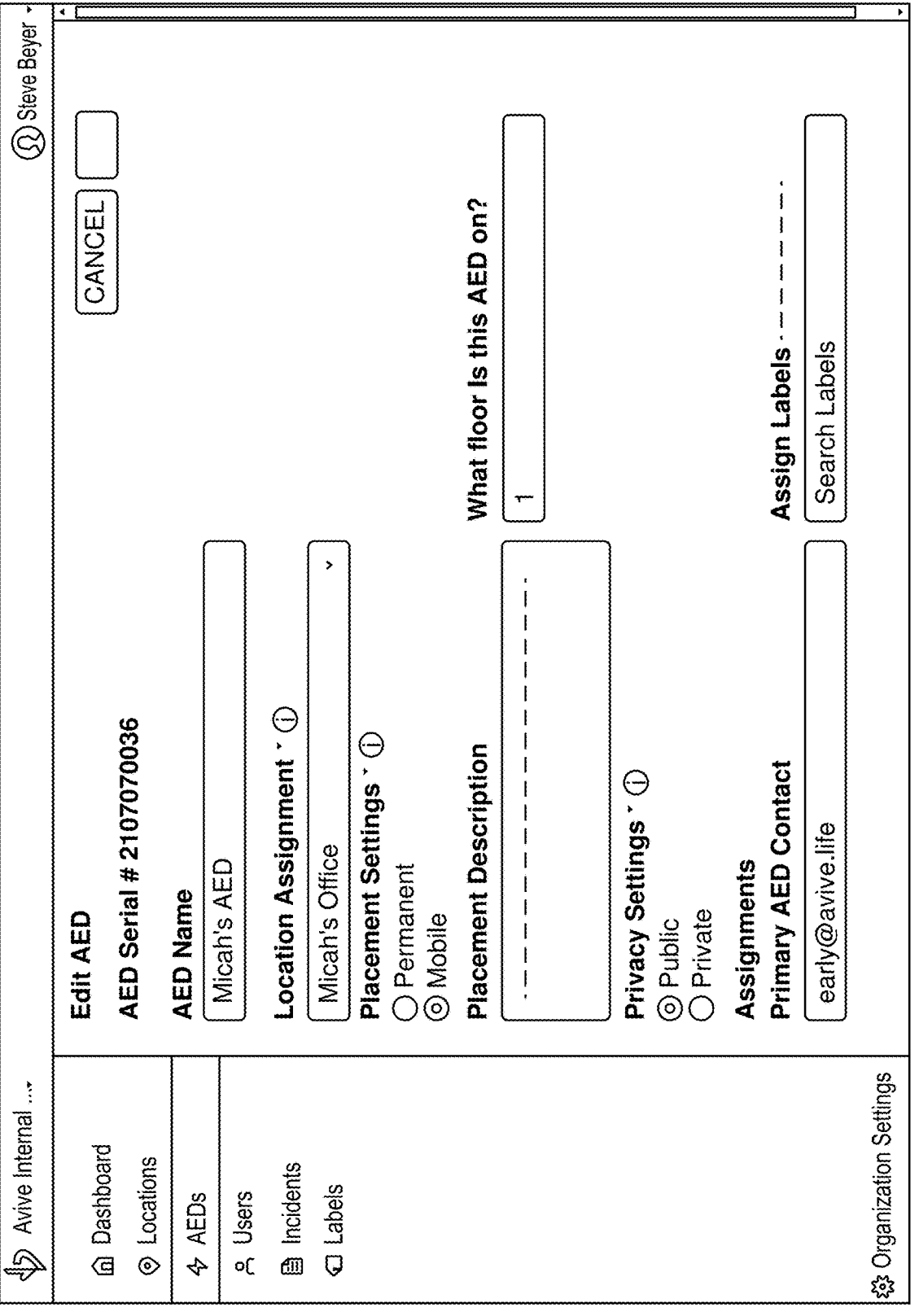

FIG. 12 is a screen shot illustrating a representative edit AED record dialog box.

Figure 13A:
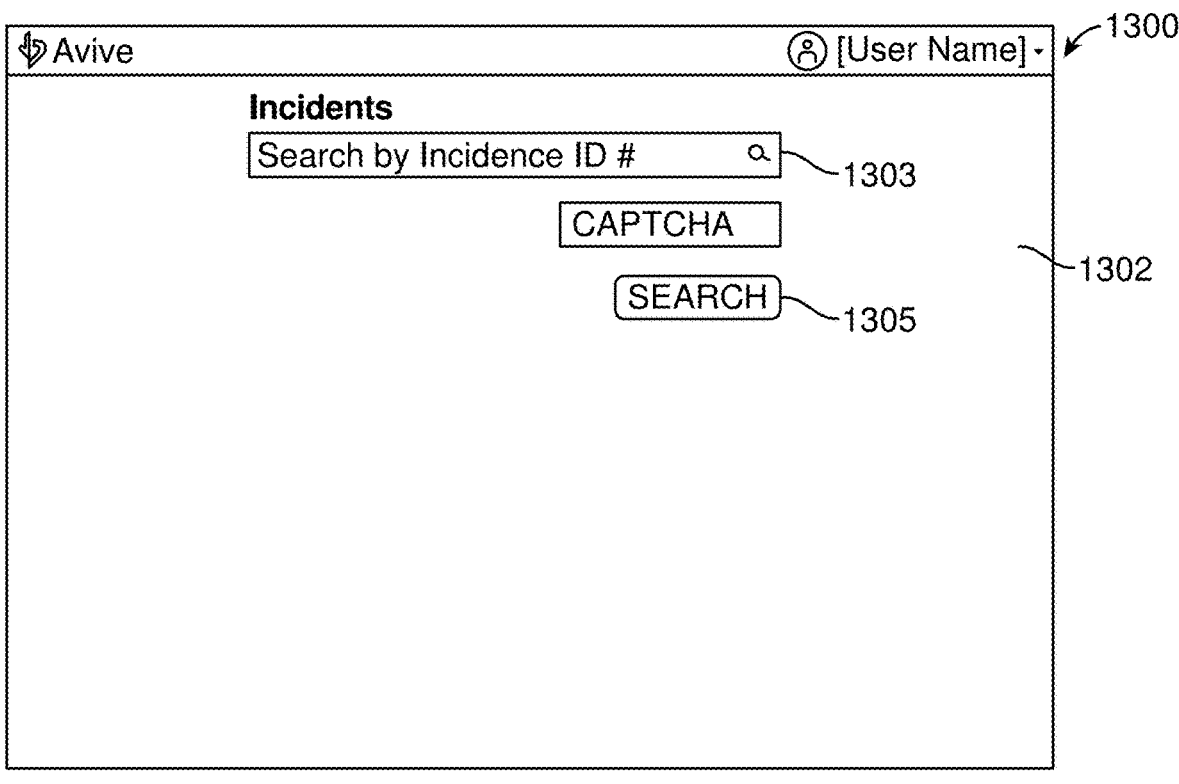
Figure 13B:
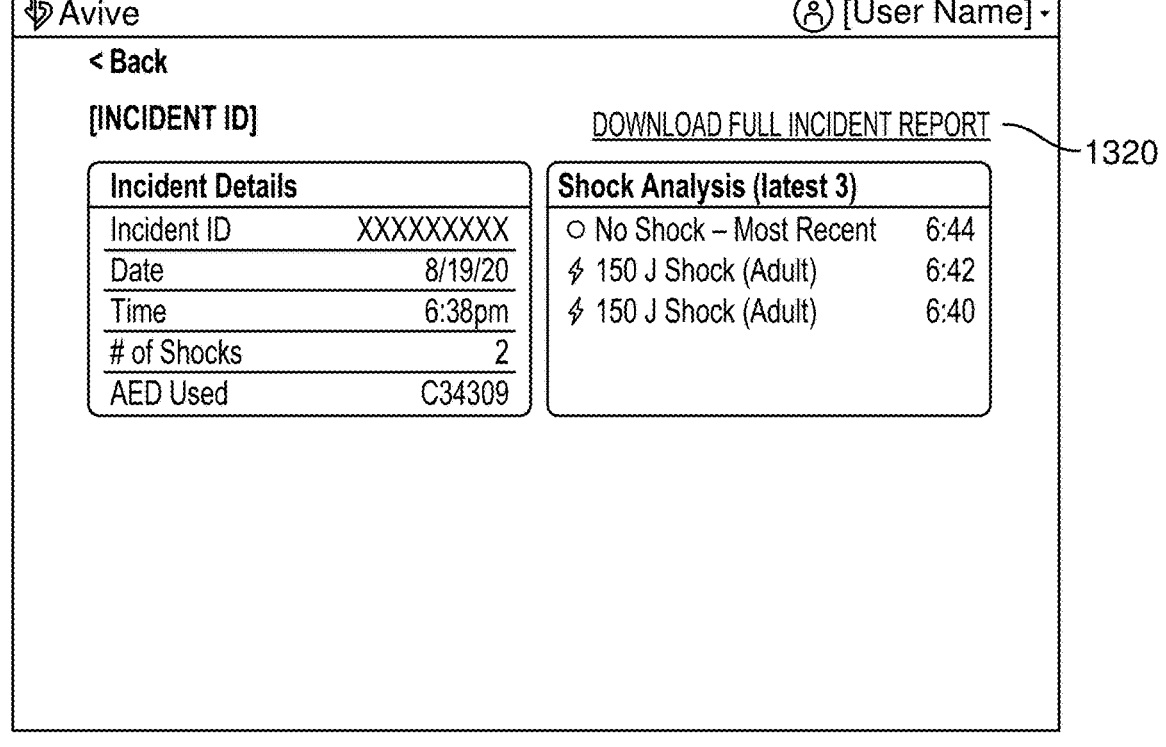

FIG. 13A is a screen shot of an incident query page of an incident report portal in accordance with one embodiment. FIG. 13B is a screen shot of an incident summary page from the portal.

FIGS. 14A-14E are a series of screen shots illustrating a Wi-Fi Selection widget.

Figure 15:
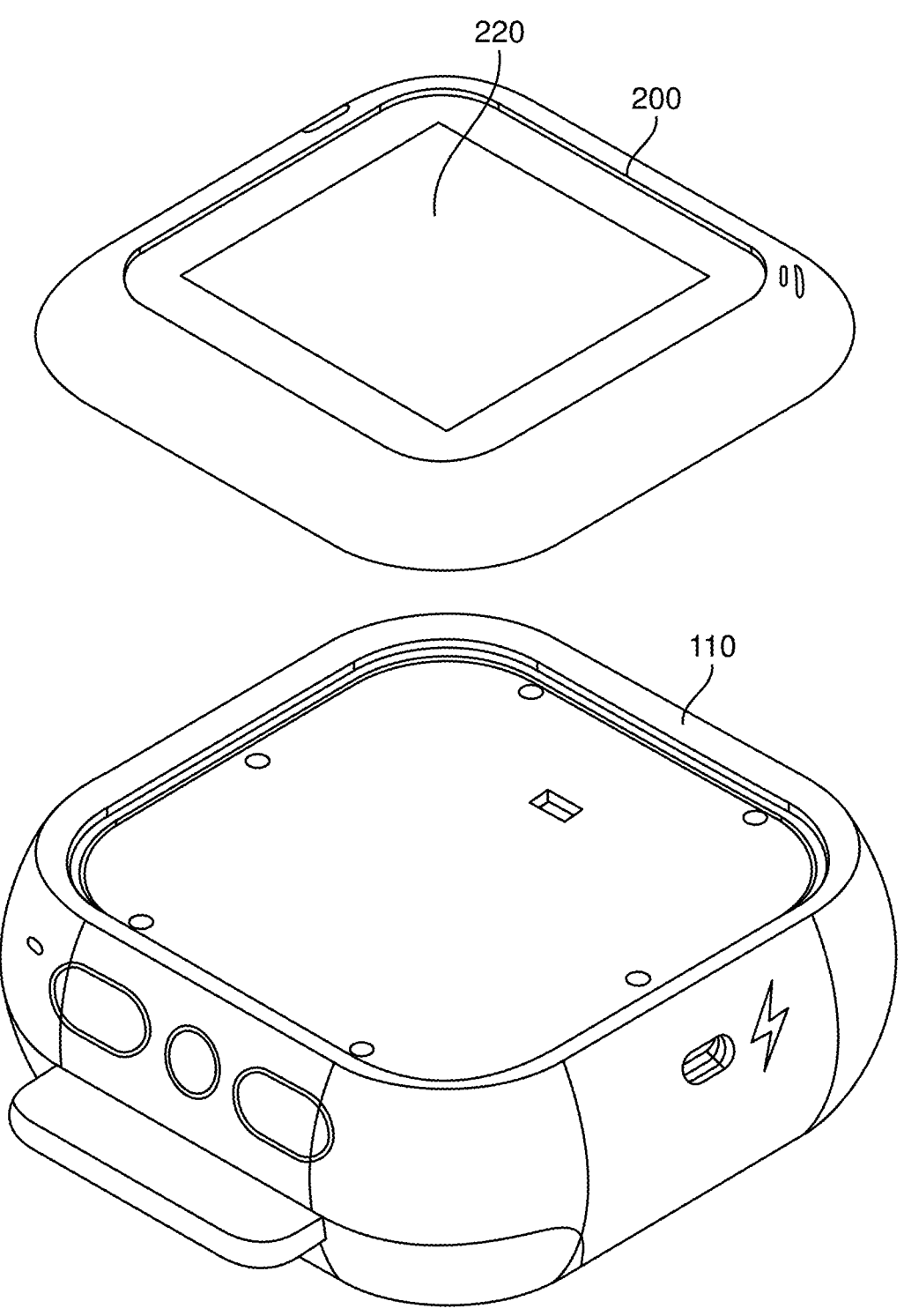

FIG. 15 is a diagrammatic representation of a modular defibrillator system architecture in accordance with one embodiment.

Figure 16:
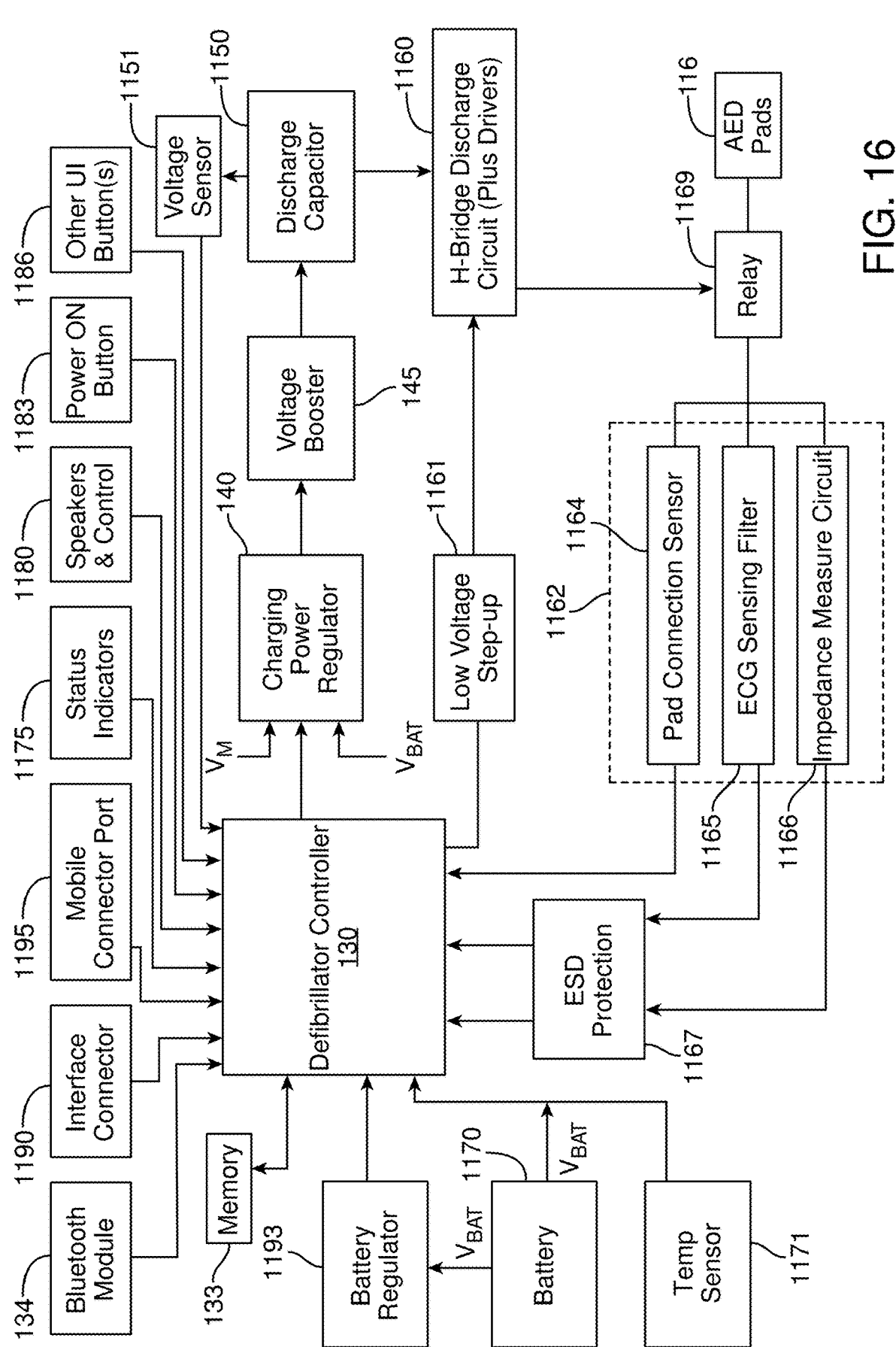

FIG. 16 is a block diagram illustrating electrical components of a representative base defibrillator unit.

Figure 17:
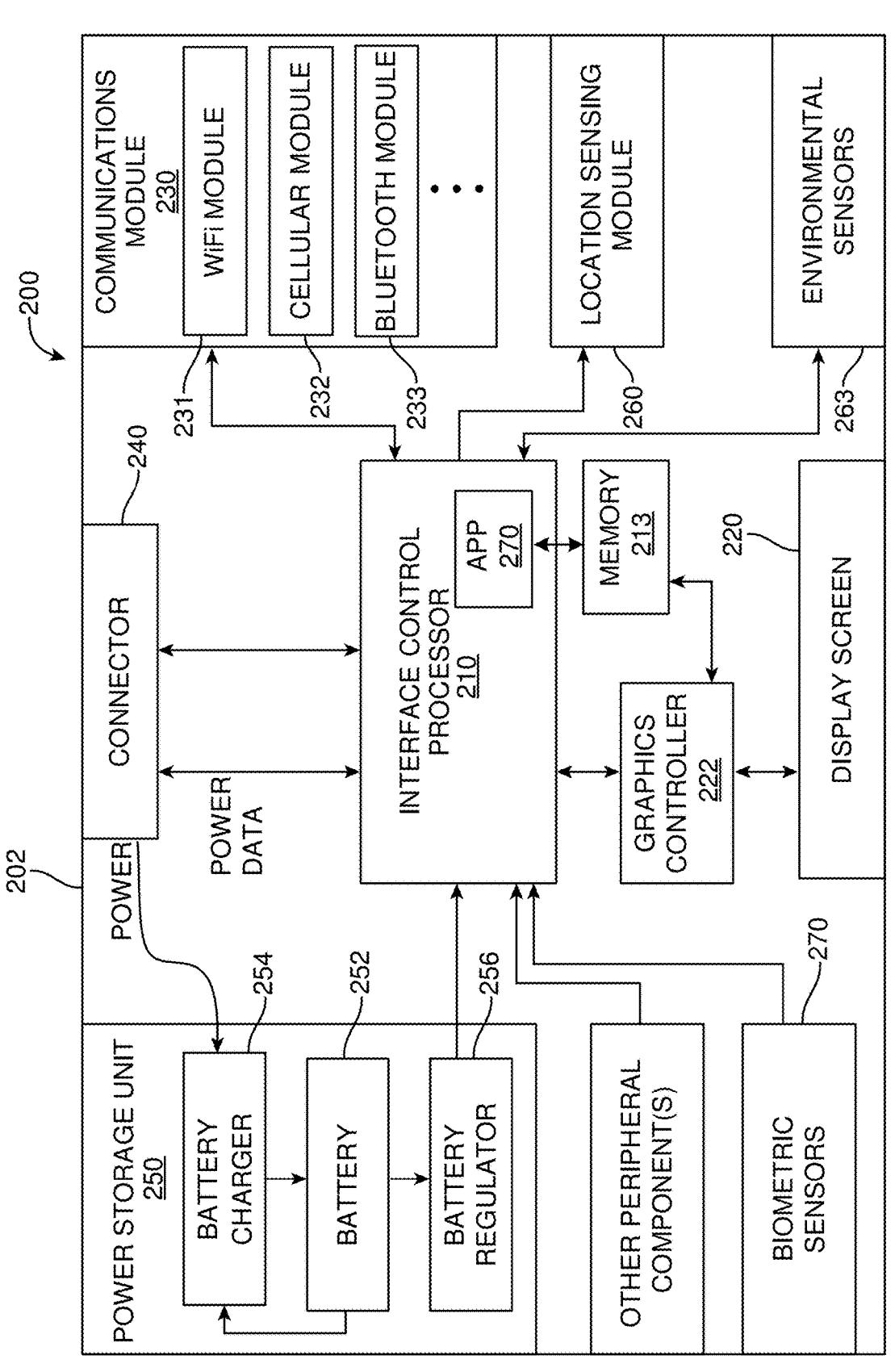

FIG. 17 is a block diagram illustrating electrical components of a representative interface unit.

Figure 18:
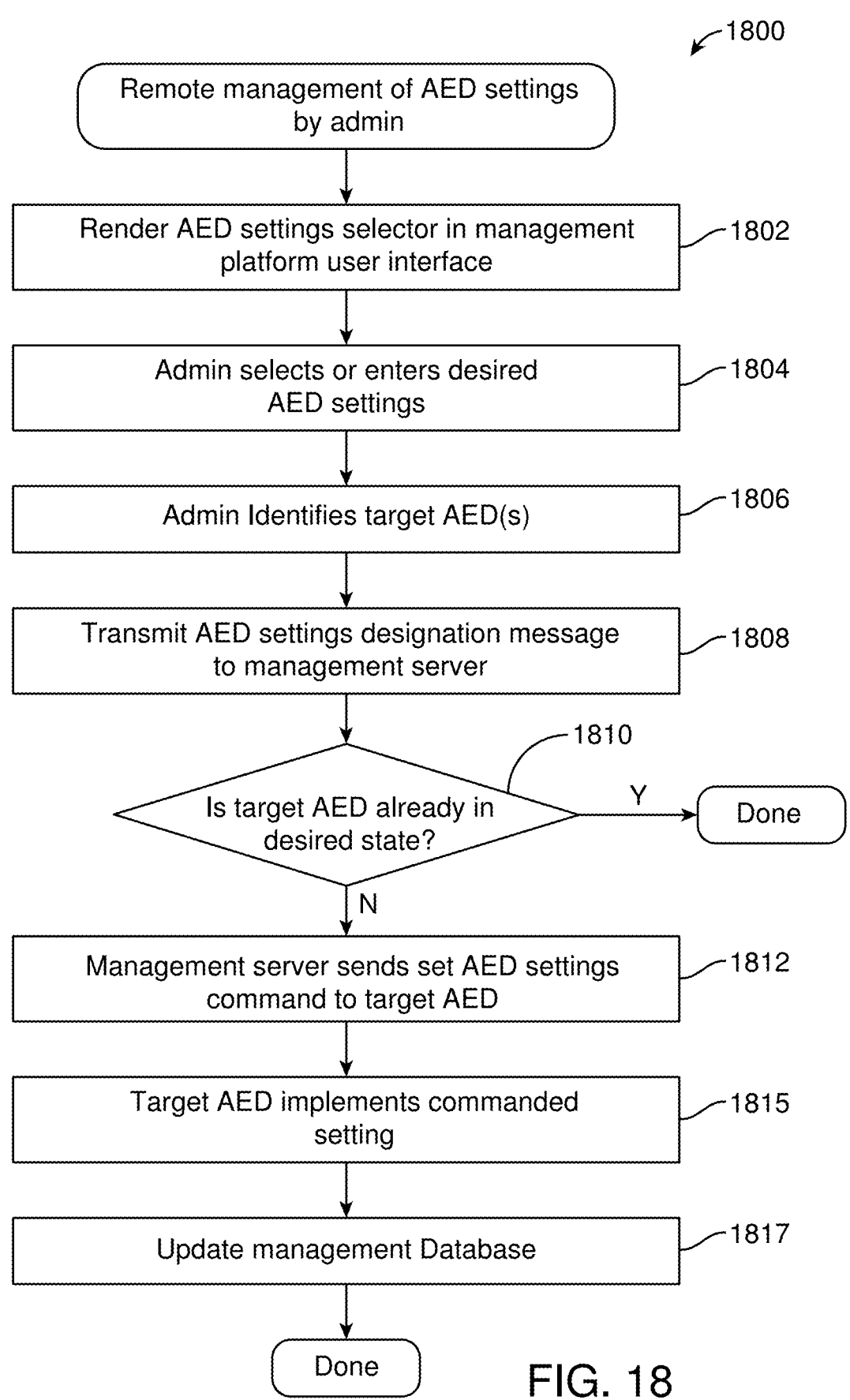

FIG. 18 is a flow chart illustrating a method of facilitating remote administrator management of AED settings in accordance with an embodiment.

Figure 19:
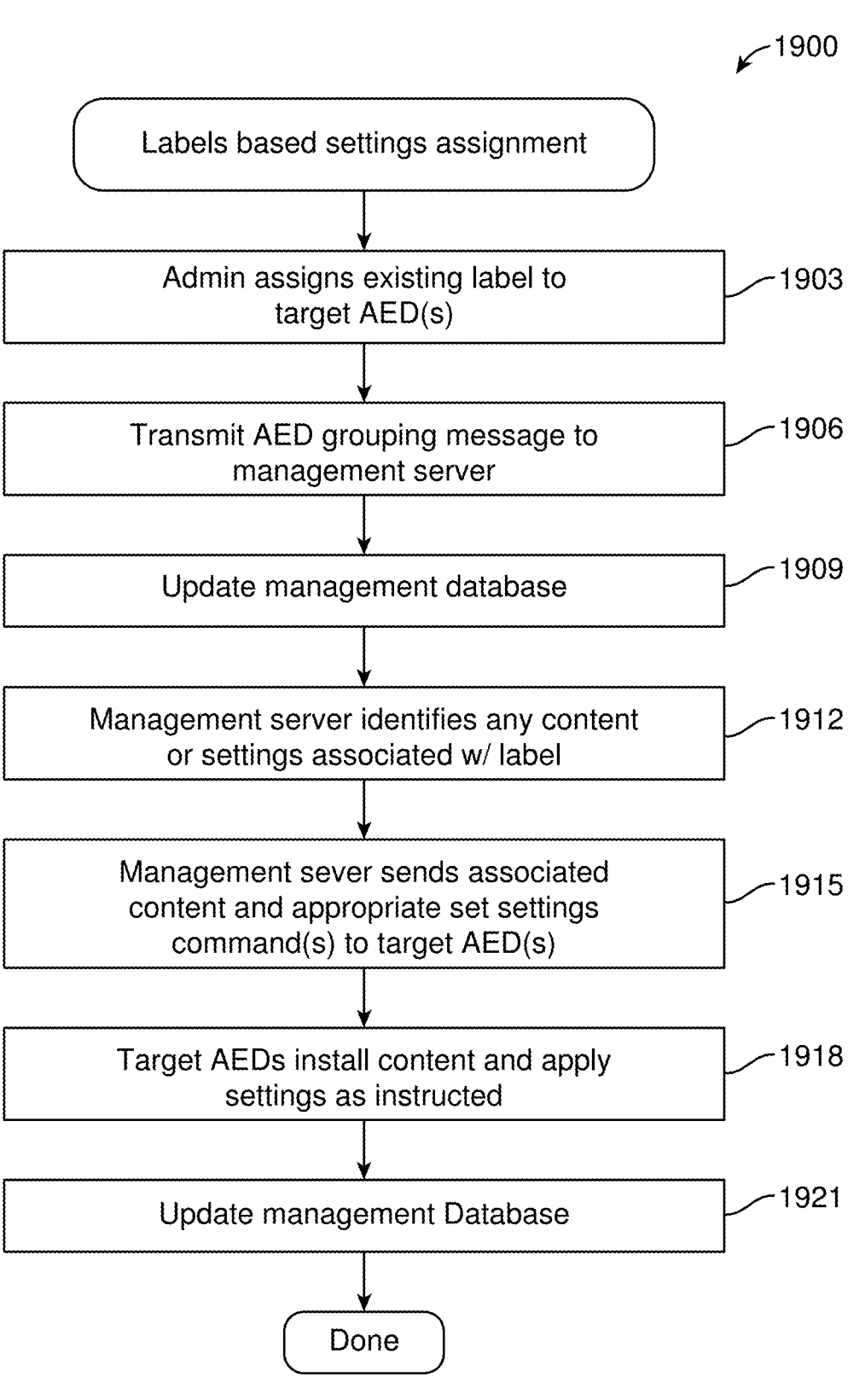

FIG. 19 is a flow chart illustrating a labels-based method of facilitating remote administrator management of AED settings and content through the use of labels in accordance with one embodiment.

In the drawings, like reference numerals are sometimes used to designate like structural elements. It should also be appreciated that the depictions in the figures are diagrammatic and not to scale.

DETAILED DESCRIPTION

The present disclosure relates generally to medical device management platforms, such as automated external defibrillator (AED) management platforms. The disclosure also describes systems, management platform graphical user interfaces, management server infrastructures, connected automated external defibrillators (AEDs), and protocols for communications between such system/devices that make it easier for owners, administrator, and others to manage their devices. The present disclosure also describes mechanisms that facilitate getting incident information to interested parties, including medical personnel, EMS personnel and others when an AED is used.

Many of the features described herein are facilitated by having AEDs that are truly "connected" in the sense that they can reliably communicate with a management server infrastructure (and potentially other endpoints) at substantially any time. This includes both when the AEDs are in a standby mode and when they are being used in emergency settings. The Applicant has developed connected automated external defibrillator systems that are well suited for use in conjunction with the described management platform. By way of example, U.S. Pat. No. 10,773,091 (P006E); U.S. Pat. No. 10,737,105 (P006A); U.S. Pat. No. 11,077,312 (P016B); U.S. Pat. No. 11,331,471 (P015A) and U.S. Pat. No. 11,452,881 (P016A); each of which is incorporated herein by reference, describe a few such AEDs.

FIG. 1 diagrammatically illustrates a representative system architecture. The system includes an AED management server infrastructure 20 (often simply referred to as the management server) that is configured to communicate with a multiplicity of connected AEDs 10. The AED management server infrastructure 20 also serves as a management platform server. As such, it can also be accessed by a variety of computing devices 30 (sometimes referred to as administrator computing devices) that AED owners, administrators and other interested parties can utilize to manage their AEDs. The management server 20 can also communicate with a variety of other systems and devices to provide relevant AED information, as for example, one or more emergency call centers/or more Public Safety Answering Points (PSAPs) (e.g., 911 call centers in the U.S. and Canada, 112 call centers in Europe, 999 call centers in some jurisdictions and other such emergency services call centers) 32, medical personnel or facilities 34 (e.g., doctors, emergency medical technicians, hospitals, etc.), electronic patient care records (EPCR) providers 36, responder networks 38, and other entities/systems (generally represented by 39). Although responder network 38 is shown as a separate entity in FIG. 1, in many embodiments, the AED management server infrastructure 20 also serves as an AED inclusive responder network server.

In the illustrated embodiment, the management server is shown as a single box. It should be appreciated that the functionality of the management server infrastructure can performed by a single physical and/or virtual server, or any number of physical and/or virtual machines working alone, together or in parallel to perform the various described tasks. As such, the term management server should be understood to include one or more physical and/or virtual servers that cooperate to handle the described tasks.

The various nodes illustrated in FIG. 1 (e.g., the AEDs 10, the management server 20, the administrator computing devices 30) can communicate via any suitable communications network, as for example, a global communications network (e.g., the Internet) or other suitable communication networks. In some embodiments, the AEDs 10 include Wi-Fi, cellular and Bluetooth capabilities to facilitate communications with the management server 20 via a variety of paths. This helps ensure that the AEDs can communicate with the management server most any time, including both when they are in a standby mode and when they are being used to treat a potential cardiac arrest victim. In some circumstances, an AED 10 may communicate with the management server by way of an intermediary such as a stand (e.g., a charging stand) or a passing smartphone as diagrammatically represented by the combination of AED (2) and phone 35 in FIG. 1.

The applicant has also described a number of AED inclusive responder networks, responder network integrations, EPCR integrations and AED management platforms. By way of example, U.S. Pat. No. 10,580,280 (P014B); U.S. Pat. No. 10,565,845 (P014A); U.S. Pat. No. 10,957,178 (P014X1); U.S. Pat. No. 11,138,855 (P014AX2); U.S. Pat. No. 11,210,020 (P021); U.S. Pat. No. 11,645,899 (P014X3); U.S. Pat. No. 11,640,755 (P021X1); U.S. Pat. No. 11,869, 338 (P023) and U.S. patents application Ser. No. 17/100,154 (now U.S. Publication No. 2021/0153817) (P020A); Ser. No. 17/100,313 (now U.S. Publication No. 2021/0154487) (P020B); Ser. No. 17/217,738 (P022); and Ser. No. 17/903, 642 (now U.S. Publication No. 2023/0008570) (P025), each of which are incorporated herein by reference, describe a few such systems and integrations.

AED Reported Current Status Information

The AEDs 10 are configured to send status messages directly or indirectly to the management server 20 at regular intervals. Preferably the status messages are sent on the scale of at least once a day or more frequently when in the standby mode and on the scale of every few seconds or more frequently during emergency use. There are a number of pathways by which the status messages may be sent from the AED to the management server. As suggested above, in various embodiments, the AEDs may have cellular, Wi-Fi, Bluetooth, satellite and/or other communications capabilities to facilitate communications with AED management server via appropriate networks, including global communications networks, Wi-Fi networks, cellular networks, satellite-based networks, etc. A variety of different communications protocols can be utilized in connection with the different networks. For example, WebSockets, Server-Sent Events (SSE), MQTT, short polling, long polling and a variety of other suitable techniques can be used. In some embodiments, the AEDs transmit status messages to intermediary devices via short range wireless technologies such as Bluetooth Low Energy (BLE) advertisements. Status messages received by an intermediary device are then forwarded to the management server. The intermediary devices may take a wide variety of forms, as for example, Smartphones, modular interface units such as those described in some of the incorporated patents, or connected stands, other base stations, tablets, etc. There are a number of protocols that can be used for various Wi-Fi, cellular or Bluetooth communications, including, for example, web sockets, server-sent events, MQTT, short and long polling, etc.

In some implementations, the AED may be modular in nature in that it includes a fully functional base AED unit with an attached interface unit that is not required for the base unit to independently function as an automated external defibrillator. In some embodiments, the interface unit includes a display (which may be a touch screen display) and at least some of the aforementioned communications capabilities (e.g., Wi-Fi, cellular, satellite capabilities). In some embodiments, the interface unit is independently powered relative to the base defibrillator unit. In some embodiments, the interface unit also provides location determining services, which be based on any of a variety of technologies including Global Navigation Satellite Systems (GNSS) (e.g., GPS), Wi-Fi positioning, cellular triangulation, assisted GPS, Bluetooth Beacons, Near-Field Communications (NFC) and/or other location determining technologies. The interface unit includes one or more processors that controls the display and other functionality such that in appropriate circumstances, the interface unit can provide communication services and display content without necessarily even waking up the base defibrillator unit. For the purpose of this discussion, these types of interface units are considered a part of the AED. However, the modular nature of the defibrillator system provides a number of advantages that can be useful.

When such an interface unit is used, the interface unit receives status messages from the base defibrillator unit and then forwards the status message to the AED management server via any of the aforementioned routes. In some circumstances an attached interface unit (or a different intermediate unit located close to the AED) may add other relevant information known by the intermediate unit that is useful for the server, as for example the current location of the AED, environmental information such as a measured temperature and/or other sensed information. The location information may include the geolocation including the latitude and longitude coordinates and the altitude/elevation of the AED. The location information may also include location accuracy information such as the Circular Error Probability (CEP) or other measures of the perceived accuracy of the location information. The measured temperature may be a sensed temperature of the device, the ambient temperature, or any other temperature that the interface unit is capable of measuring. Other sensed information may include accelerometer data and/or any medical information that the interface unit is capable of detecting (e.g., blood oxygen levels, ECG measurements, respiration related measurements, etc.). In some embodiments, the interface unit may also report its own status information. Examples of interface unit status information include, the battery charge level of the interface unit battery, an indication of whether the interface unit is currently plugged into a power supply and/or what type of power supply it is connected to, the results of the most recent self-test of the interface unit, whether a screensaver mode is enabled, which training mode is set for the AED, whether each of location services, Bluetooth services, Wi-Fi services and cellular services are enabled or disabled, the interface unit serial number, the interface unit SIM card #, the interface unit software version number, the interface unit FCC ID number(s), the most recent screen state (e.g. what is or has most recently been displayed on the display screen), an interface unit power-on reason (e.g., the device woke up due to an interface unit button press or due to an AED activation, etc.), error codes, log files, etc. It can also include the connection type that is being used (e.g., a cellular or Wi-Fi network, etc.), the MAC address of the interface unit. The interface unit can also report general device information such as whether a base unit's Bluetooth capability is enabled, the power mode that the AED is currently (including charge pack mode).

A few representative status message transmission approaches are described in more detail in some of the incorporated patents and patent application, including, for example U.S. Pat. No. 10,773,091 (P006E); U.S. Pat. No. 11,077,312 (P016B); U.S. Pat. No. 11,210,020 (P021) and U.S. Pat. No. 11,640,755 (P021X1).

The frequency of status message updates may vary based on the systems needs and capabilities of the AEDs involved, but in general, updates of at least once a day and any time the AED determines that a material change has occurred are preferred. In some embodiments and/or circumstances, the updates may be sent substantially continuously (e.g., every few seconds or less) particularly when the AED is in use, or its location or circumstances are changing. By way of example, when the AED is known to be moving in a circumstance where it is on its way to an emergency incident, status update frequencies on the order of every 1-10 seconds are believed to work well. Similarly, when the AED is in use during an emergency, update frequencies on the order of every 1 to 10 seconds are believed to work well. In another example, in circumstances where the AED is broadcasting status messages to any nearby listening devices via a short-range wireless protocol (e.g., Bluetooth Low Energy (BLE) advertisements) broadcast at frequencies on the order of 100 milliseconds to 10 seconds are believed to work well. More frequent updates can also be desirable in circumstances where the temperature of the device has drifted out of a preferred operating temperature range (e.g., the temperature is too hot or too cold).

Automatically sending status messages to the management server any time the AED detects a change in state (and especially a change in a reported state) is a powerful tool for keeping the management server fully up to date on the status of the monitored AEDs, which allows the information presented to administrators in the management platform user interface accurate in real time. Examples of events that trigger the sending of a new status message include one or more of: (i) a determination that the AED has been move at least a designated distance; (ii) when the AED is activated for an emergency use or training use; (iii) when there is a change in internet connection type (e.g., cellular, Wi-Fi, Bluetooth); (iv) any time there is a user input to the device (e.g., when the touch-screen pressed, a menu item selected, a setting changed, a button pushed, etc); (v) Battery charge level changes by at least a designated amount (e.g., X %); (vi) when a Nearby Emergency state changes (e.g. actively needed for emergency vs. no longer needed); (vii) when the AED's power mode changes; (viii) when a software version number changes after a firmware update has been installed; (ix) any Health status change (e.g., temperature out of range, self-test failure, pad cartridge state change, battery state change, etc); any device state change (e.g., lost mode toggle on/off, active nearby emergency on/off, AED emergency on/off). In some embodiments, when the AED is activated for emergency or training use, status messages are sent at frequent intervals (e.g., every few seconds) and/or any time the current instruction state changes so the management platform can track the current state/instruction state of the AED during such emergency or training use.

The form and specific content of the status messages may vary widely in accordance with the needs and design goals of any particular embodiment, the capabilities of the AEDs and the context in which the status messages are sent. For example, in many cases, the status messages sent during emergency use of the AED will typically have at least some different content than status messages sent when the AED is in a standby mode.

In some implementations, a status message sent while the AED is in the standby mode includes at least some of the following information/fields: (1) a device ID that uniquely identifies the AED (e.g., the AED's serial number or other suitable unique identifier); (2) a functionality status indicator that indicates whether the AED is currently in a functional state; (3) a battery status indicator that indicates a current status of the battery, the battery status indicator can optionally be or include one or more of (i) a battery charge level indicator that indicates the current charge level of the AED's internal battery, (ii) a battery state indicator that indicates whether the battery needs to be replaced or recharged, a charging indicator that indicates whether the device is charging, and/or (iv) other appropriate indicators; (4) one or more electrode pads status indicators that provide information about the defibrillation electrode pads currently installed on the AED, as for example, (i) an electrode pads connected/disconnected indicator that indicates whether electrode pads are currently connected to the AED, (ii) an expiration indicator that indicates a pad expiration date or whether the expiration date for the pads has past (i.e., whether the pads have expired), (iii) a pad replacement indicator that indicates whether the electrode pads need to be replaced, (iv) a used flag that indicates when the electrode pads have been used (and therefore need to be replaced) (v) a pad type indicator that indicates the type of pads that are current installed on the AED (e.g., normal pads, training pads, pediatric pads (if the AED uses different pads for adult and pediatric patients), etc.), or (vi) an electrode pad identifier that uniquely identifies the installed pads (such as the pads serial number) from which the pad type and other information can be determined; (5) a self-test results indicator that indicates whether the AED passed or failed its latest self-test; (6) a data available indicator that indicates whether the AED has information available to be uploaded to a management server; (7) a software version indicator that indicates the version number of the software currently installed on the AED; (8) a hardware version indicator that indicates the version number of the hardware; (9) one or more fault indicators such as a temperature fault indicator that indicates whether the AED is experiencing a temperature fault; (10) a location indicator that provides the current location (e.g., GPS location) of the AED; (11) a temperature measured ambient temperature; (12) any network (e.g., Wi-Fi, cellular, etc.) to which the AED is connected. The AED may also be configured to send other informational messages when specific criteria are identified.

In some implementations, multiple temperature fault levels are detected and reported. For example, a first temperature fault may be identified if/when the detected temperature is outside of its designated operating temperature range, and a second temperature fault may be identified if/when the detected temperature is at a level at which the AED is rendered inoperable (which again can be both high and low temperatures). An AED temperature fault message may be transmitted any time a temperature fault is detected, and when multiple fault levels are defined, appropriate temperature fault messages may be transmitted any time that a higher fault level is detected. Similarly, a temperature fault clear message may be transmitted when the temperature returns to the normal operating range such that a temperature fault condition no longer exists. When multiple fault levels are defined, a temperature fault level message may also be sent any time it is determined that the temperature fault level has been reduced.

In another example, a battery charge level change, such as a change from "good" to "low" may trigger a fault message, and a transition from "low" back to "good" may trigger a fault cleared message. In some embodiments, an informational message is generated any time that a different electrode pad cartridge is installed. The installed pads message indicates the type of the newly installed cartridge (e.g., defibrillation electrode pads, training pads, dedicated pediatric pads, etc.) and any other desired information about the installed pads, such as their serial number, expiration date, etc.

In the section above and at other locations in this document, various faults and information messages have been described. Such messages can be dedicated fault or informational messages, or simply updated status messages when the status message includes the corresponding fault indicators or other relevant information.

A few representative status messages are described in the incorporated U.S. Pat. No. 11,077,312 (P016B); U.S. Pat. No. 11,210,020 (P021) and U.S. Pat. No. 11,640,755 (P021X1). Another representative status message structure is illustrated in FIG. 2. In the illustrated embodiment, a status message 150 includes: (i) a message identifier 152, an AED serial number 154, a hardware version identifier 157, a software version number 160, an electrode pad serial number 164, an electrode pad expiration date 166, a battery charge level 168, a series of status flags and indicators 170-178, a series of functionality flags and indicators, 180-187, and a number of indicators and timestamps associated with reporting emergency use of the AED 190-199.

The message identifier 152 identifies the message as a status message. The serial number field 154 indicates the serial number of the reporting AED. The hardware version identifier 157 indicates the hardware version number of the AED. The software version number 160 indicates the software version number that is currently installed on the AED. In some implementations, the software version number also includes the software build number. The electrode pad serial number 164 provides the serial number of the electrode pad or pad cartridge currently installed on the AED. The electrode pad expiration date 166 provides the expiration date of the installed electrode pads. The battery charge level 168 provides the charge level of the AED's battery. In some embodiments, the AED reports the charge level as a percentage.

The functionality status flags and indicators 170-178 provide general information about the AED. The specific flags used in any particular implementation may vary widely, but in the illustrated embodiment, the flags include: (i) a BLE authentication flag 170 that indicates whether or not the AED's Bluetooth Low Energy (BLE) functionality has been authenticated; (ii) an emergency mode flag 171 that indicates whether or not the AED has been activated in an emergency mode; (iii) a BLE paired flag 172 that indicates whether the AED is currently paired with an external device using an BLE connection; (iv) an electrode pad removed flag 173 that indicates whether or not the electrode pads have been removed from the electrode pad cartridge; (v) a charger plugged in flag 174 that indicates whether the AED is currently plugged into a battery charger; (vi) a language flag or indicator 175 that indicates the language currently selected for providing operating instructions (e.g., if English and Spanish are supported by the AED, a first language flag state may indicates that the current operational language is English and a second language flag state indicates that the current operational state is Spanish-if more than two languages are supported, a multi-bit indicator may be used to facilitate unique identification of each supported language; an adult/pediatric operating mode flag 176 that indicates whether the AED is currently in an adult operating mode or a pediatric operating mode; and a files available to send flag 177 that indicates when the AED has files to send to the management server 20.

The functionality flags and indicators, 180-187 provide information about the current functionality of the AED. In the illustrated embodiment, the functionality flags and indicators include a temperature fault indicator 180 that indicates whether or not the AED is currently within its current operating temperature range. In some embodiments, the temperature fault indicator is a simple flag that indicates whether or not the AED is currently within its designated operating temperature range. In others the actual temperature may be reported or indicators of whether the AED is too hot, too cold, or is far outside of its designated range may be reported as will be discussed in more detail below.

Electrode pad status indicator 182 is a multi-bit indicator that has a number of states which represent different conditions. In the illustrated embodiment: a first state indicates that the pad cartridge is unknown or there is a detection error; a second state indicates that a diagnostic pad cartridge is installed; a third state indicates that a training cartridge is installed, a fourth state indicates that the electrode pads have both expired and been used; a fifth state indicates that the electrode pads have expired, a sixth state indicates that the electrode pads have been used; a seventh state indicates that no electrode pads are connected to the AED; and a seventh state indicates that a functional (unused and unexpired) standard electrode pads are connected to the AED. If a separate pediatric cartridge is available, an eighth state indicates that a pediatric cartridge is attached.

A self-test results flag 184 indicates whether the AED passed or failed its last self-test. A battery low flag 186 indicates whether the AED's battery is low.

The emergency use indicators and timestamps include an activation timestamp 190 that identifies the time that the AED was activated for emergency use. In some embodiments, the combination of the device serial number 154 and the activation timestamp 190 form a unique incident ID for each emergency use.

A shock counter 191 indicates the total number of shocks (if any) that have been delivered as part of the current incident. Classification indicator provides information about the latest patient cardiac rhythm analysis performed by the AED's classifier. The reported information includes (i) a classification timestamp 193 that indicates the time that the classification analysis was performed. (ii) A shockable rhythm flag 194 indicates the classification result—e.g., whether the detected heart rhythm was deemed a shockable rhythm and therefore a shock was delivered, or a non-shockable rhythm was detected. In embodiments in which the classifier identifies the nature of the detected rhythm such information can be included as well. (iii) A shock intensity indicator 195 indicates the intensity of the delivered shock. In implementations in which both adult and pediatric shocks are contemplated and are intended to be delivered with the same energy levels, this may take the form of a flag that indicates whether an adult or pediatric shock was delivered. In embodiments where a wider variety of shock energy levels are expected, a correspondingly larger set of states can be used to convey the delivered energy, or the energy delivered can simply be reported (e.g., 150 joules).

When a shock has been delivered, a shock delivery timestamp 196 may be included to indicate the time that associated shock was actually delivered. In some embodiments, a time since last analysis 197 is also provided. This indicates the amount of time that has passed since the latest reported classification analysis was performed. In some embodiments, the classification indicators for one or more preceding classifications are also included.

Although a specific status message structure has been described, it should be appreciated that the contents of the AED may be configured to transmit a number of different status messages at different times and that the contents of any particular status message may vary widely based on the needs of any particular system and system design goal. Therefore, the description of the status message set forth above should be understood to be exemplary in nature, and a number of other message formats can be used to convey pertinent information to the management server.

Management Platform User Interface

FIGS. 3-5 illustrate a few representative management platform user interfaces in accordance with the present disclosure. FIG. 3 illustrates a representative web-based AED management platform user interface that is particularly well suited for rendering on the displays associated with desktop, laptop, and other relatively larger screened computing devices. The illustrated user interface takes the form of a dashboard screen 300 (e.g., a web page) in an AED management platform that allows a user (e.g., an administrator) to quickly see an overview of the status of all of the AEDs the administrator is responsible for. In some implementations, the dashboard 300 is the default page that a user sees when they log into the management platform via the web using a large screen device. On smaller screen devices such as Smartphones, the layout of the components would typically be optimized for presentation on the smaller screen regardless of whether the dashboard is rendered in a web-based view or an app-based view.

The illustrated dashboard 300 includes a fleet health section 302 and a fleet map section 304. It may also optionally include other appropriate sections, such as, for example, a recent incidents section 306, reports on fleet health or fleet statistics, training summaries and logs, subscription and/or billing summaries and/or other appropriate sections. The fleet health section 302 is designed to give the user an overview of the status of all AEDs with which they are associated. In the illustrated embodiment, the fleet health section 302 includes an overall fleet health reporting box 310, a fleet battery status reporting box 315, a fleet pad status reporting box 320, a sync status reporting box 325 and an other fleet status items reporting box 330. The overall fleet health reporting box 310 indicates the number of AEDs in the fleet that are currently reported to be in good operational condition (labeled "Healthy"), the number AEDs in the fleet (if any) that are not in a good operating conditions (labeled "Unhealthy"), the number of AEDs in the fleet (if any) that are operational but need attention (labeled "At Risk"), and the number of AEDs in the fleet whose status is currently unknown (labeled "Unknown"). It should be appreciated that looking at the fleet health reporting box 310 can give the user/administrator a quick understanding of whether there are issues with any of the AEDs that they are responsible for or otherwise associated with. When desired, the categories can be color coded to help visually convey their meaning. By way of example, the "Healthy" category (both the label and the number) can be rendered in green, the "Unhealthy" category can be rendered in red, the "At Risk" category can be rendered in yellow, and the "Unknown" category can be rendered in grey.

Battery Status

The fleet battery status reporting box 315 gives the user an overview of the status of the batteries in the AEDs in the fleet. The applicant has developed an AED that utilizes a rechargeable battery. The AEDs (e.g., AEDs 10), report their battery's charge status as part of the periodic status messages sent to the management platform. Therefore, the management platform has knowledge of the actual status of each AEDs battery based on information reported by the AED itself. The battery status reporting box 315 identifies the number of AEDs in the fleet that are currently reporting that their battery is in good operational condition (labeled "Good"), the number of AEDs that are currently reporting that their charge level is low and need to be recharged (labeled "Low"), the number of AEDs that are in a charge condition that could put them at risk (labeled "At Risk") and the number of AEDs (if any) whose current battery status is unknown (labeled "Unknown"). Like the overall fleet health status reporting box, the categories in the fleet battery status reporting box can be color coded to help visually convey their meaning. By way of example, the "Good" category can be rendered in green, the "Low" category rendered in yellow, the "Unknown" category be rendered in grey, and the "At Risk" category rendered in another color. In some embodiments, the fleet battery status reporting box may additionally indicate the number of AEDs in the fleet that are currently plugged into a charger. The meaning of the "At Risk" category may vary based on the needs of the system. For example, in embodiments wherein the AED includes an interface unit that facilitates connectivity and has a separate battery from the base defibrillator unit/medical device (e.g., so that the interface does not draw power from the battery that powers the medical aspects of the AED), the "At Risk" category may indicate that the interface unit battery is low such that connectivity may soon be impaired, but the battery for the medical device is still good. Alternatively, the "At Risk" category may indicate that the AED battery level is so low that certain functionality (e.g., connectivity at a desired level) will be shut down if the battery is not charged very soon.

In some embodiments (not shown) the status of the interface unit batteries may be presented separately from the AED batteries. For example, separate categories for interface battery good, low, at risk, charging, and/or unknown and subsets or variations thereof may be provided in fleet battery status reporting box 315.

In some embodiments, the battery charging status may also be included in the fleet battery status reporting box 315. In the illustrated embodiment, this is reflected by charging indicator 316 which indicates the number of AEDs that are currently plugged into a charger. The battery charging status indicates the number of AEDs that are currently attached to a charger. In some embodiments, a separate indicator indicates the number of AEDs that are not currently attached to a charger.

The battery status information presented in the fleet battery status reporting box 315 is preferably based on battery information automatically provided by the AED itself. This contrasts with conventional management platform which may indicate when a battery needs to be replaced based on information manually entered into the management platform database by an administrator based on an expected expiration date of pads that were installed, or supposed to be installed, on the AED.

If any of the managed AEDs require periodic battery replacement, additional fields can be included that relate to the battery's replacement. For example, a "Replace" category (not shown) may indicate that the battery has passed its expiration date and therefore should be replaced immediately. Similarly, an "Upcoming" category (not shown) may be provided to indicate that the battery should be replaced soon. Like the other described categories these (and any other categories that may be included), are based, at least in part, on information provided by the AED itself—as for example an installed battery cartridge expiration date or serial number in a status message sent by the AED. In such embodiments, the AED preferably reads such information from the installed battery cartridge so that the management platform is known to have accurate information about the cartridge currently installed on the AED.

In some embodiments, an AED may have multiple batteries. For example, in AEDs having a modular architecture with a base defibrillator and a separate interface unit attached thereto (as described, for example, in incorporated U.S. Pat. No. 10,773,091 (P006E)), the interface unit may have a separate battery or in other embodiments, the AED may have a separate battery for its connectivity and screen components, which tend to be relatively large consumers of power when the AED is in its. In such embodiments, more battery states may be shown in the battery status reporting field. For example, the in some embodiments, field like "Connectivity & Screen Battery Good," Connectivity and Screen Battery Low" and/or Connectivity and Screen Battery Dead may be added to show the status of the Interface Unit (sometimes referred to as the Connect Unit or Connectivity and Screen) battery. In another example, when the fleet includes at least some AED connected to battery powered charge pack, the state of the charge pack's battery and/or charge level can be reported in a similar manner. In a specific example, a set of battery status states may include all or some of the following: (i) Battery Good (both good); (ii) Battery At Risk (Connectivity & Screen battery low); (iii) Battery At Risk 2 (Connectivity & Screen Battery Dead); (iv) Battery Low (AED Battery Low); (v) Battery Charging (charger plugged in); (vi) Battery fully charged (plugged in and fully charged); and (vii) Battery dead (AED Battery Dead); and Battery charge level (e.g., an indication of the percentage of a full charge that the battery is current at).

Pad Status

The fleet pad status reporting box 320 (labeled "Pad Cartridge") gives an overview of the status of the defibrillation electrode pads installed in the AEDs in the user's fleet. When the defibrillation pads are part of a pad cartridge, the status may be thought of as reflecting the status of the pad cartridge. In the illustrated embodiment, six distinct categories are identified. The first indicator/counter (labeled "Good") identifies the number of AEDs in the fleet that have defibrillation electrode pads installed that are unused, unexpired, and not in need of replacement and are otherwise believed to be in good condition for use. The second indicator/counter (labeled "Replace") identifies the number of AEDs (if any) that need their electrode pads replaced immediately. The need for replacement could be due to: (i) the installed pads having past their designated expiration date (expired); (ii) the pads having been used but are still installed in the AED instead of being replaced; or (iii) for any other appropriate reason. The third indicator/counter (labeled "Install") identifies the number of AEDs (if any) that don't have any electrode pads installed therein for any reason. One reason that the pads might be missing is that the AED was been used and the pads removed but not replaced. In other circumstances the pads may have been removed but not replaced for other reasons, as for example, someone intended to replace expiring pads with new pads but didn't finish the job.

The fourth indicator/counter, (labeled "Training") indicates the number of AEDs (if any) that have training pads installed therein instead of operable defibrillation electrode pads. Some AEDs are designed to operate in a training mode when training pads are installed. For example, the AED may operate in a standard mode when normal defibrillation electrode pads are attached, and in a training mode when training pads are installed. The defibrillator will not deliver a shock in the training mode, but in other respects will provide a user experience that simulates a real use of the AED. During active training, the training pads should be utilized. However, when the AED is intended to be available for use outside of the training environment, it is important that the training pads be replaced by real defibrillation electrode pads. Separately identifying AEDs that have training pads installed gives the administrator a good visibility as to when training pads are installed and whether they have been replaced by standard defibrillation pads when they are supposed to be. In some circumstances multiple different types of training pads may be available-such as a first training pad set type that supports CPR feedback, a second (more normal) training pad type that does not. In such circumstances, the different types of training pads can be separately reported or reported as subcategories of the training pad category.

The fifth indicator/counter (labeled "Upcoming") identifies the number (if any) of AEDs that are due to have their defibrillation electrode pads replaced in the near future. As will be appreciated by those familiar with AEDs, the defibrillation electrode pads typically need to be replaced periodically. The replacement cycle varies by model, but typical useful lives for defibrillation electrode pads are on the order of 2-5 years from manufacture. The electrode pads are deemed due for replacement when their expiration date is within a designated range of the current date (e.g., within 60 days or 3 months). The window designated as replacements being due can vary based on user or management platform designer preferences, but ranges on the order of 1-6 months are believed to work well.

The sixth indicator/counter (labeled "Unknown") indicates the number (if any) of AEDs whose current electrode pad status is unknown.

In another specific example, a set of pad states may include some or all of the following: (i) Good pad cartridge meaning that the installed pad cartridge is in good order; (ii) Install pad cartridge—meaning that no cartridge is currently installed on the AED so one needs to be installed; (iii)—Expired pad cartridge—meaning that the installed cartridge is past its use-by date; (iv) Used Pad cartridge—meaning that the installed pad cartridge has been used on patient and therefore must be replaced; (v) Training pad cartridge—meaning that a training cartridge is currently installed; (vi) Invalid pad cartridge meaning that an unapproved or invalid cartridge is currently installed; and (vii) expiring soon—meaning that the use by date is coming up soon (e.g., in the next 30 or 60 days). The use by date may be based upon the a date associated with the manufacture of the pads (e.g., X years from the date of manufacture) or may be based upon actual testing of the pads, or a combination of both.

Although not shown in FIG. 3, some AEDs are capable of utilizing more than one type of defibrillation electrode pads. In some circumstances, the different types of pads may be based on intended use—e.g., separate adult and pediatric pads. In other circumstances, the different types of pads may be based on different types of functionalities—as for example, graphically responsive defibrillation, vs. "normal" not graphically responsive electrodes, etc. When that is the case, additional indicators/counters can be provided to specifically indicate the number of AEDs that each of the various types of available electrodes.

In a preferred embodiment, the management server automatically determines the status information in the fleet pad status reporting based on information provided by the AEDs. Specifically, in some embodiments, the AED is able configured to read identifying information from a chip on the pads or pad cartridge (or to read other identifying information on the pads/pad cartridge and determine the status based thereon). A variety of information can be used in such determinations, as for example, the serial number of the installed pads or pad cartridge, a pad expiration date and/or a pad type. By way of example, U.S. Pat. No. 11,266,826 (P015B) and U.S. Pat. No. 11,331,471 (P015A), both of which are incorporated by reference, describe AED and pad cartridge arrangements with such capabilities. The periodic AED status messages sent to the AED management server 20 include the pad information available to the AED. This can include a pad identifier that uniquely identifies the currently installed pads, such as the attached pad cartridge's serial number, the pads expiration date, the pad type, etc. The AED also reports if/when no electrode pads are attached and if/when the installed electrode pads have been used. If the most current information received in a status message from the AED is different than the information then stored in the management database 290, the management database is automatically updated. Therefore, the management server 20 almost always has access to accurate and current information in the management database 290 about exactly what electrode pads are installed on the AED.

If the AED doesn't include the pad expiration date in its status messaged, the management server 20 can look-up the pads' (or pad cartridge's) date of manufacture and expiration date based on the serial number. As such, the management platform knows, or is able to determine if/when the installed pads are expired and need to be replaced (category 2—Replace), are expiring soon (category 5—Upcoming) or are training pads (category 4—Training). Similarly, the management platform is automatically informed if/when no pads are currently installed on the AED (category 3—Install) or the installed pads have been used and therefore need to be replaced (category 2—Replace). When the fleet health summary 302 is rendered, the current information is provided in the dashboard thereby giving the administrator a current/accurate view of about the status of the electrode pads currently installed in the fleet of AEDs that they are responsible for.

Basing the pad status reported to the administrator via the management platform on installed pad information provided by the AED itself helps eliminate or mitigate a number of common AED management problems. For example, in conventional systems, the pad expiration date is manually entered into the AEDs record. This, of course, is more susceptible to user input errors. Worse, some management platforms are updated when the pads are shipped to a customer or sent to a location-without any verification that the new pads were actually installed as intended.

As previously mentioned, in some embodiments, the AED 10 is configured to send a status message to the management server any time there is a change in a reported state of the AED. This includes changes like the electrode pads (or electrode pad cartridge) being disconnected/removed; a cartridge (different or not) being installed, electrode pads being removed from a pad cartridge, etc. This allows the electrode pad status information presented in the management platform user interface to be accurate in real time, which is very helpful from a fleet, or individual AED management perspective.

In some embodiments, the management server can be configured to send notifications regarding various events to administrators and/or other interested parties. The notifications can be presented in the management platform, or via other conventional messaging technologies such as e-mail, text messages (SMS messages) etc. The messages may be sent in real-time relative to when the pertinent information is received, or at other appropriate times. In some circumstances, such notifications (or notifications of particular types of events) can be provided in periodic reports (e.g., daily, weekly, monthly, etc.) rather than in real-time. This can be helpful for mitigating unnecessary real-time notifications.

Sync Status

As will be known to those familiar with conventional commercially available AEDs, most AEDs do not automatically communicate status information electronically to a management server, and the few that do are typically configured to transmit their status relatively infrequently (e.g., once a month or, at best, once a week). It should be apparent that a lot can change over the course of a month or week, and as such, it can be highly desirable to have status messages sent more frequently so that the management platform has more accurate information about the status of the deployed AEDs. Therefore, in some preferred embodiments, the AEDs 10 are configured to provide updated status message at least once a day.

Regardless of the frequency at which status updates, it can be helpful for the administrator to know that the information it is receiving is "current" in the context of the AED's expected reporting frequency. Stated another way, it can be helpful to know whether each AED is reporting in as expected. As such, in some preferred embodiments, the status information provided by the management platform GUI also indicates whether the management platform has current information on the managed AED(s). In the embodiment illustrated in FIG. 3, this information is reported in the Sync Status reporting box 325. As seen therein, the Sync Status reporting box 325 includes a first counter (labeled "Synched)" the number of AEDs in the fleet that have reported in recently as expected, and a second counter (labeled "Unsynced") that indicates the number of AEDs (if any) that have not reported in as recently as expected. These counters are sometimes referred to collectively as a Sync status indicator 326.

The definition of what constitutes "current" or "synched" in this context may vary based on expected updating resolution of a particular system. For example, when an AED is expected to report in at least once a day (which is preferred), the management server may designate its information as stale (not synchronized) if/when the most recent status report it received from the AED is more than 50 hours old. When the AED is expected to report in at more frequent intervals, the acceptable gap between status messages may be shortened accordingly (as for example an hour delay if the AED is expected to send status messages at intervals of 10 minutes or less or substantially continuously). It should be apparent that the delay that triggers the management server to determine that it does not have "current" information (i.e., is not synchronized) can be widely varied based on management expectations. For example, if the AED is expected to automatically report its status only once every 30 days, the trigger for an AED being designated as not synchronized would need to be more than 30 days. Although reporting synchronization status can be useful even when the reporting intervals are relatively long, we believe that more frequent reporting is highly beneficial and that providing lack of synchronization trigger times 50 hours or less can be highly useful in giving administrators confidence that they have a good and accurate view of the status of the AED(s) that they are responsible for.

In some embodiments, the status messages sent by an AED may include a timestamp indicating the time that the status message is relevant for (e.g., the time at which the status information was last updated) or was actually sent by the AED. For example, the AED may be configured to wake up and run a self-test daily, update its status information pursuant to the self-test and then try to automatically send an updated status message from the AED to the management server shortly thereafter. In such circumstances the most current information in the status report may be based on the time that the self-test was run (e.g., confirming that the AED is still in good working order). As such, in some implementations, it may be desirable that the timestamp in the periodic status message include a timestamp indicating the time of the self-test on which the status message is based was executed. In circumstances where a status message or other notification from the AED is based on another trigger (such as a status message sent during an emergency use of the AED, or the detection of a temperature fault or the movement of an AED), the timestamp may reflect the timing of the triggering action. In other embodiments, the timestamp may simply reflect the time that the message is sent by the AED or some other event indicative of the time the status information was last updated or verified.

In other implementations, it may be sufficient to utilize the time that a message is received by the management server as the time used in determining whether the management server has current information. Such an approach works well when the AED (or a communications unit associated with the AED) establishes a connection with the server to transmit the status messages to the server. However, when the messages are conveyed via paths that can potentially incur non-trivial delivery delays (as described, for example, in incorporated U.S. Pat. No. 11,077,312), it is beneficial to utilize a transmission timestamp or an information update timestamp so that the server can verify that a received status message contains the most recently available information.

Other Fleet Status Reporting Items

The fleet health section 302 of dashboard 300 also includes an "Other" fleet status items reporting box 330 (labeled "Other Issues"). The other fleet status reporting box separately calls out a few specific issues, faults, or circumstances that defibrillators in the fleet may be experiencing which the management platform is aware of. In the illustrated embodiment, the first field is a Self-Test failure counter field 332 that identifies how many (if any) of the administrator's AEDs have failed their most recent self-test and therefore need maintenance. The second field in the other fleet status items reporting box 330 is outdated software version counter 334 (labeled "Software"). The outdated software version counter 334 identifies the number (if any) of the AEDs in the managed fleet that do not have the most recent software version installed thereon (i.e., don't have the software version that is desired for that particular AED installed thereon).

It will be appreciated that most modern AEDs are configured to periodically run a self-test to verify that they are still in good working order. Self-tests may be run daily or at other desired intervals. As described above, in preferred embodiments, the AED will report its most recent self-test results including any self-test faults to the management server. By way of example, the AED may be configured to send a status message (e.g., one of the periodic status messages described above) in response to the completion of each self-test. If the self-test results status has changed (e.g., from pass to fail or vice versa), the management server 20 will update the management database 290 accordingly. When the fleet health dashboard 302 is rendered, the management server identifies the number of the user's AEDs (if any) that have failed their most recent self-test via the self-test fault counter 332. As such, the Self-Test fault counter will quickly inform the administrator whether any (and how many) of their managed AEDs have failed their most recent self-test and are in need of maintenance.

In some embodiments, selecting the self-test fault counter activates a link that will cause a dialog box or separate page to be rendered that provides more detailed information about the self-test fault conditions, and/or provides recommendations about how to address the fault. When a single AED is indicated by the self-test fault counter, selection of the self-test fault counter may cause the corresponding AED status page 400 to be rendered and the more detailed information about the self-test fault condition is provided on the rendered AED status page.

Software Update Status

The second field in the other fleet status items reporting box 330 is outdated software version counter 334 (labeled "Software"). The outdated software version counter 334 identifies the number (if any) of the AEDs in the managed fleet that do not have the most recent/most desired software version installed thereon. Preferably, each of the AEDs is configured to periodically report the version number of the software currently installed thereon. For example, in some embodiments, the periodic status messages include a software version indicator that identifies the software version that is currently installed on the AED. In parallel, the management server knows what software version is supposed to be installed on each AED and can verify that the proper software version is installed on the AED. When the software version installed on any particular AED is not the desired version, then the management server identifies that AED as having an outdated software version. This can be accomplished by setting an outdated software version flag in the management database 290. When the fleet health dashboard 302 is rendered, the management server identifies the number of the user's AEDs that do not have the most recent software version (as appropriate for those specific units) via the outdated software version counter 334.

Preferably, over-the-air software updates are automatically provided to the AEDs by the management server if/when it is determined that the AED has outdated software (as for example due to a software update being available). If the software update is provided and successfully installed, the outdated software version flag would be cleared automatically once the AED reports that it is running the new software version. As such the outdated software version counter gives the administrator a good overview of whether the appropriate software version is currently installed and running on all of their AEDs. If there are any problems or delays in getting the latest update installed, the dashboard gives the administrator good visibility as to the issue(s) and the administrator can act accordingly.

In some implementations it may be deemed desirable to have updates occur over Wi-Fi networks rather than cellular or satellite networks. This can be due to the data costs associated with providing the updates, the time taken to deliver the updates or for other reasons. In such embodiments, the management platform server 20 may implement staged efforts to deliver the updates. For example, if/when Wi-Fi is the preferred delivery mechanism, the management server may initially only enable Wi-Fi based downloads of the available software update(s). Note that this distinction is readily made by the management server 20 when a connection request for an AED/interface unit and/or the status message received from the AED/interface unit is configured to indicate the type of connection that is being utilized by the AED (e.g., a Wi-Fi connection, a cellular connection, etc.).

If the update hasn't been delivered to the AED within a first designated period of time (e.g., a week), the management server may send a message to the AEDs administrator suggesting that they connect to Wi-Fi for best results in installing a software update. If/when the AED is thereafter connected to a Wi-Fi network and a Wi-Fi based connection is made to the management server, the software update may be delivered via the Wi-Fi connection as desired. Alternatively, if the software update still hasn't been delivered after a second designated period of time (e.g., a second week), the update may be delivered over the cellular network.

Temperature Based Faults

The third field in the other fleet status items reporting box 330 is temperature fault counter 336 (labeled "Temperature"). By way of background, AEDs typically have a designated operating temperature range. If the AED's temperature falls below or rises above that temperature range, the AED's performance may be degraded, and in some circumstances that AED may simply no longer function as intended. In some embodiments, the AED 10 is configured to sense temperature and to automatically generate a temperature fault if/when its sensed temperature falls outside its designated operating temperature range. The temperature fault is then conveyed to the management server, as for example, as part of a status message or as a separate temperature fault message. Preferably the temperature fault is conveyed to the management server as soon as the temperature fault is detected. That is, if an AED is configured to report its status once a day, the AED would not wait until the next scheduled periodic status message is sent to report the temperature fault. Rather, a temperature fault message is preferably immediately conveyed to the AED management server 20 when the temperature fault is identified. In systems in which multiple fault levels are defined, temperature fault messages are also preferably sent any time a higher-level temperature fault is detected as well.

When the management server receives notification of a temperature fault, it preferably immediately sends a notification to the AED's responsible owner(s)/administrator(s) (e.g., a text notification, an e-mail notification, etc.) warning them of the fault so that actions can be taken to address the situation (e.g., move the AED to a more suitable location, or otherwise address the temperature issue, if practical). In parallel the management database 290 is updated so that the temperature fault can be identified in the relevant status summaries provided in the management platform GUI.

The AED 20 is also preferably configured to automatically inform the management server if/when its temperature comes back within its designated operating temperature range. When the status messages are configured to include temperature faults, this can take the form of simply sending an updated status message. Alternatively, a separate temperature fault cleared message can be transmitted. Like when temperature faults are detected, an appropriate message conveying that the temperature fault has cleared is preferably sent to the management server as soon as the temperature is back within its operating temperature range (or the temperature moves to a lower temperature fault level range) rather than waiting for the next periodic status message. When the management server receives an indication that the temperature fault has cleared (or a lower temperature fault level has been attained), the management database 290 is updated to reflect the current status. In parallel, a notification may be sent to the AEDs owner/administrator to indicate that the temperature fault has been cleared (or that the lower temperature fault level has been attained).

As suggested above, the temperature fault and temperature fault clear messages sent by the AED to the management server can be: (1) dedicated temperature fault and temperature fault clear messages, (2) identified in a more general status message that is triggered by detection of the temperature fault or the determination that the temperature fault is no longer a concern; or (3) any other suitable form. The format of the temperature faults and temperature fault clear messages may take any suitable form. By way of example, in some embodiments, the temperature status may be reflected by a simple flag in the status messages (e.g., a flag that is high when a fault is detected and low when no fault is detected). When multiple fault levels are detected, then a corresponding number of flags can be used, or a multi-bit indicator may be used that defines multiple possible states. For example, a 2-bit temperature fault indicator may have a first state that corresponds to a level one high temperature fault, a second state that corresponds to a level two high temperature fault, a third state that corresponds to a low temperature fault and a fourth state that corresponds to a second level low temperature fault. In another example, the temperature fault and temperature fault clear messages may simply report the detected temperature and the management server may interpret the reported temperature as a temperature fault or temperature fault clear based on the reported temperature.

Any time the fleet health dashboard 302 is rendered, the management server identifies the number of the user's AEDs that are currently experiencing a temperature fault via the temperature fault counter 336. Similarly, any time a status page for a particular AED is rendered while the AED is experiencing a temperature fault, the status page will show that temperature fault.

Although specific temperature fault indicators have been shown, it should be appreciated that the GUI elements used to convey the AED's temperature status can vary widely and when desired, more detailed logs of the temperature faults may also be made available to the owners/administrators. Such logs may provide information such as the time each temperature fault was identified and cleared, one or more actual temperatures detected by the AED and optionally timestamps associate with such temperature measurements.

It should be appreciated that the described temperature fault detection and clearance approach effectively gives the AED's administrator(s) the ability to verify in real time whether their AED(s) is/are within their designated operating temperature range. Faults and fault clearances are also logged so that the administrator has a good record of any issues that the AED has experienced.

In the discussion fleet health status above, a common factor is that the information presented is based largely on information automatically provided by the AED itself in a timeframe that can is considered timely. The AED status message is sent to the management server 20 which tracks the current status of each of the managed AEDs in the management database 290. If new information received from the AED is different than the information currently stored in the database, the database is updated accordingly.

When a user accesses the management platform dashboard, the management server 20 queries the management database 290 to obtain the relevant status information to be provided in the dashboard. The management server then serves the dashboard/dashboard status information to the user device. As such, the status information presented in the dashboard is provided in real time by the management server and reflects "current" status information provided by the AED itself. Although a number of specific types of information have been shown and described, it should be appreciated that the user interface can readily be modified to show any other types of status information provided by the AED in substantially the same manner.

Rendering Counters

In the embodiment shown in FIG. 3, the other fleet status items reporting box 330 has several counters (issue types) that show whether/how many AEDs in the administrator's fleet have specific issues (e.g., self-test failures, software update required, temperature faults, etc.). In some embodiments, some or all of these counters may be persistent in that they are rendered even when the associated count is zero. However, in other embodiments, such counters may be rendered only when one or more of the associated AEDs has that specific issue. Thus, in the context of the other fleet status items reporting box 330, if no associated AEDs have failed a self-test, then the Self-test counter 332 would not be rendered. If none of the associated AEDs require a software update, then the Software Update counter 334 would not be rendered, and so on. The same approach can be used with respect to counters rendered in any of the other reporting boxes (e.g., overall fleet health reporting box 310, fleet battery status reporting box 315, fleet pad status reporting box 320, sync status reporting box 325, etc. Conversely, if any of the associated AEDs have other conditions deemed worthy of identifying to the administrator, appropriate counters may be rendered to in the appropriate reporting box either persistently or when relevant to identify other conditions of interest.

As suggested earlier, in some embodiments, selecting a particular indicator or counter causes the interface to render a dialog box or separate page that provides an indication of the specific AED(s) that have the corresponding issue and more information about the condition(s) that triggered the issue and/or how to address the issue. For example, if a particular counter show that one of the AEDs in the fleet has a particular condition, selecting that counter may cause the corresponding AED status page 400 to be rendered and more detailed information about the condition is provided on the rendered AED status page. In another embodiment, clicking on the counter causes a troubleshooting pop-up to be rendered with instructions and/or video and/or other media to demonstrate how to troubleshoot the issue.

When the counter (issue type) shows that more than one AED has a particular issue, selecting the counter may cause the interface to show or provide a list that identifies the specific AEDs that are currently in the identified state. In another embodiment, clicking on the counter or issue type will filter the fleet map to only display the AEDs in the fleet that have that type of issue, and then clicking on the map icon will take you to the AED Detail Page 400.

Although not shown in the view of FIG. 3, another state that may be shown in the other fleet status reporting box may be "Settings Pending" which indicates that an administrator originated request has been made to change selected device settings, (e.g., power mode, screensaver on/off, training mode scenario, etc. as discussed below) but that the settings change has not yet been implemented by the device. In this situation, the counter shows the number of AEDs for which settings changes have been requested, but not yet implemented. As the settings for the designated AEDs are updated as requested, the counter is updated which provides a powerful feedback tool for the administrator to track the settings changes being updated. When combined with the user interface of showing the relevant AEDs in the fleet map when the administrator clicks on the Settings Pending counter, the administrator can readily see which AEDs have not yet been updated with the desired settings at any time by simply clicking on the Settings Pending counter in the dashboard 300.

Initialization Required

In some embodiments, the other fleet status items reporting box 330 also includes an "Initialization Required" counter (not shown) that appears when one or more of the AED's associated with the administrator has not been initialized and therefore needs to be initialized. By way of background, it is sometimes desirable to deliver an AED to a customer in a shipping mode or other configuration in which it should be initialized when it is received by the customer or is initially placed. In such circumstances, when a record corresponding to an AED is first entered into the management database 290 or at other appropriate times (e.g., when shipped or delivered to a customer), the record may be marked to reflect that the AED requires initialization. When the AED is received by the customer, or at other appropriate times, the AED may be turned on and an initialization protocol may be performed that initializes the AED and renders it ready for use. When an administrator is associated with one or more AEDs that have not yet been initialized, the Initialization Required counter is rendered in the other fleet status items reporting box 330 to indicate the number of the administrator's AEDs that require initialization. When an AED is initialized, the corresponding management database record is updated to show that the AED has been initialized and that AED would no longer trigger the Initialization Required counter.

In Use

In some embodiments, the AED 10 is configured to notify the management server 20 when the AED is in use. This allows the management server to perform several useful functions. (1) In some embodiments, the management server sends real-time notifications, such as text notifications and/or e-mail notifications, to interested personnel (e.g., an administrator or interested person associated with the AED) notifying them that the AED is currently in use. (2) The management server may also send notifications to the PSAP (e.g., a 911 call center in the U.S.) responsible for handling medical emergencies in a region that includes the incident location, as described, for example, in incorporated U.S. Pat. No. 11,640,755 (P021X1). Preferably, the AED sends status messages substantially continuously throughout the incident and notifies the management server when the incident is terminated. Thus, the management server has a good record of what is happening with the AED throughout the incident. This allows the management server to (3) create real-time incident reports and make such incident reports available to interested parties such as administrators, EMS personnel, medical personnel, etc. both during and after the incident as discussed in more detail below. In some embodiments, (4) the other fleet status items reporting box 330 also includes an "AED In Use" counter (not shown) that appears (preferably in a highlighted form) when one or more of the Administrator's AED is actually in use. In other embodiments a banner or other GUI construct can be used to convey that one or more of the viewers AEDs are currently in use. Similarly, the AED status page 400 for any active AED(s) renders a prominent "In Use" Indicator that indicates that the AED is currently in use any time that the AED has been activated for use. The In Use indicator (not shown) may be positioned at any desirable location in the AED status page 400. Although specific locations for the AED In Use counter and the In Use Indicator have been described, it should be appreciated that they or other GUI widgets that inform the viewer that one (or more) of their AEDs is/are currently being used can be rendered at any desired location within the user interface and/or as a banner, pane or other GUI construct that more persistently appears within the interface throughout the incident.

In some embodiments, any/all In Use indicators rendered in the management platform user interface include a link to an incident reporting page that presents an incident report for the ongoing incident. Thus, "clicking on" (or otherwise selecting) the AED In Use counter or the In Use indicator will cause the management platform user interface to render an incident report page that presents an incident report for the ongoing incident. Examples of the content of representative incident reports are discussed below with reference to FIG. 10.

From the standpoint of the management server, one of the challenges of providing notifications of when an AED is in use relates to false positives. That is, undesirably sending "In Use" notifications when the AED is being handled for one reason or another, but is not actually being used. For example, if notifications are sent to Administrators indicating the AED is In Use every time the AED is turned on or a cabinet housing the AED is opened, there will be false notifications when the AED is accessed or turned on for any reason in non-emergency settings. Another approach is to trigger the aforementioned In Use notification features when: (i) the defibrillation electrode pads are accessed (e.g., removed from a pad cartridge or the like); (ii) the defibrillation pads placed (as determined by the detection of the impedance of a patient); or (iii) when a heart rhythm is detected by the AED. In some preferred embodiments, the management server initiates several actions as soon as it is informed/determined that the defibrillation pads have been placed based on the detection of an impedance appropriate for a patient. These include: 1) the text and/or e-mail notification to administrators and interested parties; 2) sending a notification to the appropriate PSAP (e.g., by way of an Emergency Services Interface); 3) making available the real-time Incident Report; 4) providing appropriate notifications in the management platform user interface; and 5) automatically providing the Incident Report or a responding EMT service or a medical facility that the patient will be taken to. Preferably the text/e-mail notifications sent to administrators/interested parties include a link to the Incident—e.g., a URL link to a web page that will render the real time incident report. A similar link is included in the notification sent to the appropriate PSAP. And, as previously mentioned, the In Use indicators within the management platform include similar links to the real-time incident report. In the primary described embodiments, each of these actions is triggered by the detection of a patient impedance. However, in other embodiments, different incident events can be used to trigger some of the different notification pathways.

As mentioned above, in some embodiments, the management server may automatically provide Incident Reports to medical personnel that are, or will be associated with the incident. This can include professional first responders such as EMTs that have been dispatched by a PSAP. This is possible due to the communications between the management server and the PSAP. When the PSAP directly or indirectly informs the management server of the emergency response service that has been dispatched to an incident, the management server may forward the Incident report directly to that service or the dispatched personnel/vehicle. In other embodiments, the management server may transmit the Incident Report to the PSAP, or an Emergency Services Interface (ESI) that serves as an intermediary between the management server and the PSAP. The PSAP or ESI then forwards the Incident Report to the dispatched EMT personnel.

In some embodiments, the Incident Report is also proactively be sent to the hospital or medical facility that the patient will be taken to. In communities that have a single EMS agency or a single hospital/medical facility where cardiac arrest patients are transported to, this is particularly easy to do because all Incident Reports for that community may be sent to the same place. But it is also quite practical in other scenarios since the PSAP and/or the ESI will typically know the facility that the patient will be transferred to so the PSAP or ESI can either inform the management server of the facility that the patient will be transported to, or can themselves forward the Incident Report to such facilities.

Fleet Map

The fleet map section 304 of dashboard 300 includes a fleet map 360 with location markers or other indicia rendered thereon to show the locations of the AEDs that the user is responsible for that are within the region displayed on the map. Various aspects of the fleet map 360 will be discussed with reference to FIGS. 5A and 5B. Preferably, the user can zoom in or out on the map and can move the map's field of view as desired. Conventional map navigation GUI constructs are provided to facilitate such interactions. The map includers locations markers 510-519 that show the general location of the user's AEDs. In the illustrated embodiment, the locations markers take the form of dots, although icons or other indicia can be used as well.

A few aspects of the location markers are worth noting. When multiple AEDs are located relatively close to each other in the context of the scale that the map is rendered at, they may be denoted by a single marker, which we refer to herein as a composite marker. In the view of FIG. 5 markers 510 and 511 are composite markers. Other location markers, as for example, markers 515 and 516, each represent a single AED. The number of composite location markers and individual location markers rendered in any view will depend in large part on how many AEDs are represented in that particular view and how close some of those may be grouped in the context of the scale of the rendered map view. Preferably, there are readily noticeable visual distinctions that differentiate individual and composite location markers. The differences may be size, shape, pictorial representations, or other suitable visual distinctions. In the embodiment shown in FIG. 5A, the distinction is size.

The composite markers (e.g., composite marker 510) each include a counter 520 that indicates the number of AEDs that are represented by that marker. Based on the counter, it can be seen that composite marker 510 represents two AEDs. Of course, the number of AEDs identified by the counter will vary based on the number of AEDs in the area represented by the location marker.

In some embodiments, the color of the markers indicates the health status of the associated AED. For example, a marker that is colored green may indicate that the represented AED is in good working order (healthy), a red marker may indicate that the represented AED is not in good working order (unhealthy) and a yellow marker may indicate that the represented AED is operational but needs attention. For composite markers, the color may represent the lowest status of the represented AEDs. For example, if any of the represented AEDs are considered unhealthy, then the associated composite marker may be rendered in red. If none of the represented AEDs are considered unhealthy, but one or more need attention, the associated composite marker may be rendered in yellow. If all of the represented AEDs are in good working order, then the associated composite marker may be rendered in green.

In some embodiments, links are included with the fleet map and the map is configured so that when the user selects one of the individual AED location markers, the user is taken to the AED status page associated with that AED (e.g., to a page such as AED status page 400 shown in FIG. 4). Any of a wide variety of conventional gestures or user actions may be designated to signify "selection" an individual AED location marker—as for example by clicking on the marker when the fleet map is rendered on the display of a computing system having a pointer-based user interface, or by touching the location marker on a touch screen, etc.

Other gestures or user actions in connection with an individual AED location marker (such as hovering over an individual marker) may cause an information box to be displayed that provides some basic information about the associated AED. Information box 530 in FIG. 5B is an example of a suitable information box. In the illustrated embodiment, the information box indicates any label or name given to the AED, its status, and the time associated with its last report to the management server 20 (referred to as its last sync time). If/when the represented AED is deemed "not healthy" for any reason, the information box also indicates what is wrong with the device (e.g., electrode pads have been used and need replacement, etc.). In other embodiments, the information presented in the information box may vary widely.

Composite location markers may behave somewhat differently than individual location markers. For example, in some embodiments, selection of a composite location marker causes the fleet map to zoom in to an area that more closely shows the location of the represented AEDs. By way of example, FIG. 5B shows a zoomed in fleet map view that resulted from the selection of composite location marker 510 in FIG. 5A. In the illustrated view, the two represented AEDs are located far enough apart in the context of the zoomed in view that they are now represented individually by individual location markers 518 and 519. This provides a good illustration of how the composite marker are context sensitive relative to the scale of the map in the current view. In the illustrated embodiment, only two AEDs were represented by location marker 510 of FIG. 5A. Therefore, when zoomed in to the level of FIG. 5B, only individual location markers are shown. However, in other circumstances location marker 510 may have represented a large number of AEDs—as for example, in a corporate campus which may have 10s of AEDs or a city or theme park that may have 100s of AEDs. Thus, it is entirely possible that the zoomed-in view itself may have one or more composite location markers. As always, the number of composite and individual location markers in any particular view will depend on the number of AEDs represented in the view, and their relative spacing at the scale of the view. Thus, in any particular view, some, all, or none of the location markers may be rendered as composite location markers and some, all or none of the location markers may be individual location markers.

As previously noted, the zoomed in view of FIG. 5B was attained by selecting the composite location marker 510 in FIG. 5A. However, the same view can readily be obtained using conventional map zooming and navigation techniques.

In some embodiments, a confidence radius may be displayed in association with individual location markers. The confidence radius, denotes an area (radius) within which the AED has reported its location to be. Confidence radii are useful to report in association with location because an AED (or any other location detecting device) may not be able to report its precise location-rather, it reports a determined location and the confidence radius effectively indicating how precise the location measurement is believed to be. In some embodiments, the confidence radius is rendered any time the view of an individual location marker is zoomed-in enough for the radius to be relevant. In other embodiments, the confidence ratio may be displayed when the individual location marker is hovered over or otherwise highlighted by a viewing administrator.

In some embodiments, the location markers are visually visual distinguished when the viewer causes a pointer to hover over the icon, e.g. changing from a full green icon to a green circle outline with white middle to highlight it's the one being hovered over.

In the embodiment described above, composite location markers are segregated strictly by location—i.e., AEDs geographically near one another in the context of the maps current scale are grouped together. In some other embodiments, their may be additional factors that influence grouping. One good example of that is health status. That is, only devices that have the same health state are grouped together. By way of example, in a scenario where 5 devices are located geographically next to each other with 3 being healthy and 2 being at risk, two composite location icons would be rendered next to one another. The first represents the three healthy devices and the second represents the 2 at risk. Similarly, if only 1 of the 5 was at risk or unhealthy, then the unhealthy device would be represented by an individual location marker while the 4 healthy devices would be represented by an adjacent composite location icon.

AED Status

FIG. 4 illustrates a representative device status page 400 in the management platform (also referred to as an AED management screen or page). In the illustrated embodiment, the AED management screen 400 includes a Device Health box 408, a Device Info box 410, an Assigned Users box 411, a Device Accessibility box 413, a Labels box 414, a Use History box 415, a Product Info box 417, a Documents box 418 and an edit mode selector 419. When, an appropriate, an Order New Pads button (not shown) may also be rendered. In other embodiments, more or fewer information boxes and/or features may be rendered, and the specific information rendered in any box and/or the functionality of different features may be varied as desired.

The device health box 408 includes a battery level status indicator 490, a pad status indicator 492, a sync status indicator 494, and an "other status information" field 496 (labeled "Other Issues") and a charging status indicator 498. As discussed above in relation to the fleet health status reporting, the information provided by each of these status indicators is preferably based at least in part on current status information provided by the referenced AED itself as opposed to information manually inputted by an administrator based on whatever information may be available to them. Like the fleet health information, the individual indicators in health box 408 may be color coded to help visually convey their associated status (e.g., green reflecting good, yellow reflecting that the AED may need attention, and red indicating that immediate attention is desired).

The battery level status indicator 490 indicates the current battery level status of the AED. When the AED's battery is rechargeable, the available categories may include categories such as: (i) "Good" indicating that the battery charge level is acceptable; (ii) "Low" indicating that the battery should be recharged, (iii) "At Risk" indicating that functionality may be reduced if the AED is not recharged shortly (or whatever else the "At Risk" category is defined to mean; and (iv) "unknown" when current information about the battery charge level is not available. Of course, a variety of other categories or types of information about the battery could be provided in place of or in addition to the stated categories—as for example an indicator of the percentage charge level of the battery or an estimate of how long the charge is expected to last. When the battery is not rechargeable and periodically needs to be replaced, the available categories may include categories such as: (i) "good" indicating that the battery is well within its intended operational life; (ii) "replacement due soon" indicating that while the battery is currently within its intended operational life, its expiration date is upcoming and a new battery pack should be installed, optionally including the replacement due date; and "expired" indicating that the battery pack that is currently installed on the AED have expired and need immediate replacement. When the battery is replaceable, the current information provided by the AED may be the battery serial number (or other information specifically identifying the battery) and/or the battery percentage and the expiration date may be provided by the management server based on the battery pack that is confirmed to be currently installed in the AED or may be determined based on the reported charge level.

When the AED includes an interface unit or a charge pack (or any other add-on component) with a separate battery, separate categories may optionally be provided to separately report the status of such batteries (e.g., the interface unit battery, the charge pack battery, etc.) as discussed above in the fleet battery status reporting box discussion. Like with the AED battery, the information provided for these other batteries often includes an indicator of the charge level (e.g., percentage charge level) of the battery and/or the current state of each of the batteries.

The pad status indicator 492 indicates the status of the defibrillation electrode pads or electrode pad cartridge currently installed on the AED. As discussed in the fleet health section, the available categories may include categories such as: (i) "good" indicating that the installed electrode pad cartridge/pads is/are well within its intended operational life; (ii) "replace" indicating that the installed cartridge/pads need to be replaced immediately (as, for example, due to their use or expiration); (iii) "install" indicating that no cartridge/pads are currently installed on the AED; (iv) "pad replacement due shortly" indicating that the expiration date for the pads is approaching, optionally including the expiration date; (v) "training pads installed" when training pads are currently installed on the AED; and (vi) "unknown" when current information about the installed pad cartridge/pads is not available. If/when the other types of pads may be installed on the AED—such as pediatric pads or specific types of training pads, or pads with different functionalities, those can be additional categories reported by the pad status indicator 492.

The Order New Pads button (not shown) is a GUI widget that facilitates ordering replacement defibrillation electrode pads. The Order New Pads button is particularly useful when the currently installed pads need to be replaced either immediately or in the near future. In some embodiments, the Order New Pads button only appears when it is time to order replacement pads. In embodiments when the represented AED has a non-rechargeable battery, a similar Order New Battery button may be rendered when it is time to order a new battery pack. In other embodiments, a more general "Shop" or "Order Now" button may be provided that accesses a store from which the user may order a variety of different accessories.

The sync status indicator 494 indicates whether the AED has reported in as expected. The nature of such reporting is described above. When the AED has reported in as expected, the status information in device status page may be considered current (synchronized) with the AED. Alternatively, if the AED has not reported in as expected, the synchronization status is considered "unsynchronized" and the AED's status information may not be as current as desired. The sync status indicator 494 provides a simple mechanism through which an administrator can quickly see whether the information in the status page is current. In the illustrated embodiment, the sync status indicator renders wording such as "Synced" when management platform has current information from the AED, and renders working such as "Unsynced" when the management platform does not have current information from the AED.

The Other Status Information box 496 (labeled "Other Issues") is arranged to convey other status information that may be relevant. In some embodiments this can include indications of any faults or other information that effectively parallels information in Other Fleet Status Items reporting box 330 of FIG. 3. For example, if the AED has failed its most recent self-test, a Failed self-test message such as the wording Failed Self-Test (not shown) is displayed in the Other Status Information box 496. Similarly, if the AED is experiencing a temperature fault, a temperature fault message indicating that the AED is at a location where the temperature is outside of the AEDs operating range (not shown) is displayed in Other Status Information box 496. The temperature fault message may be simple wording such as "Temperature Fault" or "This AED currently located at a temperature outside of its operating range." In some embodiments, other information available to the server such as the current temperature can be additionally or alternatively provided. It should be apparent that the form of the temperature fault indicator/message can vary widely so long as it conveys the fact that the AED is at risk because its current temperature is outside of the designated operating temperature range.

If the AED does not have the most recent software version installed, a software available message (not shown) may be displayed in the Other Status Information box 496. It should be appreciated that the Other Status Information box 496 is not limited to information that corresponds to information presented in fleet status reporting box 330. Rather, any status information that is relevant to the AED may be reported. For example, in some embodiments, when training pads are installed on the AED, a Training Pads Installed message is rendered in Other Status Information box 496. In another example, in some embodiments, when the AED has been moved from its designated location or has moved from its previously reported location, an AED has been moved message is rendered in Other Status Information box 496. Of course, there are a variety of other messages that may be displayed as well.

The charging status indicator 498 indicates whether the AED is currently connected to a charger.

All of the information in the Device Health reporting box is provided by the management server based on information reported by the AEDs—often as part of regular status messages sent to the management server such as status message 152 shown in FIG. 2. In that example, the battery charge level status 490 is provided by battery charge level indicator 168 or Battery low flag 186 and the charging status 498 is provided by charger plugged in flag 174. The pad cartridge status 492 is reported by the management server based on Electrode Pad Cartridge Information 182. The Sync Status 494 is determined by the management server based on when it last received a relevant status message. The "Other Issues" status 496 may be based functionality status indicators such as self-test flag 184, and temperature fault indicator 180.

The Device Info box 410 includes several components, including a map 420 showing the AED's location, a name or label assigned to the AED 421, a short identification of the AED's assigned location 422, a mobility status selector 424, additional placement descriptors 426, a lost/stolen mode selector 428 and a prompt status check feature 430. In some embodiments, when the user selects an edit mode (by selecting edit button 419), the AED name 421, location identifier 422 and placement descriptors 426 each have associated text entry fields that allow the AED's administrator to enter appropriate information into the record. That can be accomplished in-line in the AED status page, or a separate editing interface may be rendered such as the editing interface illustrated in FIG. 12. When not in the editing mode, these fields simply report the current settings/information stored in the management database or other suitable location. In the editing mode, the administrator can also edit other administrator control fields including user assignments, location assignments, naming, etc.

The mobility status selector 424 allows the administrator to designate the AED as either a stationary ("permanent") AED or as a mobile AED. In general, permanent AEDs are expected to be kept at a fixed location, whereas mobile AEDs are expected to be moved around (e.g., an AED that will be kept in a vehicle or carried around by its user). It should be appreciated that the management server 20, may optionally treat the AED somewhat different based on whether AED is designated as a permanent or mobile AED. For example, for a permanent AED, the administrator may request notifications if/when an AED is moved—that is, when the reported location changes from the previously reported location. Such notifications can be sent as texts or e-mails or via other suitable messaging platforms. Since the AED sends it current location as part of the status messages (including the periodic status messages, status messages sent when the AED is in use, and status messages sent in response to a prompt), the management server is frequently informed of the AED's current location. When the received location for a permanent AED is different than its previous location (or moves more than a designated distance from its previous location) and movement messages are requested, the management server 20 sends the designated administrator(s) an appropriate message informing them of the movement. In parallel, if the administrator accesses the device status page 400 before the AED has been returned to its designated location, a message may be rendered in the status information field 496 indicating that the AED has been moved.

In some embodiments, the AED may be assigned a designated home location—e.g., a specific geolocation may be associated with the AED. In such embodiments, the movement notifications may be based on whether the AED has been moved from its designated location (or more than a designated distance from its designated location) as opposed to simply having been moved from its previously reported location. In such embodiments, the management server may also send the administrator notifications when the AED's reported location indicates it has been returned to its designated location (e.g., if the administrator has opted into such notifications). In parallel, if the administrator accesses the device status page 400 before the AED has been returned to its designated location, a message may be rendered in the status information field 496 indicating that the AED has been moved from its designated location.

In some embodiments, an AED may be configured to report its location any time that it senses that it has been moved more than a designated distance. When combined with administrator notifications, this can provide an early notification to the administrator that one of their AEDs may be being taken to the scene of a potential cardiac arrest incident or may have been stolen.

The permanent/mobile designation may be useful for responder networks as well, as described, for example in U.S. Pat. No. 11,869,338 (P023) which is incorporated herein by reference. For example, in some implementations, an AED selection algorithm may directly send a nearby incident notifications to a permanent AED that is known to be close to an incident location without first verifying its location, whereas the present location of a mobile AED may be determined or verified before it is notified of an incident This helps better identify mobile AEDs that are actually nearby an incident and reduces the probability of an AED being notified of an incident for which it can't practically be used for because it is too far away. In another example, an AED map that shows the location of AEDs may be configured to only show permanent AEDs since there is a higher risk that mobile AEDs may not be available if someone goes to try to retrieve it. In other implementations, a mobile AED may be shown on the AED map only after its current location has been verified. In yet another example, the responder network's AED selection algorithm may apply different selection criteria to mobile AEDs—and particularly to AEDs thought to be in vehicles since a vehicle may be able to be timely brought to an incident that is further from the AED than a fixed location AED. For example, the selection algorithm may check-in with mobile AEDs that were last known to be within a wider radius than stationary AEDs since they are more likely to have moved since their last check-in and may therefore now be nearby an incident and available to respond. Also, when it is determined or suspected that the AED is in a moving vehicle, it may be informed of incidents that are further away than if the AED is stationary since the vehicle may be able to drive to the incident scene more quickly.

The Device Accessibility Box 413 contains information/user preferences that are relevant to responder networks. In the illustrated embodiment, the Device Accessibility Box 413 includes a Public/Private selector 441 and a 911 Alerts enablement selector 444. The Public/Private selector gives the administrator a mechanism for indicating whether the AED is a public access AED (e.g., members of the public are free to come get that AED if there is a nearby cardiac arrest incident) or, a private AED, which members of the public are generally not encouraged to try to locate. Public and private AEDs may be handled somewhat differently by the responder network. For example, in some implementations, public access AEDs may appear on public access AED maps that show the location(s) of AEDs, whereas the location of private AED may not be shown on such maps, or may be shown differently on the maps to indicate their "private" status. It should be appreciated that the owner(s) of AEDs that are located in restricted areas (e.g., a locked building, a home, etc.) may not want the general public to try to access or see an AED located in such locations.

In another example, in the context of a volunteer responder network, both public and private AEDs may receive notifications of nearby incidents from the responder network, but a member of the public would not be directed to, or shown the location of, a private AED in the event of an incident since it may not be publicly available. Reaching further, when a responder network in integrated with emergency services answering services (PSAPs) a computer aided dispatch (CAD) system or other interface available to a PSAP dispatcher may be configured to display a map of the area around an incident that shows the location of public access AEDs. AEDs marked "private" may not be shown to the dispatcher in such systems unless or until they have accepted a nearby incident (e.g., a volunteer responder has indicated a willingness to bring the AED to the site of a nearby potential cardiac arrest incident). By way of example, some such systems are described in U.S. patent application Ser. No. 17/903,642 (now U.S. Publication No. 2023/0008570) (P025), which is incorporated herein by reference.

Preferably, participation in the volunteer responder network is an opt-in system. Thus, when the response profile configuration interface is part of an AED management interface, it may include a GUI widget that facilitates opting into notifications. In the embodiment of FIG. 4, this takes the form of 911 Alerts enablement selector 444 (labeled "911 Alerts enabled?"), which allows the AED administrator to enable or disable nearby incident alerts to the associated AED. As such, the 911 Alerts enablement selector allows the AEDs administrator to "opt-out" of nearby incident notifications or to "opt-in" this feature, as desired. If 911 alerts are not enabled, the responder network will not send nearby incident notifications to the associated AED even if the AED is near a potential cardiac arrest incident.

It should be appreciated that the Public/Private selector 441 and the 911 Alerts enablement selector 444 serve quite different functions. As such, nearby incident notifications may be sent to both public and private AEDs in accordance with their owner/administrator's preferences. Similarly, AEDs may be designated as "public" AEDs such that they show up on relevant AED maps, regardless of whether their owner/administrator has opted into 911 notifications.

In some embodiments the management platform user interface (e.g., the AED status page 400 or the corresponding edit page) may optionally include a "Notify 911" (notify emergency services) designator 446. When the Notify 911 selector is turned on, the associated AED is configured to automatically notify emergency services that an AED has been activated for use and provide its current location. In this context, the notification may be sent to the PSAP that is responsible for the AEDs then current location any time that the AED is activated. Such notifications can take the form of an AED Activated message sent directly or indirectly from the AED to the responsible PSAP. Such notifications that there is an active AED at a particular location can serve multiple purposes. For example, if a bystander calls 911 from a generally similar location it can inform the dispatcher that there is an AED on the scene and provide additional confirmation of the location of the incident. In other circumstances, the AED Activated message can serve as the initial notification of an emergency incident that is received by the PSAP and the incident can thereafter be handled in accordance with such PSAPs preferred response protocols. When a Notify 911 selector is provided, it gives the AED's owner/administrator the ability to either activate, or turn off this feature. Such selectors can be provided as part of a response profile user interface for a particular AED (such as the AED status page illustrated in 4), or as part of a user interface that facilitating applying user preference settings to a group of AEDs (such as the dashboard screen illustrated in FIG. 3).

In other embodiments, the Notify 911 selector can be used to facilitate other emergency services communications schemes. For example, the AED can be configured to automatically initiate a voice (or video) call to emergency services (e.g., 911) when the Notify 911 selector is activated, or to initiate a two-way voice and/or data communication channel between the AED and a PSAP operator when the Notify 911 selector is activated. When both voice and video calls are supported by the AED, the notify 911 selector can be further arranged to give the administrator control over whether voice or video call should be used, or other mechanisms can be used to allow the administrator to select audio or video calls as a default.

Communications between the AED 10 and the PSAP can be facilitated in a variety of ways. In some circumstances a direct communications link can be made between the AED and the relevant PSAP. However, in other embodiments, the communications may be made via the AED network server 20 and/or an emergency services interface. As discussed in many of the incorporated patent applications including U.S. patent application Ser. No. 17/903,642 (now U.S. Publication No. 2023/0008570) (P025), it is believed that there are significant implementation and security advantages to utilizing a suitable intermediary such as an AED network server, an emergency services interface and/or other suitable intermediary server(s) to facilitate communications between the AED 10 and the PSAP.

In the discussion above a number of selectors have been described. In some embodiments, the selectors are only made available when the user selects the editing mode (e.g., by selecting edit mode selector 419). In other embodiments, the selectors may be active any time the relevant page is rendered.

Interface Unit Status

As suggested above, Applicant has proposed modular AED designs that include a base defibrillator unit having a separate interface unit (often referred to as the "Connect" unit) attached thereto. The interface unit may include a display, one or more processors, and communications units capable of communicating remotely with the management server 20, as for example, via cellular or Wi-Fi based communications links. In such designs, it is sometimes desirable for the interface to report its status to the management server either separately, in parallel with, or added to the base defibrillator status messages. The interface unit specific information may include information such as: (i) the status of the battery unit (as discussed above); (ii) the results of interface unit self-tests; (iii) the software version installed on the interface unit (as distinguished from the software version installed on the base defibrillator unit); (iv) the MAC address of the interface unit (which also indicates the Wi-Fi network being used), (v) whether a screensaver mode is enabled; (vi) which training mode is set on the device (pre-programmed sequence of shockability during training exercises); (vii) whether one of location services, Wi-Fi, Bluetooth, or Cellular are enabled/disabled; (viii) whether the AED is in a Charge Pack Mode; (ix) the interface unit serial number; (x) the interface unit SIM card #; (xi) a interface unit power on reason (e.g. device woke up due to interface unit button press vs. AED activation); (xii) a current or most recent screen state (e.g. what screen is being or was most recently displayed); and (xiii) the interface unit FCC ID number(s); etc. In such designs, some of the features discussed (e.g., the temperature measurements) may be performed by the interface unit as opposed to by the base defibrillator unit.

In such modular implementations the dashboard 300 and the AED status pages 400 may both be supplemented to include relevant interface unit specific status information. Examples of interface unit status information can include information such as interface unit battery status, the interface unit self-test results, the interface unit software version, etc.

In some modular architectures, the primary path for transmitting AED status messages to the management server is through the interface unit. However, as described in some of the incorporated patents, in some embodiments, the base defibrillator unit may be able to convey status messages via other mechanism—e.g., via BLE advertisements that are received and forwarded to the management server via other intermediate devices such as passing Smartphones. In such embodiments, it may be desirable to provide more extensive synchronization error information. For example, in a described embodiment synchronization states may include states marked "Synched," "Unsynched," "Synching Error," and "Connectivity Error." In this example, an AED marked as "Unsynched" means that the management server has not heard from either the base defibrillator unit or the interface unit for a designated period of time. By way of example, non-communication times of 1-10 days, as for example 5 days may be appropriate for such a designation.

Marking an AED as having a "Synching Error" means that the management server has recently received communication from the interface unit, but it hasn't received updated information from the base defibrillator unit for a designated period of time. To facilitate this, information passed from the base defibrillator unit to the interface unit may have a timestamp that shows the time that such information was last updated. That timestamp is included with all status messages so the management server can readily discern whether the base defibrillator's status information is stale.

Marking an AED as having a "Connectivity Error" means that the interface unit has not been heard from for a designated period of time, but more recent information has been received from the base defibrillator unit.

Although only a few synchronization states have been defined, it should be appreciated that other synchronization states considered relevant to any particular AED may be defined as desired and reported to administrators via the management platform user interface as described.

Troubleshooting

When a viewer sees a fault or potential problem that is flagged in the dashboard 300, the AED status page 400 or elsewhere, they may not immediately understand what (if anything) needs to be done to address the issue. To provide further guidance to the viewer, in some embodiments when the cursor is positioned to hover over an indicator that identifies an issue (e.g., over a fault indicator), a dialog box will appear adjacent or at least partially over the indicator. The dialog box provides further information about the nature of the fault and/or information about what can be done to address the error. The information rendered may include troubleshooting steps and/or pictures, GIFs and/or videos explaining how to address the issue.

Finding Lost AEDs

There are times when an AED may not be at its intended or expected location. For a public access AED, that could be due to the AED having been taken for use at a cardiac arrest incident. For a mobile AED, it could be due to its owner simply forgetting where the AED was left. In a nefarious example, it could be because the AED was stolen. Of course, there are many other reasons why an administrator or owner may not know the location of an AED at any time. The described management platform has a number of features that mitigate the challenges of locating one's AED(s).

Initially, the device map 420 on device status page 400 shows the last reported location of the AED. When the device reports its location at least once every day, the location shown is typically quite current and the device can be found/retrieved by simply going to the location shown.

Sometimes the AED may have been moved since it last reported in. To help address this issue, the administrator can prompt the AED to report its current location via the prompt status check feature 430 (labeled "Ping AED"). More specifically, when an administrator clicks on or otherwise selects the Ping AED button, an Update AED Information request is sent from the browser rendering the device status page (or other rendering software on the administrator's computing device) to the management server 20. In some embodiments, the update AED Information request takes the form of a function call with one of its parameters being the serial number of the missing AED. The AED's serial number is generally available to the rendering software and is often even displayed in Product Info box 417. Upon receiving an Update AED Information request, the management server 20 sends a check-in request to the designated AED. In some embodiments, the check-in request causes the AED to transmit a new status message to the management server 20. The status message sent in response to the check-in message includes the AED's current location (which may be its GPS position, or its location as determined using other location technologies such as Wi-Fi router, cellular tower and/or Bluetooth based triangulation). When the server receives a status message in response to the check-in request, it updates the management database 290 as necessary to reflect the current position and sends the updated location to the administrator's computing device. The updated location is then displayed on the device map 420. The aforementioned process can typically be performed in real time with only slight delays as required to facilitate internet-based communications between the various nodes (e.g., the administrator's computer, the management sever and the designated AED) and any time required to wake-up the AED when it receives the check-in request. It should be apparent that the prompt status check feature 430 provides a very effective tool that gives the administrator the ability to determine exactly where the AED is at any given time. It should be appreciated that since pinging the AED causes the AED to send a new status message, all of the other information provided in a status message is also updated. Thus, the administrator may prompt an update of all of the AED status message reported fields at any time by selecting the Ping AED button 430. In other embodiments, the Check-in request may take the form for a Report Location Request that causes the AED to report only its location, or location and a small amount of other information as opposed to a full status message.

The manner in which the Check-in request is conveyed to the AED may vary based on the AED's current status. For example, if the AED (or its interface unit) is on and connected, then the check-in message can be sent over an established web socket or other appropriate open interface. When the AED is in a standby mode, as for example a low power eDRX mode, then a wake-up message may be sent to the AED (or its interface unit) which causes the unit to wake to an "on" state and establish a web socket (or other) connection with the server to begin communications, including reporting its current status and geolocation.

Although the prompt status check feature can be very helpful in determining the location of an AED at any time, it may not always be possible for the administrator to retrieve the AED, even if its location is known. This could be due to a variety of reasons, as for example, the administrator being located remotely relative to the AED; the AED being at a location that is not publicly accessible (as for example if the AED is taken to the hospital with the patient); the AED is being carried and hence its location is changing; etc. The lost/stolen designator 428 (also referred to as the AED missing designator) gives the AED's administrator/ owner the ability to designate the corresponding AED as missing. When an AED is designated as missing, the AED management server initiates a missing AED protocol which prompts several actions that can help get the AED returned to its desired location. One such protocol will be described below with reference to the flowchart of FIG. 6.

In the illustrated embodiment, the AED missing designator (lost/stolen designator) 428 has two settings—"On" and "Off." In normal circumstances, the location of the AED is generally known, and the missing designator would be Off. If the AED goes missing for any reason, the administrator can inform the management server that the AED is missing by navigating to the AED status page 400 and selecting (e.g., clicking on) the lost/stolen designator 428 to change its state from "Off" to "On." (Block 602). When the lost/stolen designator is set to "On" an AED missing message is sent from the browser rendering the AED status page (or from the app or other user software rendering the AED status page) to the management server 20. (Block 604). In some embodiments, the AED missing message takes the form of a function call with one of its parameters being the serial number of the missing AED. As previously mentioned, the AED's serial number is generally available to the rendering software. In other embodiments, other constructs can be used to identify the missing AED referred to the in AED missing call to the server.

When the AED management server 20 receives the AED missing call, it marks the corresponding record in the management database 290 accordingly (e.g., as "missing"). In parallel, the management server sends an Activate Missing Protocol message to the identified AED 10. (Block 608). When the AED receives an Activate Missing Protocol message, it activates its Missing protocol as represented by block 610. The specific actions that the AED 10 performs as part of the Missing Protocol may vary, but generally, three actions are desired. In the illustrated embodiment, one action the AED takes is to report its current location to the management server. Block 612. When the management server receives the updated location, it stores (e.g., updates) the AED's current location in the management database 290 (Block 614) and transmits the updated location to the administrator's device (Block 616), which in turn updates the location shown on device map 420. Block 618. In other embodiments, when the server receives an updated location from the AED, it checks to see whether the AED has moved from its last reported location and updates the AED's current location in the management database and informs the administrator's device when the location information was last refreshed. As best illustrated in FIG. 5(*b*), in some embodiments, the latest refresh time (labeled "Last Synched") is rendered on the device map so that the administrator can see how current the rendered location is.

Additionally, the AED generates an audio alert (block 620) and displays a visual message, e.g., return instructions, (block 622) on a display screen associated with the AED. These messages are intended for any person that may have the AED in their possession or bystanders that happen to be nearby the AED. The specific content of the missing AED audio alert and visual message may vary widely. By way of example, the audio alert may simply be a beeping or analogous sound that draws attention to the AED, or it could be a verbal message indicating that the AED is lost and asking that the AED be returned to a designated location. In some implementations, the visual message rendered on the display includes instructions for returning the AED to its owner or designated location. For example, a message might say please return this AED to a designated location ((e.g., its home location or to its owner/administrator/responsible person), giving both an address (e.g., a street address and/or a location within a building) to return the AED to, and a map showing the location the AED should be returned to. The return instructions can also include a contact phone number and/or directions to the return location. In some embodiments, the contact information and other return information displayed on the AED is provided by the management server 20 as part of the Activate AED Missing protocol message, or in a message that follows therefrom. This ensures that the most up-to-date contact information for the owner (as reflected in the management database 290) is provided in the "return to owner" message.

In some embodiments, the AED, will repeatedly send its current location to the management server (612) and continue to emit the audio alert (620) and display the visual message (622) until the missing protocol is terminated. This is reflected in decision block 625. Since the AED's location is shared substantially continuously with the management server (616) the AED's location as shown on the device map (618) will be updated in real time as well. Therefore, the administrator can track the AED's movement in real time by monitoring the device map 620. Further, since the audio alert 620 continues to be emitted and the visual message continues to be rendered, a passerby that comes across the AED or others will be informed of where the AED belongs and/or who the AED should be taken to even if they weren't present when the missing protocol was initially activated.

With all these tools available, it is expected that in most cases, the owner/administrator will be able to locate and retrieve the AED relatively quickly. When the AED is found, the administrator turns off the lost/stolen designator 428. Block 630. When lost stolen designator 428 is turned off, the browser (or other rendering software) sends an "AED Found" message to the management server. Block 632. Like the Activate Missing Protocol message, the AED Found message can take the form of a function call with the device serial number as a parameter. Upon receiving the AED Found message, the management server updates the management database to reflect the change and sends a "Terminate Missing Protocol" message to the designated AED. Block 634. When the AED receives the Terminate Missing Protocol message from the management server, it terminates the audio alert and quits rendering the return instructions. It also quits sending the continual location updates and returns to its standard standby protocols and/or otherwise returns to its normal state.

There are other circumstances where return instructions may be helpful. One such example is after emergency use of the AED. Therefore, in some embodiments, return instructions are displayed after emergency use of the AED has been completed. The return instructions displayed after emergency use may be the same as the return instructions displayed in connection with the Missing Protocol. Preferably, the return instructions/information are received from the management server 20 in the general timeframe of the incident (e.g., during the incident or after the emergency use of the AED has been finished). This helps ensure that the displayed return instructions are up to date. In some embodiment in which the AED is included in a responder network, any time that that an AED receives a nearby incident notification, the AED's current return instructions are sent to the AED in substantially the same timeframe. Often a connection will be made between the AED and the responder network server in response to, or as part of the nearby incident notification and the return instructions can be updated as part of that session.

The return instructions can be either requested by the AED, or pushed from the management server. In some embodiments, when emergency usage of the AED is completed, the AED sends an incident complete message to the management server indicating that the emergency use is finished. The incident complete message may be sent automatically by the AED if/when it determines that it is no longer in use, and/or it may be sent in response to a user input such as turning the AED off or selecting a suitable "Done" prompt displayed on the display screen. In some embodiments, one of the actions that the management server takes in response to the incident complete message is to send an Activate Return AED Protocol message to the AED. The Activate Return AED Protocol message provides the same return instructions/information described above in connection with the Missing Protocol. In response to the reception of the Activate Return AED Protocol message, the AED displays the return instructions on the display screen. Optionally, the AED may also output an audio message or signal requesting that the AED be returned to its designated location. Like the missing protocol, an advantage of the described arrangement is that the return instructions are obtained at the time the AED is used, which helps ensure that the displayed return instructions are up to date.

In other embodiments, the return instructions may be electronically stored on the AED so that they can be displayed when needed. In such embodiments, the management server updates the return instructions stored by the AED any time any information contained in the return instructions is updated within the management server. An advantage of this approach is that it allows the current return instructions to be displayed even if the AED is temporarily at a location where it doesn't have connectivity.

Management Database

The management server includes a defibrillator records database which contains records for each of the defibrillators managed by the management server. In some embodiments, the records database is a relational database although other database structures may be used as well. In some embodiments, the database includes AED records, administrator records, entity records, incident records, and others. A few broad categories of information that may be stored in the management database include (but are not limited to) general device information, current device status information, owner/administrator information and privileges, administrative preferences, responder network integration preferences, incident information, and content for the AEDs (e.g., desired software versions, screensaver content, wireless certificates, etc.).

The general device information may be stored in AED records that includes a number of fields that provide information about the AED such as the device ID or serial number which uniquely identifies the AED, its make and model (as appropriate), its purchase date, the software version installed on the AED. The general device information may also include a variety of administrator assigned information such as: (i) the AED's assigned name (used as the information source for name field 421), (ii) the AED's assigned location (used as the information source for assigned location field 422); (iii) a mobility status (used as the information source for mobility status indicator 424); (iv) a privacy status (used as the information source for the privacy indictor 441; (v) a 911 alerts enabled status (used as the information source for 911 alerts indicator 444); (vi) any/all labels applied to the AED (used as the information source for the labels box 414), (vii) users assigned to the AED (used as the information source for assigned users box 411), (viii) return instructions, (ix) placement description (e.g. free text and floor number information used as the source for placement descriptor fields 426), (x) hardware version numbers, (xi) SIM card ID numbers; (xii) FCC Id numbers, (xiii) electrode pad cartridge and/or other accessory serial numbers, (xiv) IP addresses for the AEDs communications unit (which may be integrated or part of an interface unit), (xv) location information including geolocation, altitude and reported accuracy of the location information, (xvi) connection type (e.g., cellular, Wi-Fi) and any other relevant connection information, etc.

In some embodiments, the current status information stored in the AED records includes the current battery status, a variety of information about the installed electrode pads and their current status, a latest update timestamp, a self-test status identifier, an installed software identifier, a temperature fault indicator (and any other fault indicators), etc. The pad/pad cartridge information may include the serial number or other identifier that uniquely identifies the electrode pads installed on the AED, the pads' expiration date, the pad type (e.g., defibrillation pads, adult pads, pediatric pads, training pads, no pads installed, etc.) and any additional information provided by the AEDs such as whether the pads have been used, etc.

As suggested above, the current battery status information may be a simple "good" or "low," or may be more extensive, as for example indicating the last reported battery charge level, depending on the information that is available from the AED. When the battery is replaceable, the battery information can further include the battery serial number (or other unique battery identifier), its expiration date and other such information.

The latest update timestamp (or other indicia) indicates the time of the latest update from the AED. This information can be used in conjunction with the current time to determine the synchronization status for the AED (as reported by sync status indicator 494 and elsewhere). The latest update timestamp generally indicates the time that the most recent communication from the AED was sent or the time that the information in the message was last updated. Preferably this reflects the time and information in the "last" message that was sent from the AED as opposed to the time that such message was received by the management server. The "time sent" or "time updated" is generally preferred because it accounts for delays that may occur in transmission. However, if "time sent" or "time updated" information is not available, in some embodiments and/or circumstances, time received may be used as a substitute. The significance of the "time sent" approach can be understood by considering the following example. In some circumstances, neither a Wi-Fi nor a cellular network may be available (e.g., due to the AED being located in a cellular network coverage hole and a designated Wi-Fi network being down). In such circumstances a status message may be forwarded via a passing intermediate device (e.g., a Smartphone) as described in incorporated U.S. Pat. No. 11,077,312 (P016B). It may be some time before the passing device obtains access suitable for forwarding the status message to the management server—and in practice, the delay could be minutes, hours, or even days. In the meantime, a Wi-Fi connection or other connection may have been re-established, and a newer status message may have been received by the management server. In such circumstances, it is preferable for the management database to be updated based on information in the status message that was sent by the AED most recently, even if it is received before the delayed message.

If the message from an AED does not include a timestamp of the time sent or time updated, the first receiving device (which could be the intermediary device or the management server itself) can insert the time received as a proxy for the time sent.

In some embodiments, the AED records also include a listing of incident identifiers (Incident IDs) that identify incident reports associated with any emergency uses of that AED. The incident reports themselves (which are discussed in more detail below) may be stored separately within the management database.

The administrator/user records include the administrator's contact information and a list of the AEDs that the administrator is associated with. The entity records may include shipping, contact and billing information for the entity as well as a list of administrators and users associated with the entity.

The return instructions associated with an AED indicate the location to which the AED should be returned if/when it has been moved from its designated location (e.g., where it should be returned to after it is used), and/or contact information for a person that can be contacted to facilitate returning the AED.

Custom Screen Saver Content

Public access AED are often located in high traffic areas (e.g., airports, stadiums, buildings, parks, etc.) where they sit for extended periods without being used. Preferably they are located in reasonably high visibility locations so that passersby know that they exist and where they are. Existing public access AEDs tend to be stored in cabinets and/or carrying cases and are not designed to be interacted with by the public.

Some, or all, of the AEDs 10 preferably have an associated display screen. The display screens may be touch sensitive and relatively large (e.g., on the scale of the size of a smartphone display or larger). In some implementations, the display screen is part of an interface unit that is mounted on, but separately powered from a base defibrillator unit. Such defibrillators are described in incorporated U.S. Pat. No. 10,773,091 (P006E) which is incorporated herein by reference.

The relatively large screen in conjunction with the separate powering of the interface unit allows the AEDs to be used in ways intended to engage passersby and/or the public in general. Specifically, when the AED is in a standby mode and/or otherwise not in use, visual content intended to engage passersby can be displayed on the screen. The specific content displayed may vary widely. For example, it may include any of: (i) it could include an invitation to passersby to interact with the AED in some way (e.g., to watch suitable AED, CPR or public safety training materials); (ii) training materials designed to inform passersby about how to operate the AED or respond to a cardiac arrest incident; (iii) CPR instructions and/or AED usage training materials; (iv) a sponsor acknowledgement thanking or otherwise acknowledging a party that paid for or sponsored the AED; (v) general public health and/or safety information; (vi) public notices; (vii) advertising materials, and/or (viii) a variety of other materials. This ability is sometimes referred to herein as the custom screen saver feature/mode since the content is generally intended for display when the AED is not in use and not rendering other messages. The screen saver visual content may take a variety of different forms including static images, GIFs, videos, sequences of images or slides, etc. In some circumstances, a single piece of content is displayed in the screen saver mode. In others different pieces of content may be rendered sequentially—as for example, on a rotating loop (sometimes referred to as a carousel).

In some implementations, the content of the screen saver may also include real-time streamed video such that live video content may be displayed on the display screen. This is particularly practical in AED which have and separately powered interface unit with a display screen when the AED is plugged into a charger. Supporting rendering live streams enables a number of use cases including rendering live content.

When the AED is in a standby mode and connected to power, it may be desirable to render the designated screen saver visual content substantially continuously or for extended time periods (e.g., all day long for heavily trafficked public areas, during normal operating hours for AED's located at a business facility, during normal waking hours for an AED located in a residential environment, etc.). When the AED is not connected to power, such continuous display may be undesirable due to the associated power consumption, but there may be shorter intervals where displaying the screen saver may be desirable. This could be for a short period of time after use of the AED, in periods around when a user is interacting with the AED in a non-emergency setting, etc., during times that the AED is woken up to perform a self-test or for any other reason, etc.

The screensaver content can be uploaded to the AED in a variety of manners. In some embodiments, at least some of the content may be provided by the manufacturer (e.g., AED usage and CPR training materials). In some embodiments, the management platform provides an interface that allows an owner, administrator, or other authorized person to provide visual content to be displayed on the screen of their managed AEDs when the AEDs are in the screensaver mode. The custom content provided in the screensaver can be any content deemed desirable and appropriate by the administrator.

Referring next to FIG. 8, a process for uploading custom screensaver content to managed AEDs will be described. In the illustrated embodiment, the management platform includes a screensaver upload widget (not shown), that when selected by a user facilitates uploading screensaver content to the AED 10. When the administrator selects the screensaver upload widget (block 803), a file chooser or file dialog box is rendered on the administrator's device. The file chooser allows the administrator to navigate their device's file system to select the desired screensaver file. Block 806. In some embodiments, the file chooser facilitates the selection of more than one file for use as in the screensaver carousel.

The screensaver upload widget also allows the administrator to identify one or more target AEDs that they would like the screensaver materials to be installed onto. Block 809. The target AED selection may be performed in a number of ways. For example, if the screensaver upload widget is accessed from a status page 400 for a particular AED, that AED may be the default selection. When the screensaver upload widget is accessed from a more general location such as the dashboard 300, then a device chooser shows a list of items that the administrator may select from. The chooser may allow the administrator to select individual AEDs and/or groups of target AEDs based on any suitable defined attribute. For example, groupings may be based on labels, locations, device status (e.g., devices currently charging), purchase dates (or date ranges), etc. The chooser can also present lists list of AEDs to facilitate selecting individual AEDs when desired.

When a label is selected, the group of AEDs associated with the selected label are identified as targets. When one or more particular AEDs are selected, it is understood that the administrator wishes to install the designated content on each selected AED. The labels are particularly useful in enterprise applications. For example, a particular facility such as an entertainment park, a university campus, an airport, a hotel, etc. may have a number of AEDs that may all have a need to connect to a particular network. Such AEDs may all be categorized in part using a common label (e.g., MIT campus) and that label can be used to identify the appropriate target AEDs. In some embodiments, the device chooser also includes an "All" option which allows the administrator to mark all of the AEDs that they are associated with as targets intended to receive the designated screensaver material(s).

In some embodiments, the screensaver upload widget also includes an hours selector (not shown) that allows the administrator to select the hours that they would like the screensaver to be shown (e.g., from 7 AM to 7 pm Monday through Friday, etc.). Alternatively, or additionally, the hours selector may designate hours for particular content to be shown—e.g., show screensaver A (or include screensaver A in the display carousel) during workweek hours, and show screensaver B (or include screensaver B in the display carousel) on weekends or outside of workweek hours.

The screensaver upload widget also includes an upload button (or other GUI element) that, when selected, causes the identified screensaver file(s) to be uploaded to the management server 20. Block 812. When the selected screensaver file(s) is/are uploaded, a target AED list is also sent to the management server. The target AED list identifies the target AED(s) selected by the administrator. The target AED list may take the form of a list of one or more target AEDs, or designated group of AEDs (e.g. a group associated with a label/location label) that the screensaver file(s) are to be associated with or may simply indicate "all" AEDs— meaning all AEDs associated with the administrator that the administrator has rights to provide screensaver content to. The management server knows the AEDs that are associated with the label and can therefore itself identify the target AEDs based on the label. Alternatively, the administrator may apply the When specific display hours are designated, the selected rendering hours are also included.

In some embodiments the upload widget also enforces any constraints on the content—as for example image aspect ratios, resolutions, permitted formats, etc. The upload widget may also include cropping tools and other tools that allow the user to crop or otherwise process the content into acceptable forms—e.g., the cropping tool allows the user to crop the image to an aspect ratio that is acceptable for the display screen(s) on the target device(s)

Upon receiving the uploaded screensaver content and the indication of the selected AEDs, the management server 20 validates the uploaded files by checking the attached files to verify that they don't contain any malware and that their format, file size, etc. are compatible with the target AEDs. Block 814. In other embodiments, the file validation or portions thereof may be done on the administrator's device. Assuming that the files are acceptable, the management server stores the uploaded screensaver content in the management database 290 and associates the content with each of the target AED with the database. Block 816. In some applications, the uploaded files may be directed to appropriate content reviewing entity for final approval before it is "published," e.g., before it is associated with or distributed to the target AEDs. The nature of the reviewer may vary based on the situation. For example, in enterprise accounts, a content administrator may need to approve content before it is "published." More generally, the management server provider may wish to have some level of content moderation as well to make sure that the uploaded content is not false, damaging, or otherwise undesirable.

The management server then pushes the validated screensaver content out to each of the target AED(s) at the next convenient time by sending an appropriate screensaver content update message. Block 818. In some implementations/circumstances, that may be the next time that the AED connects to the management server and requests/checks for a new custom screensaver available for download. In other implementations/circumstances, the management server may send notifications to some, or all, of the target AEDs requesting that they check-in, and the custom screensaver content is transmitted to the AED when it checks in as requested. In other implementations/circumstances, the screensaver content may be sent directly to one or more of the target AEDs. Typically, the AEDs will be contacted individually, so they may receive the updates at different times.

Once a screensaver file is received by a particular AED, it is added to the AED's screensaver carousel (Block 820) so that the designated content be displayed in due course. Block 822.

In some embodiments, a screensaver API is provided by the management server to facilitate management of the screensaver content on the AEDs. For example, the screensaver API may define an update screensaver message that identifies a list of files that the management server directs the AED to display as the screensaver. Any files that the AED does not already have are attached to the update screensaver message. The AED is then configured to add any new files to its screensaver carousel and remove files from the carousel (if any) that are not identified in the update screensaver message. Alternatively, or additionally, the API may define separate add screensaver file, delete screensaver file, and request list of currently installed screensaver functions. Of course, the API can define other functions as well and/or define functions that perform similar services in other ways.

The description above focuses on adding screensaver content to the AEDs. The management platform preferably also provides a mechanism for identifying custom screensaver files that the administrator would like removed from the AEDs screensaver carousel. To facilitate this, in some implementations, the screensaver upload widget is also configured to display a screensaver list that identifies the screensaver files that are currently installed on any selected AED or group of AEDs (e.g., all AED, or AEDs associated with a label). The administrator can select one or more of the identified files and then request that the selected files be deleted for the screensaver carousels of the identified AEDs. The deletion request follows a flow generally similar to that illustrated in FIG. 8 for adding content, except that the files to be deleted do not need to be attached and the update requests deletion rather than addition of the identified files.

A significant advantage of the described approach is that content designated by an administrator (e.g., the screensaver) can be uploaded to the management server and then automatically installed on the designated AEDs without requiring any further action by the administrator.

As previously mentioned, in some embodiments the AED 10 takes the form of an AED system that includes a base defibrillator unit and an interface unit having a display screen, communications capabilities, and a processor. In such embodiments, the screensaver content can be stored in memory of the interface unit and the interface unit processor controls the display screen in the screensaver mode without any contribution from the base defibrillator unit. With this arrangement, there is no need for the base defibrillator unit to have access to the screensaver content, or even be aware that the interface unit has or is displaying such content.

Return Instructions

An issue that can sometimes arise when an AED is used is how does the AED get returned to its desired location. For example, when a public access AED is brought to the location of a potential cardiac arrest incident, the AED may remain at the location after the person who brought the AED to the scene has already left. This leaves those who are present with the question of where the AED should be returned to. In another example, AEDs are sometimes taken to a hospital with the patient, which leaves the hospital staff with the same quandary—what to do with the AED. To help with this, in some embodiments, the management platform maintains return instructions for the AED. In general, the return instructions indicate a location or address to which the AED can be returned, and contact information (e.g., a phone number, email address, etc.) of a person that can be contacted about returning the AED. Such information can be entered on an individual AED basis or based on groups (e.g., all AEDs at a particular facility) or for the entire fleet (especially when all of the AEDs in the fleet are deployed at a particular location. The management user interface includes GUI widgets that allow the administrator to enter the desired return instructions, and the instructions are maintained as part of the AED records in management database 290.

There are several uses of the return instructions. For example, when the AED is turned off or otherwise shut down after being used, a Return AED message may be displayed on the display screen. By way of example, FIGS. 7A and 7B] are screen shots illustrating representative return instructions that include a Return AED request message pane 700 (FIG. 7A) and a Contact Info pane 710 (FIG. 7B). The illustrated Return AED request message pane asks any person interacting with the AED to return it to a designated location. The Contact Info pane provides contact information for a person that can be contacted to facilitate returning the AED. In some embodiments, the return instructions include a map button or other GUI widget 703 (labeled "Show Me Where" in FIG. 7A) that, when selected, causes the AED to display a map showing the return location and directions to the return location. A representative return map is illustrated in FIG. 7C. In other embodiments, the map may be incorporated into other panes, such as the Return AED request pane, the Contact Info pane, or any other suitable displayed pane. The directions may take the form of a route line/path, turn by turn directions, or any other suitable form. In some embodiments, the Return AED message may optionally also include a "Returned" button (or other GUI widget) 715 (shown in FIG. 7B) that, when selected, causes a message to be sent to the management server indicating that the AED has been returned to its designated location.

When emergency use of the AEDs is completed, displaying the Return AED message can be part of the shut-down protocol. When it's time to render the Return AED message, the AED sends a Return Information request to the management server 20. In reply, the management server provides the return information stored in the management database. This helps ensure that the return instructions are the most up-to-date instructions possible. In other embodiments, the return instructions may be stored in memory on the AED and synchronized with the information stored on the management server any time a change is made to the return instructions stored on the management server. In still other embodiments, the return instructions may be provided to the AED at other appropriate times.

Another use of the return information is as part of the missing AED protocol described above with reference to FIG. 6. When desired, the Return AED message used in the missing AED protocol may be identical to, or very similar to, the "return to owner" message described here.

Wi-Fi Network Selection

There are a few "connected" AEDs currently on the market that support Wi-Fi and/or Cellular communication. For most such AEDs, configuring the AED to work on a particular Wi-Fi network or registering the device on a Cellular Network is quite complex and can be a significant challenge for users-particularly for lay users. As a result, there are many circumstances in which an AED with some level of connectivity capabilities isn't actually connected. Referring next to FIGS. 14A-14E, a graphical user interface and process for simplifying the network selection will be described.

Figures 14A, 14B, 14C, 14D, 14E:
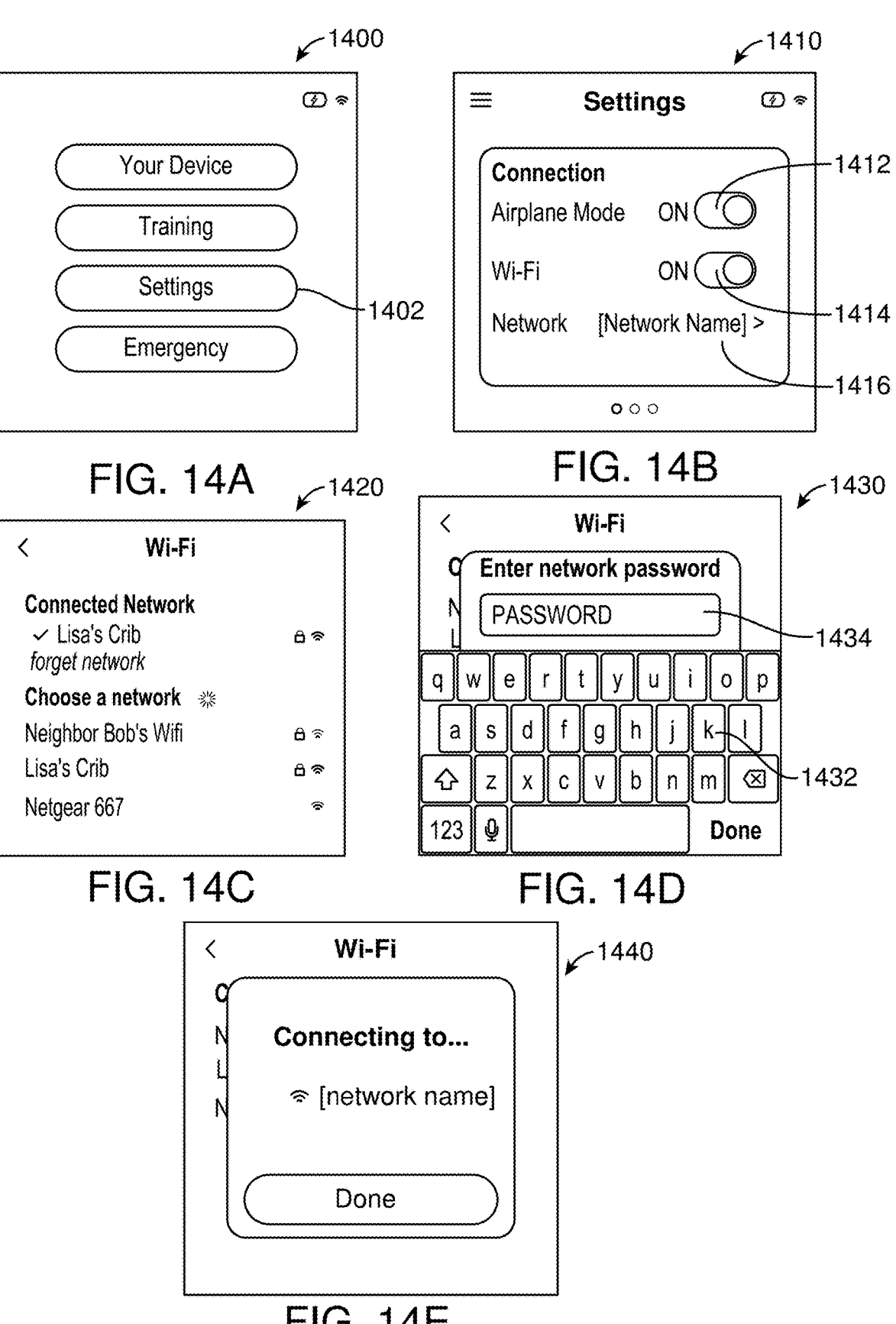

The illustrated embodiment is designed for AEDs having a touch sensitive display screen. In the illustrated embodiment, a home page 1400 that is displayed when the AED is turned on includes a settings button 1402 or other appropriate GUI widget. Selection of the settings button 1402 (e.g., by touching the screen over the displayed setting button in a manner that will be familiar to most users) causes a wireless connections selection frame or page 1410 to be displayed. The wireless connections page includes an airplane mode toggle selector 1412 to selectively turn Cellular connectivity on or off, and Wi-Fi toggle selector 1414 to selectively turn Wi-Fi on or off. There is also a Networks button 1416 that identifies the Wi-Fi network (if any) that the AED is currently connected to. When the networks button is selected, an available networks page or frame 1420 is rendered that provides a list of available Wi-Fi networks as illustrated in FIG. 14C.

The user can select the desired network from the list by touching the touch screen over the desired network or using other appropriate selection techniques. Selection of one of the networks listed in the available networks page/frame causes the AED's communication unit to try to connect to the selected network.

If the selected network requires a network password, the AED will prompt the user to enter a network password. This may be accomplished by rendering a password entry dialog box such as dialog box 1430 as illustrated in FIG. 14D. The password entry dialog box provides a touchscreen based alphanumeric keyboard 1432 in a manner similar to network selection on various computing devices that the user is likely familiar with. The keyboard can be adapted to support special characters as well if/when it is expected that passwords may include special characters. The password entry dialog box 1430 also includes a password field 1434 that shows the text entered by the user and a Done button 1436 that when selected, submits the entered password. Thereafter the AED attempts to establish a connection to the selected network. In some embodiments, a message such as dialog box 1440 illustrated in FIG. 14E is rendered to inform the user that the communications unit is trying to connect to the selected network.

Network Certificates

Some wireless networks require that a connecting device have a digital certificate installed thereon or provide other network credentials. For example, Wi-Fi certificates are commonly required by enterprises network to provide secure and encrypted access to the network for employees and guests. Similarly, public, and private networks such as those found in airports, coffee shops, and many other locations, often require Wi-Fi certificates to access the network. This can present a challenge in connecting AEDs to such networks since the AED must have a mechanism for receiving and installing the certificate. Referring next to FIG. 9, a certificate installation method enabled by the management platform will be described.

The management platform user interface includes a wireless network certificate upload widget (not shown). When an administrator selects the certificate upload widget (block 903), a file chooser or file dialog box is rendered on the administrator's device. The file chooser allows the administrator to navigate their device's file system to select the desired certificate file (e.g., a Wi-Fi certificate for a network that the AED(s) is/are intended to connect to). Block 906. In some embodiments, the file chooser allows the selection of more than one certificate file. The certificate upload widget also allows the administrator to choose or enter the name of the network that the digital certificate is associated with. Block 907.

The certificate upload widget also allows the administrator to identify one or more target AEDs that they would like the certificate to be installed onto. Block 909. The target AED selection may be performed in a number of ways. For example, if the certificate upload widget is accessed from a status page 400 for a particular AED, that AED may be the default selection. When the certificate upload widget is accessed from a more general location such as the dashboard 300, then a device chooser may show a list of labels and/or a list of AEDs that the administrator may select from.

When a label is selected, it is understood that the administrator wishes to install the designated certificate on all of the AEDs associated with that label. When one or more particular AEDs are selected, it is understood that the administrator wishes to install the designated certificate on each selected AED. It is noted that the labels are particularly useful in enterprise applications. For example, a particular facility such as an entertainment park, a university campus, an airport, a hotel, etc. may have a number of AEDs that may all have a need to connect to a particular network. Such AEDs may all be categorized in part using a common label (e.g., MIT main campus) and that that label can be used to identify the appropriate target AEDs. In some embodiments, the device chooser may also include an "All" option which allows the administrator to mark all of the AEDs that they are associated with as targets intended to receive the designated certificate(s).

The certificate upload widget also includes a mechanism that allows the administrator to identify the network that they want each AED (or groups of AEDs) to connect to and to apply the certificate too. In many cases, the administrator will know the network that they would like to AED to connect to and as such, can readily identify the target network(s). The certificate upload widget may also include a network selection tool that allows administrators located in the vicinity of the target network to select a network from a list of available networks—e.g., the networks that can be detected by the administrator's device. The network selection tool is also configured to prompt a Wi-Fi network check by the AED that reports the wireless networks that it has visibility to (the interaction with the AED may be facilitated by the management server using a cellular connection with the AED).

The certificate upload widget also includes an upload button (or other GUI element) that, when selected, causes the selected certificate file to be uploaded to the management server 20. Block 914. When the certificate is uploaded, a target AED list is also sent to the management server. The target AED list identifies the target AED(s) selected by the administrator.

After the management server receives the certificate, it then pushes the certificate out to the target AED(s) at the next available opportunity. Block 917. In some implementations/circumstances, that may be the next time that the AED connects to the management server. In other implementations/circumstances, the management server may send notifications to some or all of the target AEDs requesting that they check-in, and the certificates are transmitted to the target AEDs when they check in as requested. In other implementations/circumstances, the certificates may be sent directly to one or more of the target AEDs.

Once the certificate is received by a particular AED, it is installed on the AED as represented by block 920. Once installed on the AED, the certificate can be used to facilitate connecting to the desired network—e.g., the designated Wi-Fi network. Block 923.

It should be appreciated that there are a number of use cases for the described certificate uploading and installation process. For example, as part of the device set-up, labels may be associated with the AED. If a wireless certificate is already associated with one of the labels applied to the AED, or if the certificate is associated with all of an administrator's AEDs, then the management server knows that the AED is supposed to be provided with the certificate without requiring any further input from the administrator. In such circumstances, the certificate (which is already held by the management server) will be automatically conveyed to the AED at the next appropriate opportunity.

The time and location at which the wireless certificate is installed will vary based on when the AED's record is updated. For example, when a new AED is purchased, a corresponding record may be automatically created in the management platform and associated with the purchaser as described in more detail below. Thus, the administrator can set up the AED even before it is received. If the record is updated in a manner that associates the AED with the certificate before the AED is shipped, the certificate may be automatically installed on the AED before it is shipped. In another example, if the record is updated while the AED is in the hands of an administrator, the certificate may be automatically installed before it is placed at its desired location. In yet another example, if the record is updated while the AED is positioned at its desired location, the certificate may be installed even if the AED does not have Wi-Fi connectivity beyond the network for which the certificate is required. This is because there are alternative paths by which the certificate may be pushed to the AED. Specifically, in some embodiments the AED also has cellular connectivity, so the certificate may be delivered via a cellular network. Similarly, in some embodiments, the certificate may be delivered to the AED via intermediary devices (e.g., cell phones having an appropriate app installed thereon) that are in the vicinity of, or pass by the AED using a short-range wireless communications protocol such as Bluetooth. Such an intermediary delivery approach is described in incorporated U.S. Pat. No. 11,077,312 (P016B).

In some embodiments, the management platform also includes an interface that allows the administrator to identify wireless network certificates that should be removed from designated AEDs. This can be part of the certificate upload widget or a separate mechanism. The certificate removal may be handled in substantially the same manner as the removal of the screensaver content previously described.

The description above focuses primarily on Wi-Fi network certificates. However, it should be appreciated that the same approaches can be used to handle any type of credentials required for any type of communications network. This includes passwords required by Wi-Fi networks and/or certificates or passwords required by any other type of wireless network. When applied to passwords, the relevant password(s) is entered by the administrator and the entered password is transmitted to the management server and target AED(s) rather than the network certificate. In some embodiments, the AED network server sends a set communications network password command to the target AED(s). The set communications network password identifies the applicable network and the password required to utilize such network. In response to receiving the set communications network password command, the target AED attempts to access the communications network using the password. In some embodiments, the target AED reports back to the management server whether such an attempt was successful.

In some embodiments, Wi-Fi certificates and/or network passwords may be delivered to target AEDs through other mechanisms as well. For example, the management platform user interface may provide a mechanism for enabling the administrator to connect the administrator device to the Wi-Fi network of choice. The credentials used to connect to the chosen Wi-Fi network may then be either uploaded to the management server and delivered from the management server to the target device(s), or may be conveyed directly to the target device(s) over the Wi-Fi network without requiring management server involvement. When the administrator connects to the Wi-Fi network of choice, a dialog box may be rendered within the management platform user interface asking whether the administrator wants to apply this Wi-Fi network to target devices. If/when the administrator answers affirmatively, the Wi-Fi credentials may be conveyed directly to any target AEDs that are visible to that network. Optionally, the credentials may also be uploaded to the management server for delivery to other or future target devices as well.

User Provided Content

The Screen Saver and Wi-Fi certificate upload capabilities are a couple of examples in which a customer may upload unique customer content (e.g., media files, certificates, etc.) to the AED by way of the management platform. This is believed to be quite unique in the context of AEDs and defibrillators in general. One of the challenges to providing customer content to an AED is that, in many jurisdictions, AEDs are highly regulated devices and as such, updates to the software or other content of an AED may be subject to regulatory approval. This makes supporting the addition of customer content files to AEDs particularly challenging. The modular architecture shown in and described with reference to FIGS. 15-17, with a base defibrillator unit 110 and a separate substantially self-contained interface unit 200 substantially mitigate those challenges, which provides a significant advantage over traditional AED designs. Specifically, the base unit and the interface unit are preferably designed such that the interface unit 200 does not impact the life-saving functionalities of the base defibrillator unit 110 in any way. The interface unit 200 has a touch sensitive display 220, one or more processors, communication capabilities and its own battery. The provided content such as the Screen Saver, Wi-Fi certificates etc., are installed on the interface unit rather than the base unit and any user actions associated with such content is only with the interface unit. As such, the user provided content does not in any way impact the operation of the self-contained base defibrillator unit—which substantially mitigate safety risk associated with the user supplied content.

If/when an administrator is given control over selection of a configuration that impacts the base defibrillator unit 110 (such as the shock/CPR protocol, instruction language, certain power settings, etc.), then the management platform is arranged so that the administrator is only allowed to select from a set of designated set of configurations that are preapproved for the AED or the location of the AED.

Power Modes & Charging Status

There are a wide variety of different situations in which an AED may be deployed. For example, many AEDs are expected to be kept at a fixed location (stationary), while others may be expected to be moved often (mobile). Mobile AEDs may, for example, be kept in a vehicle (e.g., an ambulance or EMT vehicle, a police vehicle, etc.) or carried with a person (e.g., by a medic, a coach, someone accompanying a person having an elevated risk of cardiac arrest, or other interested individuals). Within each category, there may practically be very different abilities to charge the AED on a regular basis. For example, some stationary AEDs may be positioned on a stand or in a cabinet that is near a power outlet or is otherwise powered so that the AED can effectively be plugged into "main" power substantially continuously (e.g., substantially continuous power from the power grid-aka "line" power or "grid" power). Others may be positioned at a location that does not have ready access to such main power and therefore must rely exclusively on battery power for very extended periods of time.

Among AEDs that do not have access to a main power supply, some may rely exclusively on the AED's battery(ies) (e.g., the AED and AED interface unit batteries), while others may be connected to a battery pack that can be used to recharge the AED's battery(ies) to greatly extend the period that the AED can be left unattended.

Each time an AED transmits information to external devices or systems or wakes up for any reason (e.g., to perform a maintenance function such as a self-test), it uses energy and thus the frequency of connections, self-tests and other tasks performed by the AED can have a significant impact on the battery life of the AED, or in the context of a rechargeable battery, the time between required recharges. Conversely, capabilities such as good connectivity, the ability for passersby to interact with the AED, and frequent self-tests are all desirable attributes. Therefore, in some embodiments, the AED may have multiple different power modes that support different levels of standby mode functionality, which provides a mechanism for managing the power draw, and therefore battery life of the AED.

For example, in some embodiments, the AED may have: (1) a "high" power mode; (2) a "low" power mode; (3) a "default" power mode; and (4) a "charge pack" power mode, each of which have different sets of setting. By way of example, in the high-power mode, an interface unit may check-in every few seconds (e.g., every 5 seconds or less) when the AED is in the standby mode. In contrast, a default mode may check-in less frequently (e.g., every 40 seconds). In the low power and charge pack modes, the AED may check-in much less frequently, as for example, once a day. Of course, in other embodiments, more or fewer different power modes may be provided, and the specific check-in intervals associated with any particular power mode may vary widely. In some embodiments, the power modes are tiers such that different power level modes (e.g., high, default and low) each have multiple sub modes (e.g., a regular mode and a charge pack mode).

These different power modes provide different levels of functionality. For example, as mentioned previously, applicant has described AED inclusive responder networks that can be activated by Public Safety Answering Point (PSAP) telecommunicators (e.g., 911 dispatchers) and others/other systems. When activated, the responder network server (which may take the form of management server 20) sends nearby incident notifications to AEDs indicating that there is a nearby cardiac arrest incident for which the AED and/or the volunteer responder's assistance may be useful. Often, for security and other reasons, that message is sent in response to the AED checking in with the management server, or checking to see if it has messages, such as a message requesting that it check-in with the management server. Thus, when an AED is part of a responder network, it is highly desirable for the AED to check-in/check for messages frequently (e.g., checking in on the order of every 1-5 seconds works well). That check-in can be with the management server 20, a separate responder network server, or both. In practice, what we refer to as checking-in does not necessarily require making an actual connection with the server. Rather, to help reduce power consumption, the AED (e.g., its interface unit) may simply periodically check for messages using a technology such as Extended Discontinuous Reception (eDRX). When the management server wishes the AED to check in or report its location (or otherwise wants to communicate with the AED), the management server sends an appropriate check-in/report location message to the AED. When the AED next checks for messages, it will receive the check-in request message and respond accordingly—e.g., by establishing a connection with the management server, sending a status message, reporting its location, asking the management server whether it has other instructions/commands/messages, and/or perform other tasks requested/commanded by the received message.

Frequent check-ins/messages checks help ensure that the AED will be quickly notified of nearby incidents when the responder network is activated because the latency associated with receiving a message is effectively limited to the selected check-in interval. Of the power levels articulated in the example above, this is best accommodated by the high-power mode. The less frequent check-in interval of the default mode (e.g., 40 seconds) can still facilitate participation in the responder network, but it statistically enhances the response time for the associated AED due to the longer potential check-in latency. The low and charge-pack power modes, which check-in much less frequently aren't really suitable for being activated by responder networks that rely on the AED checking in with the server to facilitate connectivity. But when the AED is not part of a responder network, checking in less frequency (e.g., once a day) is very suitable for the required purposes.

There are a number of other power consuming features that AEDs can modulate to save power or provide improved functionality. For example, in some embodiments, the display of an interface unit may be left on when the AED is plugged in and in a high-power or default mode (e.g., to display a screen saver or user interface as described herein), and turned off when the AED is not plugged in unless the AED is in use or being interacted with. In contrast, in the low and charge pack modes, the interface unit screen may be turned off unless the AED is not in use or being interacted with. In the case of the charge pack mode, the screen is turned off even though the AED is ostensibly being externally powered by the charge pack. Different power modes can also have different delay times for turning off the screen after a user has interacted with the AED.

There are a number of other functions and features that also impact the standby power draw of the AED and their frequency can also be modulated based on power mode. For example, it takes energy to perform a self-test so the frequency of self-tests, or the number of checks performed as part of a self-test may vary. For example, in some power modes self-tests may be performed every day, while in others, the self-tests are performed less frequently. In some embodiments different self-tests may be performed at different intervals—e.g., some self-tests done daily, others weekly and others monthly and again, the frequency of each of these types of self-test may be varied based on factors such as power mode, and when the AED is not on a charger, battery charge level.

As described in some of the incorporated patents, in some embodiments, the AED may be configured to regularly transmit status messages as BLE advertisements. In various embodiments, some power modes may enable BLE advertisements while the AED is in a standby mode, while other power modes may disable such BLE advertisements.

In some embodiments, the AED 10 periodically reports the power mode that it is currently in to the management server. For example, the periodic status messages sent by the AED may include a field that identifies the power mode that the AED is currently in (not shown in FIG. 2). In turn, the management server tracks the power mode that each AED is in by saving the current power mode in the management platform database 290. In other embodiments, the AED management server simply tracks the power mode that the AED has been set in without requiring periodic reporting from the AED itself.

In some embodiments, the power mode can be set remotely via the AED management server 20. For example, in some embodiments, the AED is configured to set its power mode to a desired state in response to a Set Power Mode command or an updated configuration file received from the management server.

The AED status page 400 can optionally include a power mode field that indicates the power mode that the AED is currently in. If/when desired, an administrator can set or change the power mode for a particular AED by directing the desired change in the management platform. In some embodiments, this is accomplished by selecting the edit mode elector 419 to facilitate editing and then selecting the desired power mode setting from a set of available settings. Of course, in other embodiments, other GUI constructs can be used to facilitate selecting the desired power mode. The power mode settings may be set on a fleet level (e.g., applied to all AEDs associated with the administrator), based on labels or other groups (e.g., applied to all AEDs associated with a particular label or group), individually on a single AED, or on a group of specified AEDs, or in any other supported manner.

When a new power mode selection is made, a change power mode request is sent from the management platform user interface to the management server, which updates the management database 290 accordingly. The management server then sends appropriate set power mode commands to each AED for which a different power mode has been requested.

One of the power modes referred to in the discussion above is the "charge pack mode." When the AED is connected to a charge pack, it is effectively on a charger, but the nature of the charging is quite different than charging from main power. Therefore, in embodiments where the use of a charge pack is a possibility, the charger plugged in flag 174 shown in FIG. 2 may supplemented with another flag that indicates whether the AED is plugged into a charge pack, or a multi-bit indicator may be used to provide more detail of the charging status.

In some embodiments in which a cellular network is utilized for communications with the management server, techniques such as Discontinuous Reception (DRX) or Extended Discontinuous Reception (eDRX) are utilized to help reduce power. When eDRX or similar technologies are used, the interface unit (or communication unit within an AED) is put in a sleep mode for a designated period of time and then wakes after a fixed interval to receive signals. Longer DRX cycles enable the interface unit to stay in a power-saving state for longer periods of time. In some embodiments eDRX is used with power save mode (PSM) to obtain additional power savings. Power Save Mode (PSM) is a feature of a cellular modem that turns off the device radio and puts the device to sleep without the need of reconnecting itself to the network when it next wakes up. The cellular modem only reconnects to the network when required. With eDRX, the interface unit can listen for pending messages without having to establish a full network connection. By just listening for a pending message, eDRX uses less power than if it made a full network connection. The time needed for this listening process is also much shorter than the time it takes to make a full network connection. Although eDRX itself is a technology applicable to cellular communications networks analogous power saving techniques can be used with other communications technologies. For example, Wi-Fi devices can use Power Save Mode (PSM), Target Wake Time (TWT) and other technologies to accomplish analogous power savings.

Setting AED Configuration

The section above gives examples of mechanisms by which an administrator may remotely direct the power mode setting of their AEDs. The same approach can be used to implement any other administrator selectable operating mode or configuration appropriate for the AED. The same approach may also be used by a distributor or the AED manufacturer to remotely apply desired settings and/or configurations to a particular AED or set of AEDs that are still within the control of such distributor or manufacturer. This capability has a number of useful applications. For example, in some jurisdictions it may be appropriate for an administrator to set selected AED settings such as: (i) the shock waveform utilized (e.g., Biphasic Truncated Exponential (BTE) waveform, vs. Rectilinear Biphasic (RB), single shock vs. double sequential defibrillation, etc.); (ii) the energy level or maximum voltage of the defibrillation shock; (iii) the base and/or secondary language in which user instructions are rendered; (iv) setting the CPR interval (i.e., the period between shock analysis/delivery in which a user is instructed to perform CPR); etc.

It is noted that the recommended defibrillation protocols recommended by medical personnel or mandated by government action may change from time-to-time and/or may vary from jurisdiction to jurisdiction. The described mechanism for enabling administrators to remotely adjust the setting of their managed AED via the management platform can be extremely useful resetting setting capabilities can be particularly useful in such circumstances. In one specific example, an administrator may be responsible for AEDs in multiple jurisdictions, some of which may require different settings, different instruction languages, etc. The described mechanism allows the administrator to order AEDs without pre-specifying the settings and then have the AEDs remotely configured appropriately for the locations at which they are deployed.

The described ability to remotely update the setting and/or configuration of the AED can also be very useful for the AED's manufacturer and/or distributors. For example, the remote updates allow a manufacturer to produce AEDs without installing separate configurations for different AEDs at the time of manufacture based on the jurisdiction that such AEDs will eventually be sold into. Rather, such configuration can be done after the destination for the AED has been determined (e.g., at a shipping location, at a distributor, or even after the AED has been shipped or delivered to the customer). In an example of the latter, when an AED is initialized at a customer location, it reports its current location. When desired, that location can be used as the basis for determining the default settings and/or configurations to be applied to the AED. Thus, when the AED is initialized and checks-in with the management server, the management server can determine whether it has the appropriate configuration file for the specific jurisdiction and/or customer. If not, the management server sends an appropriate configuration file update to the AED, which then installs the updated configuration file. This entire update can be accomplished without requiring the AED's recipient to do anything other than, if appropriate, initiate the initiation process.

The mechanisms described above also allow manufacturers to push setting updates to all AEDs or any selected set of AEDs (e.g., all AEDs in a particular jurisdiction) in response to mandated or recommended changes in defibrillation shock or CPR protocols.

In some of the described embodiments, the management server sends a settings update command to an AED to implement a desired setting change. However, in other embodiments, a change may be better implemented by sending an updated or different configuration file or an appropriate updated or different software package to the targeted AED(s). As discussed in more detail below, there are a number of different settings and configurations that can be updated using a similar approach. These include PIN code required to access setting changing functionality on the AED; power modes; screen saver on/off commands, training mode configurations, connectivity settings, etc. Any of these settings can be set on an individual AED level, a group level (e.g. based on labels or location), on an organizational level, etc.

Uploading or Editing Content

It should be apparent from the foregoing that the management platform provides a mechanism that an administrator can use to designate content to be automatically installed on one or more of their AEDs and/or to provide or edit information that may be used by the AED. Although screensaver management, wireless certificate management and return instructions management have been described as examples, it should be appreciated that the same approach can be used to provide any other appropriate information or content to the managed AEDs.

Suitable APIs can be provided in the management platform to facilitate the designation, uploading and/or removal of any appropriate administrator designated content to/from a set of one or more designated AEDs. The APIs provide mechanisms that facilitate the administrator identifying specific content to be installed on or removed from designated AEDs and for uploading the specified content from an administrator computing device to the management server. The management server maintains records of what content is designated for which AEDs in the management database 290 and validates and stores the desired content. Any content that is not validated can be discarded and not delivered to the AEDs. The APIs also provide a mechanism for automatically delivering the uploaded content to the designated AEDs. Information that is useful to users of the AED, such as the described return instructions and other information can be provided and updated in a similar automated manner. A significant advantage of the described approach is that content or information designated by an administrator sitting at a location remote from the designated AEDs can be uploaded to the management server and then automatically installed on the designated AEDs without requiring any further action by the administrator. Similarly, content or information designated to be removed or edited by the administrator can be automatically removed or updated from the designated AEDs without requiring that the administrator manually interact with any of the designated AEDs.

AED systems that include a base defibrillator unit that independently functions as a fully functional AED and an interface unit having a display screen, communications capabilities, and a processor are particularly well suited for use in the described system. In such embodiments, the administrator designated content or information is preferably stored in memory of the interface unit and the interface unit processor controls the use and/or display of such content/information without any contribution from the base defibrillator unit. In some embodiments, the base defibrillator unit does not have access to the administrator provided content/information and is not even aware that the interface unit has or is utilizing or displaying such content. This is particularly desirable from a regulatory standpoint since the administrator designated content or information cannot impact the functionality of the base defibrillator unit itself in any way.

There are a wide variety of different types of content that can be loaded onto, or removed from the AED or an attached AED interface unit using the described approach. For example, the content could take the form of: (i) custom user interface menu setups; (ii) training content including different combinations or permutations of videos, games, quizzes, tutorials, etc.; custom editable settings (e.g., some groups may desire for the device settings to be settable on the device, whereas others may only want their devices to use only the setting defined by the administrator using the management platform); (iii) device information accessibility that defines what information can be accessed directly on the device (e.g., some users may prefer that the device serial numbers are not viewable on the AEDs themselves, whereas others may wish for such information to be accessible); (iv) notification preferences—e.g., some users may wish to allow notification preferences to be set using the AED itself, whereas others may prefer that such preferences can only be set via the management platform.

Beacons and Advertisements

In some embodiments, the AED 10 has the ability to generate a beacon (e.g., an iBeacon, an Eddystone beacon, etc.) or more generally an advertisement (e.g., a BLE advertisement) that provides information about the AED to suitably equipped listening device that are close enough to receive the beacon. Such AEDs are described, for example, in incorporated U.S. Pat. No. 11,077,312 (P016B) and U.S. Pat. No. 11,452,881 (P016A). When the beacon is received by a suitably equipped listening device (e.g., a passing or nearby Smartphone with a defibrillator App) the listening device generates a user notification that indicates: (a) that an AED is located nearby (e.g., located in the building that was just entered); and (b) as appropriate, the specific message from the AED (e.g., "An AED is located on the wall to the right side of the reception desk"). When an AED has such a capability, the AED status page 400 may also include a Beacon field (not shown) that indicates whether the Beacon feature is enabled. When beacons are enabled, the AED broadcasts beacons. When beacons are not enabled, the AED does not broadcast beacons. One particularly useful application of such beacons is location beacons, that identify the location of the AED, however, there are many other applications for the use of beacons.

The management platform also includes interfaces for enabling or disabling the location beacons. Like many of the other described features, the location beacons can be set on an individual or group basis. To facilitate location beacon control on an individual AED basis, the status Location Beacon field on status page 400 may include an on/off selector that the administrator may utilize to change the Location Beacon status. Alternatively, or additionally, an enable beacons selector may be included in an edit status page rendered in response to the selection of edit mode selector 419. Similarly, location beacon settings can be made on a group basis as well—as for example, all AEDs associated with a particular label, or all AEDs associated with a particular administrator, location, entity, or other defined category.

The same approach can be used for providing administrator control of enabling or disabling the broadcasting of BLE advertisements.

Access Control

In some embodiments, the AED 10 may be configured such that some of its settings can be changed via an interface on the AED itself. That enables the owner to make desired setting changes directly on the AED. However, for some AEDs (particularly public access AEDs) an unintended consequence may be that a passerby or malicious actor could potentially change the settings on an AED in a manner that was not desired by the owner. To mitigate that risk, in some embodiments, a security code such as a PIN code or password may be required to be entered before a person can make setting changes on the AED itself. In some implementations, PIN codes/passwords may only be required for editing a defined set of settings. For example, a PIN code/password may be required to change settings such as airplane mode, Wi-Fi mode, screensaver, low power mode, etc.

In some embodiments, access control such as PIN codes and passwords may be managed through the management platform. In such embodiments, the management platform user interface includes a mechanism for setting and otherwise managing PIN code access requirements. For example, in some embodiments, a GUI widget is provided that allows the administrator to select/set a desired settings access control from one of: (1) No PIN Code Required; (2) PIN Code Required; and (3) No Setting Changes Permitted. As the titles suggest, when no PIN code is required, anyone with access to the AED may make settings changes by navigating through a settings user interface on the AED itself. When a PIN code is required, a gateway user interface rendered on the AED requires the user to enter an appropriate PIN code before they can make any changes to the device settings on the AED itself. When the No Setting Changes Permitted mode is in effect, all device-based settings changes are disabled so that users cannot make settings changes on the AED itself, thereby effectively locking the AED.

When PIN codes are enabled, the required PIN codes may be set and changed by way of the management platform user interface.

As in other examples provided herein, the access controls may be set on an individual AED basis, applied by AEDs associated with a particular group or label, or applied to all AEDs managed by the acting administrator. In each of the cases, when the desired setting access control level is set using the management platform user interface, the selected access control level settings are conveyed to the management server 20. In turn the management platform stores the selected setting in the management database 290 and sends appropriate access control settings commands to the targeted AEDs. The targeted AEDs, in turn, apply the commanded access control level and any associated PIN code requirements. Although the settings of PIN codes has been specifically described, it should be appreciated that other access control security codes such as passwords can be set in the same manner.

There may be a wide variety of AED settings that can be set directly on the AED and therefore controlled via the described access control mechanism. For example, in some embodiment, the settings user interface on the AED may have various communications related settings selector such as an "airplane mode" selector (which disables cellular access when airplane mode is selected); a Wi-Fi selector (which allows Wi-Fi to be turned on or off; a Bluetooth Selector (which allows Bluetooth communications to be turned on or off); a Wi-Fi network selector, which permits the user to select a desired Wi-Fi network. Selectors may be provided for other features as well, as for example: a Screensaver selector which enables a user to turn on or off the screensaver function; a power mode selector that allows a user to select the desired power mode; etc.

In some embodiments the settings user interface on the AED may allow the user to select different training protocols when the AED is in a training mode. Some may even allow the user to select different use parameters such as instruction language, the shock waveform or voltage level, the CPR protocol used, etc.

Remote Management of AED Settings

Any setting on the AED can also be managed remotely using a process similar to the described access control. Such a process will be described with reference to FIG. 18. Generally, an AED settings management page or any other page, pane, window, etc. in the management platform may have one or more selectors, pull down menus or other GUI widgets that allow the administrator to selected desired settings for their managed AEDs. For example, the selectors may be rendered as part of, or accessible from, one or more of an editing interface such as the interface illustrated in FIG. 12, the dashboard 300, AED status page 400 or any other any other suitable page, pane, window, etc.

When a setting change is desired, the AED's administrator (i.e., a person with suitable administrative control of one or more of an AED's settings) navigates to a location in the management platform with the desired setting selector(s) as represented by block 1802.

The administrator then selects or otherwise identifies the desired setting(s) (block 1804) and target AED(s) to which the desired setting(s) are to be applied (block 1806). The target AEDs can be identified by individually selecting or designating specific AEDs, to "all" AEDs associated with an administrator or organization, or in groups through the use of labels or other similar constructs (e.g., apply this setting to all AEDs associated with one or more given labels). In some embodiments, the target AED is implicitly selected due to the page/pane in which the selection is made being associated with a specific AED (e.g., AED status page 400).

After the desired settings have been selected, the administrator's device's management platform user interface sends a suitable AED settings designation message to the management server 20. Block 1808. Typically, the AED settings designation message identifies the target AEDs and the desired settings state. When specific target AEDs are identified, the message may include the AED's serial number or any other identifier that uniquely identifies the AED. When the setting is associated with a label, a corresponding label identifier that uniquely identifies the desired group(s) may be included in the AED settings designation message. When the setting is associated with multiple labels, corresponding label identifiers are provided for each of the selected groups. When the desired settings are selected in the context of a page associated with a specific AED (e.g., AED status page 400), it is sometimes not necessary to explicitly identify the target AED in the AED settings designation message if/when the management server has knowledge of the page currently rendered in the management platform user interface since the management server can infer the target based on the context. That is, the target AED is determined indirectly by the management server.

The specific structure and format of the settings designation message may vary widely and, when appropriate, may include information or an attached file selected or provided by the administrator. A good example of such additional information is a Require Security Code Access Control settings message intended to direct the target AED(s) to require a password or PIN code to allow users to change settings on the target AED itself. Typically, such a settings designation message would also include the required password or PIN code to be assigned to the AED (e.g., as a required parameter in an API or method call). When desired, the settings designation message may be implemented as a sequence of two or more messages transmitted by the administrator device, or a sequence of communications between the administrator device and the management server 20. Of course, any of a variety of commitment checks can be provided to ensure that the administrator truly intended to apply the selected settings before the settings designation message is sent (e.g., an "apply new settings now" button that must be selected before the message is sent, a dialog box with an apply settings button, etc.) and/or to authenticate the administrator if/as desired.

In response to receiving an AED settings designation message, the management server 20 determines whether the target AED(s) are already in the desired state. Block 1810. Typically, this is done by checking the management database 290 to determine whether the target AED is in the desired state. However, in other embodiments, the target AED may be queried to report its current state or when appropriate, this step check may be skipped. When the desired setting is associated with one or more labels, the management server accesses the management database 290 to determine which AEDs are associated with the designated label(s). The management server then makes the determination of block 1810 for each of the target AEDs associated with such label(s).

For any target AED that is not already in the desired state, the management server sends an appropriate Set AED Settings command to the target AED. Block 1812. There are a number of ways that the management server can communicate the Set AED Settings command to the target AED. In some circumstances, there may be an established connection with the target AED or the management server may be able to directly establish such a connection. In such cases, the management server may communicate the command over the open connection. However, for security and/or power savings reasons, the management server may not be able to directly establish a connection with the AED. Rather any connection needs to be initiated by the AED. In some such circumstances, the management server is configured to "ping" the AED, requesting that it check-in with the server. For example, technologies such as Extended Discontinuous Reception (eDRX) which is commonly used in cellular networks allows a server to send a check-in message in the form of a paging message to a device (in this case the AED). The AED periodically wakes up to listen/check for paging messages. If when a check-in paging message is received, the AED establishes a connection with the management server and the Set AED Settings command can be sent over that connection. In still other embodiments, the AED is configured to periodically open a connection with the management server to report information. For example, after every self-test, the AED may establish a connection with the management server to check for messages and send an updated status message. In either of these cases, the Set AED Settings command can be communicated when an appropriate connection is established by the target AED. Of course, the same approach may be used in transmitting any of the information, content, settings or commands from the management server to a target AED described herein.

Upon receipt of the Set AED Settings command, the target AED implements the commanded setting. Block 1815. Preferably the target AED reports back to the management server when the setting has been updated and the management server updates the target AED record in the management database 290 accordingly so that the management server maintains a good record of the current state of the target AED. When desired, the management server can also send a confirmation message to the administrator that indicates that the desired settings change has been implemented in the target AED or such a notification can be displayed at an appropriate location in the management platform user interface.

In embodiments in which the AED includes a base defibrillator unit and an interface unit that serves as a gateway to a base defibrillator unit, when the setting only applies to an interface unit, the commanded setting change is preferably implemented by interface unit alone without involving or impacting the base defibrillator unit in any way. When the setting applies in full or in part to the base defibrillator unit, the interface unit informs the base defibrillator unit of the relevant commanded settings change.

It should be appreciated that the management server 20 can be notified of desired settings for an AED in other ways. As previously mentioned, an AED can be associated with a label at any time. When that occurs, any content and/or settings associated with the label will be automatically transmitted/applied to the newly associated AED. A representative flow 1900 for applying settings and/or delivering content to an AED based on a label assignment is described with reference to FIG. 19.

The flow is triggered when an administrator assigns an existing label to one or more target AEDs. Block 1903. In response to the label assignment being made/committed, the administrator's device user interface transmits a grouping or "label assignment" message to the management server indicating that the selected label has been assigned to the target AED(s). Block 1906. Upon receiving the label assignment message, the management server 20 updates the records associated with the target AED(s) and the label in management database 290 to reflect the new label assignment. Block 1909. The management server also identifies any content and/or settings that are associated with the selected label. Block 1912. This can readily be done by checking the label record for the selected label in the management database.

If/when there are settings or content associated with the selected label, the management server will check the management database to determine whether the target AED is already in the various setting states and/or already has the content associated with the assigned label. This can be accomplished by checking the target AED record(s). To the extent that any new settings are to be applied to any target AED, the management server sends appropriate Set Settings commands to such target AED. Similarly, to the extent that any new content is to be provided to a target AED, the management server transmits such content to such target AED. Block 1915. The settings commands and content may be delivered to the target AED in a single session, separately or in groups as deemed appropriate. Upon receiving the Set Settings command(s) and/or content, the receiving AED will apply the desired settings and install the desired content as instructed. Block 1918. The target AED reports back to the management server when updated settings have been applied and/or when the new content has been installed and the management server updates the management database records accordingly.

The general approaches set forth above can be used to implement a wide variety of settings changes, including, for example: (i) designating the desired operational power mode for the AED; (ii) setting a desired broadcast mode; (iii) setting a desired training sequence for use when the AED is in a training mode or a desired training mode; (iv) setting different defibrillation shock and/or CPR protocols; (v) lock the AED commands (e.g., placing the AED in a mode in which it will not accept any setting changes directly on the AED itself); (vi) turning various services on or off (e.g., location services, Wi-Fi service, cellular service, Bluetooth service, etc.); (vii) enabling or disabling the screensaver feature; etc. The same general approach can be used in situations in which the administrator must supply some information together with the command, as for example set security code command in which a security code (e.g., PIN code or password) provided by the administrator must accompany the command.

Incident Reports

In some embodiments, the management server 20 is configured to create an AED incident report based on information received from the AED. Preferably, the incident report is made available to interested parties both: (a) in real-time during the incident; and (b) after the AED's use has been completed. Making incident reports available in real-time during an incident and readily available thereafter offers a number of advantages that we believe can help improve cardiac arrest outcomes.

Referring next to FIG. 10, a representative incident report 1000 is illustrated. Although a particular report style is described, it should be appreciated that the content and layout of the incident report may be widely varied to meet the needs of any particular constituent group. The illustrated incident report 1000 includes an incident information section 1002, an event log 1004 and an ECG section 1006. The incident information section 1002 includes a number of fields that provide useful information about the incident. In the illustrated embodiments, the incident information fields include a Date field 1010, an Emergency Services Called Time field 1012, an AEDs Dispatched field 1014, an Incident Accepted field 1016, an AED In Route field 1020, an AED Powered On field 1018, a Pads Placed field 1022, an AED Powered Off field 1024, an Incident ID field 1026 an AED Serial Number field 1028 and a Number of Shocks Delivered field 1030.

Many of the described fields are self-explanatory. For example, the date field 1010 includes a date identifier 1011 that indicates the date of the incident. The Emergency Services Called Time field 1012, the AEDs dispatched field 1014, the Incident Accepted field 1016, the AED Powered-On field 1018, the Pads Placed field 1022 and the AED Powered-Off field 1024 each contain timestamps that indicate the time that the associated events occurred.

Several of the timestamps are provided by the AED used in the incident and reported to the management server 20 based on events detected by the AED. For example, the AED Powered-On field 1018 includes a Powered-On timestamp 1019 that indicates when the AED was turned on. The AED Powered Off field 1024 includes a Powered Off timestamp 1025 that indicates when the AED was turned off. The Pads Place field 1022 includes a Pads Placed timestamp 1023 that indicates when the AEDs electrode pads were placed on the patient. Typically, AEDs are configured to determine when the pads have been placed. Often this is based on a sensed impedance (e.g., the detected impedance between the pads being within a range expected for pad placement) and/or the detection of a cardiac rhythm. The various AED usage-based timestamps can be provided by the AED as part of incident status messages, by specific notifications sent when the corresponding event is detected, or in other suitable manners.

Several of the other fields in the incident report are more related to emergency response and are therefore more relevant when the AED is used in a responder network type scenario. By way of background, the Applicant has described AED inclusive responder networks that can be activated by Public Safety Answering Point (PSAP) telecommunicators (e.g., 911 dispatchers) and others/other systems. When activated, the responder network server sends nearby incident notifications to AEDs and/or volunteer responders indicating that there is a nearby cardiac arrest incident for which the AED and/or the volunteer responder's assistance may be useful. By way of example, U.S. Pat. No. 10,580,280 (P014B); U.S. Pat. No. 10,565,845 (P014A); U.S. Pat. No. 10,957,178 (P014X1); U.S. Pat. No. 11,138, 855 (P014AX2); U.S. Pat. No. 11,210,020 (P021); U.S. Pat. No. 11,645,899 (P014X3); U.S. Pat. No. 11,640,755 (P021X1); U.S. Pat. No. 11,869,338 (P023) and U.S. patent application Ser. No. 17/903,642 (now U.S. Publication No. 2023/0008570) (P025), each of which is incorporated herein by reference, describe a few such systems. In some such implementations, the computer aided dispatch (CAD) system has an interface (such as an activate AED network GUI widget) that allows the dispatcher to activate the responder network with minimal effort.

When an AED is used in the context of a responder network response, the responder network server will have background information about the response that can be quite helpful to medical personnel and/or emergency services and/or other interested in tracking or understanding the response. In some implementations, the AED management platform server infrastructure 20 also functions as the responder network server and thus inherently has such information. In other implementations, the responder network server may be configured to communicate any relevant information to the AED management server. When available, such information can be included in the incident report, which may then be made available to medical personnel and others both during and after the incident as will be discussed in more detail below.

In the illustrated embodiment, the emergency response related fields include the Emergency Services Called Time field 1012, the AEDs Dispatched field 1014, and the Incident Accepted field 1016 and the AED In Route field 1020.

The Emergency Services Called Time field 1012 includes an Emergency Services Call timestamp 1013 that indicates the time that the PSAP first received a call about the incident. In many cases, the time that a call to emergency services (e.g., a 911 call) was made will be the first verifiable times associated with an incident. As such the original emergency services call time may be useful in estimating how long the patient was in cardiac arrest before defibrillation occurred-which can be helpful to treating physicians and others in making treatment decisions. It should be appreciated that the emergency services call receipt time is information that PSAPs routinely capture. Therefore, it can readily be provided to the responder network server by the PSAP. In some implementations the responder network API and the PSAP integration are designed so that the emergency services call receipt time is included in the responder network activation request (e.g., as a parameter in the activate responder network function call passed from the PSAP CAD system to the responder network server in order to activate the responder network).

The Dispatch timestamp 1015 provided in AED Dispatched field 1014 indicates the time that a request was made to activate the AED inclusive responder network. This can be a timestamp received as part of the activation request, or a timestamp created by the responder network server when the activation request is made.

The Incident Accepted timestamp 1017 provided in Incident Accepted field 916 indicates the time that a responder "accepted" the incident indicating their willingness and ability to respond to the incident. As described in some of the incorporated patents, the AED preferably has an interface that allows a volunteer responder that hears or sees a nearby incident alert generated by the AED to "accept" the incident—e.g., by selecting an "Accept Incident" button displayed on a touch sensitive display screen on the AED. Accepting the incident causes an Incident Accepted message to be sent from the AED to the responder network server so that the responder network server knows that someone is taking the AED to the incident. It may also cause a map to be rendered on the AED's display screen to give the responder directions to the incident as described in some of the incorporated patents. In some embodiments, the responder network server creates the Incident Accepted timestamp based on the time it receives the corresponding Incident Accepted message. In other embodiments, the timestamp may be provided by the AED based on the time it received a responder's acceptance of the incident.

The AED In Route field 1020 includes an In Route indicator 1021 that is intended to indicate that a responder has accepted the incident and is currently taking the incident to the incident. The information can be conveyed in a variety of ways, as for example by wording stating something like: "AED IN ROUTE TO INCIDENT" when an AED is being taken to the incident. Once the AED has arrived at the incident scene, the message can be changed to an appropriate alternative message-such as "Arrived," etc.

It should be appreciated that the system can be configured so that the responder network server will generally know in real time when the AED is in route and when it has arrived at the incident scene. For example, the responder network server will know when an AED (or volunteer responder) has accepted the incident and is taking an AED to the incident based on the reception of the Incident Accepted message. The responder network server would also typically know about when the AED has arrived at the scene of the incident through any of a variety of mechanisms. For example, in some implementations/circumstances a responder may be prompted to select an "Arrived" GUI widget displayed on the AED's touch screen when they arrive at the incident scene. Selection of the Arrived GUI widget then triggers an Arrived message to be sent from the AED to the responder network server. Alternatively, or additionally, in many implementations various usage events may trigger a message being sent to the responder network server that shows the AED is now in use and as such can be presumed to have arrived at the incident scene. For example, in some implementations, a Powered-On message is sent from the AED to the responder network server when the AED is turned on and/or an Electrode Pads accessed message may be sent when the AED's electrode pads have been accessed (as for example by opening an electrode pad cartridge). Of course, there are many other events that can trigger messages that can be interpreted by the responder network server as indicating that the AED has arrived at the incident scene and/or is in active use. Timestamps for any or all of these events may be provided in the incident report.

Although a few specific dispatch event related timestamps and events are shown in FIG. 10, it should be appreciated that in other embodiments, more, less and/or other relevant dispatch related event times can be provided in the incident report 1000. One such example is the time that a nearby incident notification was initially sent to or received by the AED.

Of course, there are many circumstances in which an AED may be used that are not responsive to a dispatching event. In such circumstances, the Emergency Services Called field 1012, the AEDs Dispatched field 1014, the Incident Accepted field 1016, the In Route field 1020 and any other dispatch related fields may be left blank or a placeholder such as N/A may be used.

In the discussions above and below, several references are made to actions taken by and/or information known to a responder network server. It should be appreciated that the AED management server may itself function as the responder network server and therefore inherently have such information. Alternatively, when the responder network server and the AED management server are separate systems, the responder network server may transmit the relevant information to the AED management server in real time as such information is received.

The sample incident report illustrated in FIG. 10 shows dispatch information that is relevant when the volunteer responder response was initiated by a PSAP. There may be times when the AED inclusive responder network is activated (e.g., notified of an incident) directly or indirectly by a monitoring device (as described, for example, in incorporated U.S. Pat. No. 17,100,313 and Ser. No. 17/155,853). In such circumstances the dispatch related information may be adjusted to reflect relevant information that is available in such systems. For example, when a monitoring system detects an incident, the monitoring system will typically know the time that the incident was detected. As such, the incident detection time can be used in place of or in addition to the emergency services call time. Of course, the incident detection time gives the viewer an even better view of exactly when the incident occurred and how much time passes before defibrillation occurs.

Monitoring devices may also have other relevant information about the incident that may be included in the incident report if transmitted to the responder network server. For example, if the monitor detected a fall together with no movement after the fall and/or detected an abnormal heart rhythm of agonal breathing, each of the events detected, and (when available) the time detected, can be identified in the incident report.

In the illustrated embodiment, the incident information section 1002 includes several other fields, including an Incident ID field 1024, a Serial No. field 1026 and a Shocks Delivered field 1028. The Incident ID field 1024 provides an identifier (the Incident ID) 1025 that uniquely identifies the incident. The Serial Number field 1026 reports the serial number 1027 of the reporting AED. The Shocks Delivered field 1028 indicates the total number of shocks delivered during the incident.

The event log 1004 provides a list of noteworthy events that occurred during use of the AED. In the illustrated embodiment, the events are listed in time order with an indication of the amount of time that elapsed between the time that the AED was powered on, and the relevant event occurred. The specific events that are listed in the event log may vary based on system designer selections and/or user selections preferences. By way of example, representative events that may be identified in the event log include: (1) pad placement and/or removal; (2) each shock that is delivered; (3) classification determinations—e.g., determinations that that a shock is not advised or that a shock is advised (the latter is not shown); (4) indications of user interactions with the AED such as selecting a child or adult operating mode, or selecting a different language to be used for operating instructions. When a shock is delivered, the nature and/or characteristics of the shock delivered are also preferably provided. For example, the amount of energy delivered in the shock, (e.g., 150 joules, 180 joules, 50 joules, etc.) may be provided. In some implementations, the shock waveform used (e.g., biphasic) and/or a characterization of whether the shock was intended for an adult or pediatric patient, and/or other relevant information about the shock characteristics may also or alternatively be provided.

The ECG section 1006 provides the ECG that is detected by the AED. The portions of the ECG represented in the ECG section 1006 may vary based on a variety of factors including what information is available to the management server and design and/or user preferences. When the entire ECG recorded by the AED is available, the entire ECG may be provided as part of the incident report. Alternatively, the ECG section 1006 may include only selected portions of the ECG. Preferably the ECG is annotated to show where various events of interest occurred relative to the ECG. For example, annotated events may include (but are not limited to) events such as: (1) pad placement 1041; (2) the ECG segments that were used for the heart rhythm classification 1043, 1044 (e.g., the segments used to determine whether the patient has a shockable or non-shockable heart rhythm); (3) shock delivery 1046; (4) user interactions, 1048 etc. As mentioned above, user actions may include items such as selecting an operating mode (e.g., adult vs. pediatric) or selecting an instruction language. When multiple ECG segments are used for classification, then marking each such classification segment may be desired. For example, in the illustrated embodiment a primary classification 1043 was done on a first ECG segment to determine whether the patient's heart rhythm is shockable, and a confirmatory classification 1044 was done on a second segment immediately before the shock is delivered to verify that the patient is still experiencing cardiac arrest. Both of these segments are marked by shading and appropriate labeling. When desired, the shock delivery annotation of the ECG can also include selected parameters of the delivered shock such as energy delivered, waveform used, etc.

As discussed above, whenever possible, the AEDs 10 preferably transmit incident status messages to the management server 20 in real-time during use in an emergency incident. In some implementations the AED may also transmit selected segments or the entirety of the detected ECG to the management server. In other implementations the ECG is only sent to the management server after the event is over.

When the AED management server 20 has information about the incident in real time, it can provide the incident report to interested parties in real-time during the incident. Thus, the incident report 1000 can be rendered in real time or after the incident is over. By way of example, the incident may be rendered in a web page served by the management server (or other suitable server), in an App that communicates with the server, or using any other suitable rendering mechanism. Preferably, the incident report is also made available in a downloadable format such as a PDF. When rendered in real-time, the incident reports preferably contain whatever relevant report information the management server currently has, and the rendered incident report can be updated as the incident progresses.

There are several use cases for the real-time incident reports. Initially, the incident report may be made available to the administrator(s) and users associated with the AED's account via the management platform. Thus, a remote administrator can track the incident in real-time and act accordingly. The incident can also be made available to medical personnel or first responders that will be responsible for treating the patient both in real-time during use of the AED and after the AED's use has been completed.

An incident report server (which whether it is a separate system of the same physical machine is referred to herein as part of the management server infrastructure 20) may include a health care provider portal that allows health care providers and first responders (e.g., emergency medical technicians, paramedics, etc.—collectively referred to as EMTs herein) to access defibrillator incident reports via a web-based portal. One user interface suitable for facilitating medical personnel access to the incident report is illustrated in FIG. 13A. Referring initially to FIG. 13A, to access a report, the interested party that has the incident ID may access the incident report by way of an incident query page 1302 of the incident report portal 1300. The query page includes a search dialog box 1303 that the incident ID is entered into. After the incident ID is entered, search button 1305 is selected and the incident report server serves a brief summary of the incident report, such as the incident summary page 1310 shown in FIG. 13B.

The incident summary page 1310 includes some basic information about the incident. In the illustrated embodiment, the summary information includes: (i) the Incident ID; (ii) the date and time of the incident; (iii) an indication of the number of shocks delivered; (iv) the AED used; and (v) a summary of the most recent classifications performed by the AED. Although specific summary information is shown, it should be appreciated that the actual contents of the summary may vary widely.

The summary page 1310 also includes a Download Incident Report button or link 1320 which, when selected, cause the incident report server to deliver the incident report to the viewers browser. In some embodiments, the Incident Report is provided as a PDF, although other formats can be used as well.

As previously mentioned, incident status messages transmitted to the management server 20 (and elsewhere) preferably include the incident identifier. The incident identifier can be conveyed to appropriate medical personnel or EMTs by any available channel. With the incident identifier in-hand, the medical personnel/EMT can access the incident report via the incident report portal 1300. There are a number of ways that an interested party can obtain the incident identifier. For example, if the PSAP telecommunicator has the Incident ID, they can convey the identifier to the first responders that have been dispatched to the incident. That gives a passenger first responder the ability to obtain and review an in-progress incident report to get a feel for the situation before they arrive at the scene of the incident-which can help prepare them for responding to the incident.

The PSAP telecommunicator can obtain the incident ID by a variety of pathways as well. For example, if/when the AED is communicatively coupled to the PSAP, an appropriate portal (e.g., an emergency services interface (ESI) portal or responder network portal) on the dispatcher CAD system may receive the incident ID from the AED. In another example, a caller making a call to emergency services (e.g., a 911 call) can verbally report the incident ID to the telecommunicator. The caller at the incident scene may receive the incident ID via an app that receives status message advertisements broadcast by the AED (as described in incorporated U.S. Pat. No. 11,077,312 (P016B)), by viewing a display screen on the AED or in other suitable manners.

Medical personnel responsible for treating the patient can also greatly benefit from seeing the incident report. For example, the incident report can provide emergency room personnel with vital information about the incident even before the patient arrives at the hospital, which can provide a much better understanding of the patient's likely condition when they arrive at the hospital. The incident ID can be provided to the hospital in a number of ways. For example, in some cases, a party talking to an emergency room administrator may be able to provide the incident ID verbally. In other scenarios, the incident ID (and/or the entire incident report) can be included in an EMS electronic patient care record (ePCR record) provided by EMS as part of their patient hand-off to emergency room personnel. Some methods and systems for integrating incident IDs and incident reports into an ePCR record are described in U.S. Pat. No. 11,869,338 (P023) which is incorporated herein by reference.

Th incident reports can also be useful for emergency response officials and others that are evaluating the effectiveness of emergency response.

Training Reports

In some embodiments, training reports are also supported. When the AED is used in a training report, a training report somewhat similar to the Incident Reports may be generated that include timestamps and usage events of interest from the training session. The training reports can be used to provide feedback to both the trainer and the trainee and can also provide evidence of training with the AED which may be desired or required by various programs.

Device Setup

Referring next to FIG. 11, an AED setup processed 1100 that is enabled by the management platform will be described. When a new AED is manufactured, the manufacturer causes a new device (AED) record to be created in the management database 290. Block 1103. The record may be created: (i) automatically based on a triggering event; (b) semi-automatically by scanning the AED's serial number; (iii) manually by an operator; or (iv) by other suitable methods. One automatic process that is based on modular AED that includes a base defibrillator unit and an interface unit that is attached to the base defibrillator unit will be described.

In the described embodiment, when an interface unit is first attached to the base defibrillator unit, the interface unit will detect that it has a connection with the AED and will receive a status message from the AED. The interface unit then transmits a status message to the management server that includes status information from both the base defibrillator unit and the interface unit. The status message includes the AED's serial number as well as the serial number of the interface unit. When the management server receives the status message it will see that it does not yet have a record for that AED and will therefore generate a new record for the AED (including both the base defibrillator unit and its associated interface unit). The newly created record is then populated as appropriate with the device information that is included in the status message. This includes device specific information such as the AED's serial number, installed software version, pad cartridge serial number, and pad expiration date. If the AED has a replaceable battery, the battery's serial number, manufacture date and expiration date are also known and added when the record is created. Preferably the management database is integrated with the manufacturing records system so that other relevant device information that may not be part of the status messages, such as the manufacturing date of the AED and the pad cartridge manufacture date are automatically entered into the device record as well.

At some point the AED is sold or otherwise assigned for delivery to a customer. At this stage, the device record is updated to associate the device record with the owner. This association is preferably done by the selling entity, which may be the manufacture itself, or a distributor. In some embodiments, the owner association is made semi-automatically by a shipping clerk scanning the AED and associating it with a particular purchase order. The purchase order, in turn, is associated with the purchaser, i.e., the soon-to-be owner. Thus, various customer related information including the owner's identity, shipping address and contact information, any of which is relevant to the device record can be associated with the AED record at that time. Once the owner's information is associated with the record, the device record can be made available to the owner in the management platform—which in many cases will be before the customer even receives their device. When the device record is made available prior to delivery of the AED, certain information such as its current location, and any information available to the management platform based on testing as part of the manufacturing process such as test incident reports, may be blocked.

When the owner has other AEDs, the owner's record will frequently also designate one or more default administrators. Once the device record is associated with an owner entity, any designated default administrator(s) will have access to the device record and can therefore configure the AED at any time thereafter—which may even be before the AED has shipped. When the purchasing entity has other AEDs in the system, they may have also already set certain device preferences and/or designated certain content to apply to all of their AEDs. Any such preferences, content, etc. are thus automatically associated with the newly purchased AED simply by associating the owner with the AED—without requiring any new input by the administrator, the manufacturer, or anyone else.

In some embodiments, the AED is synchronized with the management server (Block 1109) after the customer has been associated with the AED, but before it is shipped (Block 1112). When the AED is synchronized, any custom content that has been associated with the AED at that point will be downloaded and installed on the AED. That can include any designated wireless certificates, any custom screen saver content, etc. If the customer requires a different software version for their AEDs, the desired software version may be installed at this point as well. For example, the customer may desire that the AED's instructions be rendered in a different language than the language(s) utilized in the base software version originally installed during manufacture. In such cases, the software update may install a software version that renders audio and visual content in the desired language. In another example, in some circumstances a particular customer may prefer that their AEDs utilize a different approved shock sequence protocol than the shock protocol utilized by the software version originally installed during manufacture. Again, the updated/customer preferred software may be utilized automatically installed at this stage. In yet another example, in many of the described embodiments, the AED has GPS and other geolocation determining capabilities as well as location reporting capabilities. Some customers may prefer that their AEDs not include such location determining and reporting capabilities and a different software version that does not implement the location determining or reporting functionality may be installed based on those designated preferences as well.

Once the record is associated with its purchaser, the purchaser or a default administrator may then utilize the management platform to set up the device record and configure the AED as desired. This can include inputting device information (block 1123), applying labels to the device record (block 1125), setting preferences (block 1127), and associating desired content with the AED (block 1129). The owner/administrator inputted device information (Block 1123) includes information such as the AED name 421, its assigned location 422, its assigned users 411, and any placement descriptions 426 and/or return instructions.

The labels are a generic construct so the labels created and/or applied by an administrator (Block 1125) can reflect any hierarchy that the entity finds useful. In a situation where the owner has multiple facilities, separate labels can be assigned for each facility (e.g., Headquarters, R&D Office, Castorland Plant, etc.). In a situation where the owner has different types of uses, separate labels can be assigned for each type of use. In a situation where different user categories, administrators or administrative groups may have responsibilities for different AEDs within a fleet, separate labels can be assigned for each such group. For example, in an AED network managed by a city EMS department, some AEDs may be placed with police officers, others with EMTs/paramedics, others with firefighters and others with volunteer responders. In such circumstances, separate labels can be provided for each of these groups. Although only a few examples have been given, the administrator is free to define labels in any way that they see fit for their particular application.

The labels can be helpful for both identifying AEDs associated with any particular group (label) and for assigning common preferences, and/or assigning common content to multiple devices sharing the same label.

The management platform also gives the administrator the opportunity to set any of a variety of preferences. Block 1127. These include the Permanent or Mobile designation 424, the Private or Public designation 441, the Nearby Incident alerts enabled designation 444, and the Notify 911 designator 446. As previously discussed, these preferences can be assigned on an individual AED basis, assigned based on labels, applied to all managed AEDs, or assigned in other suitable ways.

Administrator defined content for the AEDs includes items such as wireless certificates, screensaver content, etc. Like preferences, return instructions and other items, the administrator defined content can be assigned individually, in groups (e.g., using labels), or to the entire managed fleet as is appropriate for any particular circumstance.

Any device information, labels, preferences, and user specified content that is entered by the administrator is passed/uploaded to the management server 20 and recorded in the management database 290 and will be reflected in the information presented in the management platform such as the dashboard 300 and device status pages 400. To the extent that any content is specified to be loaded onto an AED, it will automatically be loaded and installed at the first appropriate opportunity. Thus, if the content is designated before the AED is shipped (Block 1112), it can (and typically will) be loaded/installed before the AED is shipped. Alternatively, if the content is designated after the AED has been received by the customer, but before it has been placed, the designated content may be loaded/installed before the AED is placed (e.g., while it is still in the possession of the receiving administrator). If the content is designated after the AED has been placed at its desired location (which will sometimes be remote from the administrator), the designated content may be loaded/installed at its designated location.

To help facilitate the entry of delivery of settings and content, the management platform optionally includes a CVS upload tool that allows customers to upload a file containing information about themselves or their organization. Such a file may contain information about the authorized users and their contact information, locations, AED names, preferences for different settings, etc. As should be apparent from the foregoing, the associated content and settings can be stored in the management server and automatically applied to the associated AEDs whenever such CVS upload files are received by the management server, Since in some embodiments, the AEDs are highly connected devices having Wi-Fi, cellular, Bluetooth and optionally satellite connectivity, there are many pathways by which user defined content can be conveyed to the AED. The content can be delivered relatively directly (e.g., via a cellular, Wi-Fi or satellite communications network) or via an intermediary (e.g., a passing smart phone or tablet computer) using a short-range communication protocol such as Bluetooth, near-field communication or others as described in incorporated U.S. Pat. No. 11,077,312 (P016B).

Modular AED

Referring next to FIG. 15, a modular defibrillator architecture in accordance with one embodiment that is suitable for use in conjunction with the described management platform. The illustrated architecture is well suited for use in automated external defibrillators (including both semi-automated and fully automated defibrillators) although it may also be used in manual defibrillators and hybrid defibrillators that may be used in either automated or manual modes.

The core of the modular defibrillator system is a base defibrillation unit (base unit) 110. The illustrated base defibrillation unit 110 is a fully functional AED that is configured such that its functionality can be supplemented by attaching an interface unit 200 to the base unit. The base unit 110 independently functions as an AED both with and without the attached interface unit 200. In this embodiment, interface unit 200 includes one or more processors, a touch sensitive display screen 220, a communications unit and preferably its own power storage unit (e.g., battery). The touch sensitive display facilitates user interactions with the interface unit and, as appropriate, indirect interactions with the base unit. The communications unit facilitates communications with external systems and/or devices using a variety of different communications technologies and protocols, as for example, Wi-Fi communications, cellular communications, satellite communication and short-range wireless communications technologies (e.g., Bluetooth, Near Field Communication (NFC), etc.) By way of example, U.S. Pat. No. 10,773,091 (P006E), U.S. Pat. No. 10,737,105 (P006A), U.S. Pat. No. 11,452,881 (P016A), U.S. Pat. No. 11,077,312 (P016B) and U.S. patent application Ser. No. 17/007,838 (P019B), each of which is incorporated herein by reference, describe details of a variety of such modular defibrillator architectures.

FIG. 16 is a block diagram illustrating one representative electronics control architecture and associated components suitable for use in the base defibrillator unit 110. In the illustrated embodiment, the electronic components include a defibrillator controller 130, memory 133, a wireless communications module in the form of Bluetooth module 134, a charging power regulator 140, a voltage booster 145 (which may have multiple stages), a high voltage capacitor 1150 for temporarily storing sufficient electrical energy suitable to provide a defibrillation shock, discharge control circuitry 1160, pad related sensing circuitry 1162 and relays 1169, power storage unit 1170, battery regulator 1193, status indicator(s) 1175, speaker(s) 1180 and one or more electrical connectors (e.g., interface connector 1190, mobile connector port 1195, charger connector (not shown), etc.). The charging power regulator 140 and voltage booster 145 which cooperate to control the charging of the shock discharge capacitor 1150 are sometimes referred to herein as a charging circuit.

The defibrillator controller 130 is configured to control the operation of the base defibrillator unit and to direct communications with external devices, as appropriate. In some embodiments, the defibrillator controller includes a processor arranged to execute software (some or all of which may take the form of firmware) having programmed instructions for controlling the operation of the base unit, directing interactions with a user and communications with external components. The software may be installed on the memory 133. Although the singular term memory is often used herein, it should be appreciated that the memory may be divided into multiple different parts which take any suitable form or combination of forms (e.g., various types of RAM, ROM, PROM, EEPROM, etc.) Unless the context suggests otherwise, references to "memory" herein are intended to cover all suitable forms and combinations of physical memory. Similarly, although the singular term "processor" is often used herein, it should be appreciated that any appropriate number of processors and/or processing cores can be utilized and unless the context suggests otherwise, references to "processor" herein are intended to cover processing units composed of one or more physical processors or processing cores.

The base defibrillator unit 110 may optionally be configured so that it is capable of drawing power from certain other available power sources beyond power storage unit 1170 to expedite the charging of shock discharge capacitor 1150. The charging power regulator 140 is configured to manage the current draws that supply the voltage booster, regardless of where that power may originate from. For example, in some embodiments, supplemental power may be supplied from a mobile device coupled to mobile connector port 1195 or from a portable charger/supplemental battery pack coupled to charger connector 1197.

The voltage booster 145 is arranged to boost the voltage from the operational voltage of power storage unit 1170 to the desired operational voltage of the discharge capacitor 1150, which in the described embodiment may be on the order of approximately 1400V-2000V (although the defibrillator may be designed to attain any desired voltage). In some embodiments, the boost is accomplished in a single stage, whereas in other embodiments, a multistage boost converter is used. A few representative boost converters are described in the incorporated U.S. Pat. No. 10,029,109 (P001A). By way of example, in some embodiments, a flyback converter, as for example, a valley switching flyback converter may be used as the voltage booster 145—although it should be appreciated that in other embodiments, a wide variety of other types of voltage boosters can be used.

A voltage sensor 1151 is provided to read the voltage of the capacitor 1150. The voltage sensor 1151 may take the form of a voltage divider or any other suitable form. This capacitor voltage reading is utilized to determine when the shock discharge capacitor 1150 is charged suitably for use. The sensed voltage is provided to controller 130 which determines when the capacitor 1150 is charged sufficiently to deliver a defibrillation shock. The capacitor 1150 can be charged to any desired level. This can be useful because different defibrillation protocols advise different voltage and/or energy level shocks for different conditions. Furthermore, if the initial shock is not sufficient to restart a normal cardiac rhythm, some recommended treatment protocols call for the use of progressively higher energy impulses in subsequently administered shocks (up to a point).

The discharge circuitry 1160 may take a wide variety of different forms. In some embodiments, the discharge circuitry 1160 includes an H-bridge along with the drivers that drive the H-bridge switches. The drivers are directed by defibrillator controller 130. The H-bridge outputs a biphasic (or other multi-phasic) shock to patient electrode pads 116 through relays 1169. The relays 1169 are configured to switch between an ECG detection mode in which the patient electrode pads 116 are coupled to the pad related sensing circuitry 1162, and a shock delivery mode in which the patient electrode pads 116 are connected to H-Bridge to facilitate delivery of a defibrillation shock to the patient. Although specific components are described, it should be appreciated that their respective functionalities may be provided by a variety of other circuits.

The pad related sensing circuitry 1162 may include a variety of different functions. By way of example, this may optionally include a pad connection sensor 1164, ECG sensing/filtering circuitry 1165 and impedance measurement filter 1166. The pad connection sensor is arranged to detect the pads are actually connected to (plugged into) the base defibrillator unit 110. The ECG sensing/filtering circuitry 1165 senses electrical activity of the patient's heart when the pads are attached to a patient. The filtered signal is then passed to defibrillator controller 130 for analysis to determine whether the detected cardiac rhythm indicates a condition that is a candidate to be treated by the administration of an electrical shock (i.e., whether the rhythm is a shockable rhythm) and the nature of the recommended shock.

When a shockable rhythm is detected, the controller 130 directs the user appropriately and controls the shock delivery by directing the H-bridge drivers appropriately.

In some embodiments, the power storage unit 1170 takes the form of one or more batteries such as rechargeable Lithium based batteries including Lithium-ion and other Lithium based chemistries, although other power storage devices such as one or more supercapacitors, ultracapacitors, etc. and/or other battery chemistries and/or combinations thereof may be used as deemed appropriate for any particular application. The power storage unit 1170 is preferably rechargeable and may be recharged via any of a variety of charging mechanisms. In some embodiments, the power storage unit 1170 takes the form of a rechargeable battery. For convenience and simplicity, in much of the description below, we refer to the power storage unit 1170 as a rechargeable battery. However, it should be appreciated that other types of power storage devices can readily be substituted for the battery. Also, the singular term "battery" is often used, and it should be appreciated that the battery may be a unit composed of a single battery or a plurality of individual batteries and/or may comprise one or more other power storage components and/or combinations of different power storage units.

In some embodiments, the base defibrillator unit 110 is capable of drawing power from other available power sources for the purpose of one or both of (a) expediting the charging of shock discharge capacitor 1150 and (b) recharging the power storage unit 1170. In some embodiments, the battery can be recharged using one or more of the externally accessible connector ports 1195, a dedicated charging station, a supplemental battery pack (portable charger), an interface unit 200, etc. as will be described in more detail below. When wireless charging is supported, the base defibrillator unit may include a wireless charging module 1174 configured to facilitate inductive charging of the power storage unit 1170 (e.g., using an inductive charging station 294, or other devices that support inductive charging, as for example an inductively charging battery pack, a cell phone with inductive charging capabilities, etc.).

The base unit also includes a number of software or firmware control algorithms installed in memory 133 and executable on the defibrillator controller. The control algorithms have programmed instructions suitable for controlling operation of the base unit and for coordinating the described broadcasts, as well as any point-to-point communications between the base unit 110 and the interface unit 200, connected devices, and/or any other attached or connected (wirelessly or wired) devices. These control routines include (but are not limited to): communication control algorithms, heart rhythm classification algorithms suitable for identifying shockable rhythms; capacitor charge management algorithms for managing the charging of the discharge capacitor; capacitor discharge management algorithms for managing the delivery of a shock as necessary; user interface management algorithms for managing the user instructions given by the defibrillator and/or any connected user interface devices (e.g. interface unit 200, mobile communication device 105) during an emergency; battery charge control algorithms for managing the charging of power storage unit 1170; testing and reporting algorithms for managing and reporting self-testing of the base unit; software update control algorithms and verification files that facilitate software updates and the verification of the same.

In many installations, an AED will be expected to be stored for long periods of time without being plugged into power and therefore relying solely on battery power.

Accordingly, it is important to minimize the power drain as much as possible during this time. In some embodiments, the defibrillator controller is configured to shut down power to all electrical components (including itself) except for (a) a real time clock (not shown), (b) the Bluetooth module 134, and (c) a power controller (not shown) when the AED is in the standby (resting) mode. In some embodiments, the clock and/or the power controller are integrated into the Bluetooth module 134 or an I/O adaptor board that includes the Bluetooth module. The clock is configured to periodically send a status check alarm to the power controller which wakes the power controller up from a sleep mode when the power controller is separate from the Bluetooth module. In response to the status check alarm, the power controller restores power to the entire system. Once power is restored, the defibrillator controller 130 performs a status check and instructs the Bluetooth module 134 to update the standby status message 150 as appropriate. After the status check is performed, the defibrillator controller will again shut down power to all electrical components except the clock, the Bluetooth module 134 and the power controller. The status check alarms can be generated at any desired intervals, as for example, once each day.

With the described power management scheme, the Bluetooth module 134 can continue to broadcast standby status messages even when the AED is powered down.

If the Bluetooth Module 134 makes a connection while the AED is in the standby mode, it sends a message to the power controller, which in turn, powers on the system, thereby allowing the defibrillator controller or other suitable component to communicate with the connecting device. Thus, the AED can effectively be woken up via a Bluetooth connection request. Of course, the power controller is also configured to power the system when a user presses the AED's "ON" button or otherwise activates the AED.

In other embodiments, one or more of the electrical components of the AED, such as the defibrillator controller 130, can be placed in a "sleep" mode rather than being turned off when the AED is in the standby mode. However, a significant advantage of actually turning the defibrillator controller and the bulk of the AED's electrical components off as opposed to placing them in a sleep mode is that it eliminates the power draw associated with the sleep mode, thereby potentially extending the AED's shelf life. It should be appreciated that the power controller/power down approach can be also used with AEDs that don't incorporate a Bluetooth module and/or support the low energy broadcasts described herein.

In some embodiments, a temperature sensor 1171 is provided within the defibrillator itself for detecting the internal temperatures of the AED (as opposed to an environmental temperature), which is then used in the temperatures used to trigger the temperature fault notification and clearance messages. Preferable the temperature sensor is positioned adjacent one of the more temperature sensitive components such as battery 1170 so that the reported temperature is directly related to the internal temperature of the AED near the temperature sensitive component.

FIG. 17 illustrates some of the electrical components of a representative interface unit 200. In the illustrated embodiment, the interface unit 200 includes an interface controller (processor) 210, memory 213, a display screen 220, a communications module 230, an electrical connector 240, an interface unit power storage unit 250, and a location sensing module 260, all of which may be housed within the interface unit housing 202. The interface unit may also have software or firmware (such as an app 270) installed or installable in memory 213 having programmed instructions suitable for controlling operation of the interface unit and for coordinating communications between the interface unit 200 and the base defibrillation unit 110 and/or remote devices.

The processor 210 controls operation of the interface unit and coordinates communications with both the base unit 110 and remote devices such as a central server (as will be described in more detail below). In some embodiments, the processor 210 is arranged to execute a defibrillator app 270 that can be used both during use of the defibrillator system 100 during a cardiac arrest incident and to facilitate non-emergency monitoring or/or use of the defibrillator system 100. Similar to the base unit processor 130 discussed above, unless the context suggests otherwise, the processor 210 may take the form of a single processor, multiple processors, multiple processing cores and other processing unit configurations.

The display screen 220 is a touch sensitive screen suitable for displaying text, graphics and/or video under the direction of the processor 210 to assist both during both emergency situations and at other times. The touch sensitive screen is configured to receive inputs based on a graphical user interface displayed thereon. In some embodiments an optional graphics controller 222 may be provided to facilitate communications between the interface control processor 210 and the display screen 220. In other embodiments, functionalities of the graphics controller may be part of the processor 210.

The communication module 230 is provided to facilitate communications with remotely located devices such as the central server. The communications module 230 may be configured to utilize any suitable communications technology or combination of communication technologies including one or more of cellular communications, Wi-Fi, satellite communications, Bluetooth, NFC (Near Field Communications), Zigbee communications, DSRC (Dedicated Short-Range Communications) or any other now existing or later developed communications channels using any suitable communication protocol. By way of example, in the illustrated embodiment, the communications module 230 includes Wi-Fi, cellular and Bluetooth modules 231, 232 and 232 that facilitate Wi-Fi, cellular and Bluetooth communications, respectively.

The electrical connector 240 is configured to mate with interface connector 190 on the base defibrillator unit 110. The connectors 1190 and 240 are configured to facilitate communications between the defibrillator controller 130 and the interface unit's processor 210. The connectors 1190 and 240 are also preferably arranged to supply power from the interface unit 200 to the base unit 110 as will be described in more detail below. In some embodiments, power will only be provided in one direction—i.e., from the interface unit 200 to the base unit 110 and not in the reverse direction during operation. A good reason for this approach is that the defibrillator is the most important component from a safety standpoint, and it is often undesirable to draw power from the base unit to power other devices (including the interface unit 200) in a manner that could reduce the energy available to charge the discharge capacitor in the event of an emergency. However, in some embodiments, the power supply may be bi-directional (at least in some circumstance) if desired—as for example if the base unit is not in use, is fully charged and plugged into an external charging power supply, etc.; or if the power passed to the interface unit is not coming from the base unit's internal battery (e.g., it is coming from a charger, a mobile communication device, or other device connected or attached to the base unit), etc.

The connectors 1190 and 240 can take a variety of forms. They can be connectors with accompanying transceivers configured to handle processor level communications (such as UART, SPI, or I2C transceivers), with additional pins for power delivery (Power+GND), and connection verification (i.e. a pin that detects when there is a connection between the interface unit and the Base AED and triggers an interrupt on the Base AED signifying that there is not a unit connected). They can also be more standardized connectors such as USB connectors.

The interface power storage unit 250 provides power to operate the interface unit 210. In many embodiments, the power storage unit takes the form of a battery 252 with associated control components, although again a variety of other power storage technologies such as supercapacitors, ultracapacitors, etc. may be used in other embodiments. The associated control components may include components such as a battery charger and maintainer 254, which may include various safety monitors, and battery regulator 256. Preferably, the power storage unit 250 is rechargeable, although that is not a requirement. In some embodiments it may be desirable to utilize replaceable batteries (rechargeable or not) so that the batteries in the power storage unit 250 can be replaced when they near the end of their useful life. In some embodiments, the power storage unit 250 may also be arranged to supply supplemental power to the base unit 110. Depending on the structure and/or state of the base unit, the supplemental power can be used to help charge the discharge capacitor 150 during use; to power or provide supplemental power for the defibrillator electronics and/or to charge the base defibrillator unit's power storage unit 1170. In other embodiments, a supplemental battery within the interface unit (not shown) may be used to provide the supplemental power for the base unit rather than the power storage unit 250.

The location sensing module may incorporate a variety of technologies including Global Navigation Satellite Systems (GNSS) (e.g., GPS), Wi-Fi positioning, cellular triangulation, assisted GPS, Bluetooth Beacons, Near-Field Communications (NFC) and/or other location determining technologies. When requested, the interface unit can report its current location based on the location sensing technology that is believed to have the best accuracy under the then-present circumstances.

The interface unit may also optionally include various environmental sensors 263 and other peripheral components 266. When desired, the interface unit may include any of a wide variety of different types of sensors and peripheral components. For example, in selected embodiments, the interface unit may include one or more accelerometers and/or gyroscopes, a temperature sensor, a humidity sensor, a time of day or any other desired sensors or components.

The interface unit 200 is preferably configured to securely mechanically attach to the base unit 110. Typically, the interface unit is detachable such that it may be separated from the base unit if desired—although in other embodiments, the attachment may be more permanent in nature. The specific mechanical attachment utilized may vary widely in accordance with the needs of any particular embodiment. In some embodiments, press or form fitting attachment structures are used, while in others, latch and catch mechanisms, snap fit structures, etc. are utilized alone or in combination to releasably attach the interface unit to the base. However, it should be appreciated that a wide variety of other structures can be used in other embodiments. A few specific mechanical attachment structures are described below. In some embodiments, the interface unit includes an attachment sensor (not shown) that senses when the interface unit is attached to a base unit.

In some embodiments, the interface unit may also include one or more biometric sensors 270. The biometric sensors may vary based on the needs of any particular defibrillator. Some of the biometric sensors may be suitable for use in detecting or evaluating CPR performed during emergency use of the defibrillator. Other biometrics may be useful in more general health management applications. For example, in some embodiments, the biometric sensors may include one or more of a pulse or heart rhythm sensor, a blood pressure sensor, a glucose monitor, a pulse oximeter, an ECG monitor, a sleep tracker, a thermometer, etc.

A benefit of the described modular defibrillator architecture is that the interface unit can be (and preferably is) designed to provide robust connectivity, effectively making the defibrillator a highly connected device. The relatively large touch sensitive display screen provides an interface that can be easily used by users of most any age, and the dedicated interface unit processor(s) and corresponding memory allow the interface unit to be programmed to provide a number of functionalities that are not available in defibrillators that are commercially available today.

It should be appreciated that the described modular architecture helps overcome a number of practical challenges that have hindered widespread adoption of defibrillator connectivity. One particular challenge relates to security. If a defibrillator has the ability to bidirectionally communicate with the external systems through the Internet or other public networks, such connectivity introduces security risks that would not otherwise exist. This can also lead to regulatory challenges. For example, a practical challenge that is faced when incorporating a communications unit directly into the AED is that, in general, AEDS are highly regulated medical devices. For example, in the United States, new AEDs are Class III Medical Devices that require premarket approval (PMA) from the U.S. Food and Drug Administration (FDA) prior to sale in the United States—which is the most stringent type of medical device marketing application required by the FDA. The PMA approval process is quite rigorous and can take a significant amount of time. When the communications unit is an integral part of the AED it is subject to the full PMA review process which means that anytime there is a desire to update any of the communication unit's software, such updates can subject to extensive review process. In practice, the software used in many communications technologies tends to be updated or patched on a fairly regular basis. Such updates may be designed to patch newly discovered security vulnerabilities, eliminate bugs, facilitate compatibility with additional devices or protocols, add new functionalities, and/or for a variety of different purposes. Unfortunately, such regular updates are fairly incompatible with the PMA review process which tends to be protracted and expensive.

In some embodiments, the interface unit 200 is designed to qualify as a Medical Device Data System (MDDS) in the U.S. Food and Drug Administration (FDA) regulatory framework. MDDS refers to a category of medical devices that are designed to collect, store, convert formats, display and/or transfer medical data. MDDS devices are not intended to be used for making diagnostic decisions or to control the functions of other medical devices. Rather, they primarily serve as conduits for transmitting and managing medical data. Medical Device Data Systems are typically designated as Class I exempt Medical Devices by the FDA and as such they are still subject to regulations, but they do not require pre-marketing FDA approval.

There are significant advantages to designing the interface unit as a MDDS. If an external mechanism (such as an interface device, a server or a software App intended for execution on a mobile device) is required for emergency operation of the AED, or controls or alters any functions of the AED in any way during emergency use of the AED, then such hardware or software products are subject to PMA approval. Alternatively, if such hardware or software devices do not control the AED but rather only analyzes and/or interprets data to be rendered to the user, then such devices may be subject to a shorter (yet rigorous) pre-marketing approval process in some jurisdictions—as for example a 510 k approval process in the United States. In order to mitigate the delays inherent in these types pre-marketing regulatory approval, in some preferred embodiments, the interface unit 200 is designed to comply with the definitions and requirements of an MDDS. As such, it does not control the function or operation of the base defibrillator unit in any way during emergency use of the defibrillator. Furthermore, it does not interpret data to be presented to a user during emergency use of the defibrillator. To the extent it presents information to a user during an emergency, it simply presents information under the direction of the AED. By taking care to ensure that the interface unit acts as a MDDS, the defibrillator's security is further enhanced since the performance of the AED would not be compromised even if the interface unit is rendered non-functional by a malicious attack.

Given that the interface unit is a connected device that has a powerful processor (or processors) and a number of familiar I/O components including, for example, a touch sensitive display screen, Wi-Fi, cellular and other wireless communications capabilities, a speaker, a microphone and optionally a camera, the interface unit can be programmed to provide a number of the functionalities described herein that are not available in defibrillators today without impacting the functionality of the base defibrillator unit in any way. For example, in some preferred embodiments, any/all administrator supplied content such as the screen savers and Wi-Fi certificate is only used by the interface unit. That is, the content is received by the interface unit, installed on the interface unit, and executed exclusively on the interface unit. In these embodiments, such content is never provided to the base defibrillator unit and does not impact the operation of the base defibrillator unit in any way. This is a significant advantage from both security and regulatory standpoints.

In the modular architecture described with reference to FIGS. 15-17 the AED's Wi-Fi, cellular and Satellite communications are all handled exclusively by the interface unit. Similarly, touch screen-based user interactions with the AED are controlled exclusively by the interface unit and location services are provided by the interface unit. In such embodiments, the AED based functionalities of many of the described services may be performed exclusively by the interface unit without requiring any interaction with or input from the base defibrillator unit. Examples of these services/functionalities include the AED actions performed in: (i) the setting and enforcement of the PIN code or password based access controls; (ii) the selection of, and connection to, communication networks including any required password or certificate based authentication and the setting of passwords and/or the provision of network certificates; responses to location and/or status requests (e.g., the Ping AED feature); AED actions and responses in the Lost/Stolen mode; the setting of certain power modes (e.g., Set Power Mode commands that don't impact the functionality of the base defibrillator unit); the selection of a training sequence; etc.

In any of the cases, the interface unit does not pass the commands or requests received from the management server or a user on to the base defibrillator unit, or even interact with the base defibrillator unit as part of its response to the command or request. This can help extend the life of the base defibrillator unit's battery since the AED can implement the request without even awakening the base defibrillator unit.

In other circumstances the interface unit may need to interact with the base defibrillator in order to either respond and/or implement a received request or command. For example, when a Set Power Modes command is received by the interface unit that requires a change to the base defibrillator unit's settings, the base defibrillator unit must be informed of that change. In some embodiments the base defibrillator unit has a Bluetooth or other short-range communications module and any command that disables or enables the such module or impacts the frequency or nature of the advertisements or beacons broadcast by the such mode must be conveyed to the base defibrillator unit. Of course, there are many other examples as well.

Notifications and Summary Reports

In some of the embodiments described above, notifications are or can be sent to designated administrators in response to specific events detected by the AED (e.g., activation of the AED, detected faults, fault clearances, lack of synchronization, etc.). In some embodiments, the management platform may also include an interface that allows the user to set their notification preferences.

As is apparent from the discussion above, there are a number of different types of notifications and summary reports that may be provided to administrators and other interested parties via either the management platform or other messaging technologies. These include (but are not limited to) fleet health summaries, incident related notifications, AED or fleet health related notifications, etc.

In some embodiments, the administrator is able to specify how frequently they would like to receive fleet health summaries—e.g., on a monthly, weekly or daily basis. These documents summarize all fleet health related changes that occurred in the corresponding reporting period.

In some embodiments, the administrator is able to select whether or not to receive real-time Incident Notifications—e.g., Email and/or SMS notifications when an Incident Activation is detected. When opted into, such notifications may be triggered based on designer preferences. In some implementations, such notifications are sent when the management server learns that pads have been place on a patient and one shock/no shock analysis has been performed on the patient.

In some embodiments, the administrator is able to select which Health States they want to receive health change notifications for: Unhealthy, At Risk, Unknown, and/or Healthy. They can also select whether the notifications should ve sent via SMS and/or Email. In some embodiments, Health State notifications are sent under two different timings—"Immediate" and "Nightly". Immediate notifications are higher priority notification sent substantially immediately after the management server learns of a particular health state change (e.g., a temperature fault or a critical battery charge issue). Nightly notifications (such as upcoming pad replacement notifications, training pads installed, synch status errors and various faults detected during AED self-tests) are collected and sent once a day.

Closing

In the discussion above, frequent references are made to administrators using the described systems. In general, the administrator can be any authorized user associated with the AED. In many cases the administrator is the owner of the AEDs or an employee or other affiliate of the owner, but in other cases the administrator may be another person that has some level of administrative and/or viewing rights with respect to the AED—as for example, a third party responsible for managing an organization's AEDs. In another example, in the context of a jurisdiction with an AED inclusive responder network, an official or volunteer associated with the responder network may have certain administrative and/or viewing rights for AEDs included in the network, which may be owned by a variety of different entities.

Many organizations may have a number of personnel inside or outside of the organization that are able to access the management platform and each of these individuals are generally referred to "administrators" herein. However, their respective associated AEDs and their respective rights regarding viewing and/or applying setting to their associated AEDs associated with the organization may vary. In general, the dashboard is preferably arranged so that the AEDs reflected in their respective dashboards and other parts of the management platform user interface are limited to the AEDs that they individually are responsible for. Thus, while some administrators may have viewing access and settings/content control over all of the organizations AEDs, others may have only viewing privileges, or only will be associated with a subset of the organizations AEDs (e.g., the AEDs at a particular location) and/or only have the right to change certain settings on a subset of the organizations AEDs.

In the discussion above, several references are made to identifying or associating groups of AEDs. The group designations may be made in any suitable way—as for example, by assigning group labels to AEDs (which may be location labels such a Palo Alto campus, a particular building, a city, etc.). Another noteworthy group label is "all" which encompasses all AEDs associated with the administrator or all AEDs that the administrator has appropriate settings control rights for.

Although only a few embodiments of the invention have been described in detail, it should be appreciated that the invention may be implemented in many other forms without departing from the spirit or scope of the invention. Therefore, the present embodiments should be considered illustrative and not restrictive, and the invention is not to be limited to the details given herein, but may be modified within the scope and equivalents of the appended claims.

What is claimed is:

1. A method of obtaining updated status information from an automated external defibrillator (AED) capable of delivering a defibrillation shock to a cardiac arrest victim, the method comprising:

at an AED management platform user interface rendered on an administrator computing device, receiving an administrator input that requests updated status information from a target AED;

in response to the administrator inputted request, sending an update request message from the AED management platform user interface to an AED management server located remotely relative to the AED management platform user interface;

by the AED management server, at least partially in response to reception of the update request message, sending a status check message to the target AED that prompts the target AED to convey current AED status information to the AED management server;

at the AED management server, receiving the current status information from the target AED;

sending the requested updated status information from the AED management server to the AED management platform user interface, wherein the updated status information includes at least some of the current status information; and in response to receiving the requested updated status information, rendering the requested updated status information within the AED management platform user interface on a display screen associated with the administrator computing device.

2. A method as recited in claim 1 wherein the updated status information is rendered within the AED management platform user interface in real-time in response to the administrator inputted request.

3. A method as recited in claim 1 wherein:

in response to reception of the update request message, the AED management server sends a paging message to the target AED; and in response to receiving the paging message, the target AED opens a connection with the AED management server and sends the current AED status information to the AED management server over the connection.

4. A method as recited in claim 1 wherein the updated status information is or includes a current location of the target AED.

5. A method as recited in claim 1 wherein the updated status information rendered within the AED management platform includes a time that the target AED to conveyed the current AED status information to the AED management server.

6. An automated external defibrillator (AED) management platform user interface embodied in a computer readable media, the AED management platform user interface being configured to display a prompt status check widget in association with a first AED, wherein when the prompt status check widget is activated, the AED management platform user interface sends an update AED status information request to an AED management server that prompts the AED management server to send a status check-in request to the first AED that prompts the first AED to send a first message to the AED management server that provides at least one of a current location of the AED and selected current status information regarding the AED.

7. An AED management platform user interface as recited in claim 6 wherein the prompt status check widget is accessible or rendered within an AED status page associated with the first AED, the AED management platform user interface being further configured to receive updated information from the AED management server at least partially in response to the update AED status information request, and to render selected updated information in the AED status page without requiring further input from a user.

8. An AED management platform user interface as recited in claim 7 wherein the AED status page includes a map, and the first message and the updated information both include the current location of the AED and upon receipt of the updated status information, the AED status page is updated to show the received current location of the AED on the map.

9. An AED management platform user interface as recited in claim 8 further comprising rendering a refresh time in the AED management platform user interface that indicates a time that the current location was provided by the AED.

10. An automated external defibrillator (AED) management user interface embodied in a computer readable media, the AED management user interface being configured to display a lost mode widget in association with a first AED, wherein when the lost mode widget is activated, the AED management user interface sends a first message to an AED management server that prompts the AED management server to send an activate Missing Protocol command to the first AED that prompts the first AED to send a second message to the AED management server that provides a current location of the AED.

11. An AED management user interface as recited in claim 10 wherein the activate Missing Protocol command causes the AED to render a render a visual message on a display associated with the AED that provide return instructions that provide instructions indicating how to return the AED to a designated location or to a designated entity, owner, administrator or person.

12. An AED management user interface as recited in claim 10 wherein the activate Missing Protocol command causes the AED to render an audio alert intended to bring attention to the AED.

13. An AED management user interface as recited in claim 10 wherein the activate Missing Protocol command causes the AED to repeatedly transmit messages to the messages to the AED management server that each provide a then current location of the AED.

14. An automated external defibrillator (AED) capable of delivering a defibrillation shock, the AED having a processor and memory having programmed instructions configured to, in response to the reception of an activate missing protocol message from a remotely located server:

cause a first message to be sent to the server that indicates a current location of the AED; and cause an audio or visual message to be generated or rendered that provides return instructions for the AED.

15. An AED as recited in claim 14 wherein the programmed instructions are further configured to cause the AED to periodically transmit location update messages to the server that update the current location of the AED until a missing protocol executed by the AED is cancelled.

16. An AED as recited in claim 14 wherein the programmed instructions cause the AED to generate both audio and visual return instructions.

17. An AED as recited in claim 14 wherein the return instructions include at least one of:

a request that the AED be returned to a designated location; and contact information indicating a contact for returning the AED.

18. An AED as recited in claim 17 wherein the designated location or contact information is received from the server as part of the activate missing protocol message.

19. An AED as recited in claim 18 further wherein the programmed instructions are further configured to cause a map to be rendered on a display screen of the AED that shows the designated location and directions to the designated location.

20. A method comprising:

at a medical device management platform rendered on an administrator computing device, receiving a user inputted lost mode selection for a selected therapeutic medical device and at least partially in response to the lost mode selection sending a lost mode activation request to a management server located remotely relative to the administrator computing device;

at the management server, receiving the lost mode activation request, and a least partially in response to the lost mode activation request, sending a lost mode activation command to the selected therapeutic medical device; and at the selected therapeutic medical device, in response to receipt of the lost mode activation command, (a) sending first message to the management server that indicates a current location of the selected therapeutic medical device, and (b) generating or rendering an audio or visual message that provides return instructions for the therapeutic medical device;

requests that the AED be returned to a designated location, or (ii) rendering a visual message on the display screen that requests that the AED be returned to the designated location.

21. A method as recited in claim 20 further comprising:

at the management server, at least partially in response to receiving the first message, transmitting a second message to the selected therapeutic medical device that indicates the current location of the selected therapeutic medical device; and at the medical device management platform, at least partially in response to receiving the second message, showing the current location on a map rendered in the medical device management platform.

22. A method as recited in claim 20 wherein the therapeutic medical device generates or renders both audio and visual return instructions.

23. A method as recited in claim 20 wherein the return instructions include at least one of:

a request that the AED be returned to a designated location; and contact information indicating a contact for returning the AED.

24. A method as recited in claim 23 further comprising, at the selected therapeutic medical device rendering a map on a display of the therapeutic medical device that shows the designated location and provides directions to the designated location.

25. A method as recited in claim 20 further comprising;

in response to a user input on the administrator computing device requesting termination of the lost mode, transmitting a terminate lost mode request from the administrator computing device to the management server;

by the management server, at least partially in response to receiving the terminate lost mode request, transmitting a terminate lost mode command to the selected therapeutic medical device; and by the therapeutic medical device at least partially in response to the reception of the terminate lost mode command, stopping the generation or rendering of the audio or visual message that provides return instructions for the therapeutic medical device.

\* \* \* \* \*